(12) United States Patent
Sverdlik et al.

(10) Patent No.: US 11,691,033 B2
(45) Date of Patent: Jul. 4, 2023

(54) SKIN TREATMENT APPLICATOR

(71) Applicant: Sofwave Medical Ltd., Yokneam (IL)

(72) Inventors: Ariel Sverdlik, Tel-Aviv (IL); Shimon Eckhouse, Haifa (IL); Rana Bassal, Haifa (IL); Ilya Glants, Petach-Tivka (IL)

(73) Assignee: Sofwave Medical Ltd., Yokneam Illit (IL)

( * ) Notice: Subject to any disclaimer, the term of this patent is extended or adjusted under 35 U.S.C. 154(b) by 0 days.

(21) Appl. No.: 17/307,051

(22) Filed: May 4, 2021

(65) Prior Publication Data

US 2021/0339053 A1 Nov. 4, 2021

Related U.S. Application Data

(63) Continuation of application No. 16/307,503, filed as application No. PCT/IL2017/050638 on Jun. 6, 2017.
(Continued)

(51) Int. Cl.
*A61N 7/02* (2006.01)
*B06B 3/00* (2006.01)
(Continued)

(52) U.S. Cl.
CPC ............ *A61N 7/02* (2013.01); *B06B 1/0622* (2013.01); *B06B 1/0662* (2013.01); *B06B 3/00* (2013.01);
(Continued)

(58) Field of Classification Search
CPC ............ A61N 7/02; A61N 2007/0034; A61N 2007/0078; B06B 3/00; B06B 1/0622;
(Continued)

(56) References Cited

U.S. PATENT DOCUMENTS 4,101,795 A * 7/1978 Fukumoto ............ A61B 8/4494
367/154
4,800,316 A 6/1989 Ju-Zhen
(Continued)

FOREIGN PATENT DOCUMENTS

CN 1430538 7/2003
CN 101166472 4/2008
(Continued)

OTHER PUBLICATIONS

Official Action dated Jul. 30, 2021 from the US Patent and Trademark Office Re. U.S. Appl. No. 16/307,503. (39 pages).
(Continued)

*Primary Examiner* — Rene T Towa

(57) ABSTRACT

Some embodiments of the invention relate to an applicator for applying ultrasound energy to a tissue volume, comprising: an array comprising a plurality of ultrasound transducers, the transducers arranged side by side, the transducers configured to emit unfocused ultrasound energy suitable to thermally damage at least a portion of the tissue volume, each of the transducers comprising a coating thin enough so as not to substantially affect heat transfer via the coating to the tissue; and a cooling module configured to apply cooling via the transducers to prevent overheating of a surface of the tissue volume being contacted by the transducers.

21 Claims, 41 Drawing Sheets
(25 of 41 Drawing Sheet(s) Filed in Color)

Related U.S. Application Data

(60) Provisional application No. 62/345,918, filed on Jun. 6, 2016.

(51) Int. Cl.
    *H10N 30/80*     (2023.01)
    *H10N 30/853*     (2023.01)
    *B06B 1/06*     (2006.01)
    *A61N 7/00*     (2006.01)

(52) U.S. Cl.
    CPC ......... *H10N 30/80* (2023.02); *H10N 30/8554* (2023.02); *A61N 2007/0034* (2013.01); *A61N 2007/0078* (2013.01); *B06B 2201/76* (2013.01)

(58) Field of Classification Search
    CPC ... B06B 1/0662; B06B 2201/76; H01L 41/04; H01L 41/1876
    See application file for complete search history.

(56) References Cited

U.S. PATENT DOCUMENTS

| | | | |
|---|---|---|---|
| 5,601,526 A * | 2/1997 | Chapelon | A61N 7/02 601/2 |
| 5,620,479 A | 4/1997 | Diederich | |
| 5,630,837 A | 5/1997 | Crowley | |
| 6,050,943 A * | 4/2000 | Slayton | A61N 7/02 600/439 |
| 6,589,174 B1 | 7/2003 | Chopra et al. | |
| 6,595,934 B1 | 7/2003 | Hissong et al. | |
| 7,582,050 B2 | 9/2009 | Schlorff et al. | |
| 2003/0201696 A1 | 10/2003 | Muramatsu et al. | |
| 2003/0229331 A1 | 12/2003 | Brisken et al. | |
| 2004/0267252 A1 | 12/2004 | Washington et al. | |
| 2005/0251235 A1 | 11/2005 | Schlorff et al. | |
| 2007/0038156 A1 * | 2/2007 | Rosenberg | A61B 18/14 601/2 |
| 2008/0183110 A1 | 7/2008 | Davenport et al. | |
| 2008/0195000 A1 * | 8/2008 | Spooner | A61H 23/0245 601/2 |
| 2009/0312693 A1 | 12/2009 | Thapliyal et al. | |
| 2011/0270137 A1 | 11/2011 | Goren et al. | |
| 2012/0016239 A1 | 1/2012 | Barthe et al. | |
| 2012/0029353 A1 | 2/2012 | Slayton et al. | |
| 2012/0095372 A1 | 4/2012 | Sverdlik et al. | |
| 2012/0271294 A1 | 10/2012 | Barthe et al. | |
| 2012/0310232 A1 | 12/2012 | Erez | |
| 2013/0012842 A1 * | 1/2013 | Barthe | A61N 7/00 601/3 |
| 2013/0068382 A1 | 3/2013 | Harhen et al. | |
| 2013/0134834 A1 | 5/2013 | Yoshikawa et al. | |
| 2014/0184022 A1 | 7/2014 | Kobayashi et al. | |
| 2015/0283408 A1 * | 10/2015 | Barthe | A61B 8/0858 601/3 |
| 2016/0016015 A1 | 1/2016 | Slayton et al. | |
| 2016/0089550 A1 * | 3/2016 | DeBenedictis | A61N 7/02 601/3 |
| 2016/0310212 A1 * | 10/2016 | Domankevitz | A61B 18/203 |
| 2017/0028227 A1 | 2/2017 | Emery et al. | |
| 2018/0161002 A1 * | 6/2018 | Alford | A61N 7/02 |
| 2019/0009111 A1 | 1/2019 | Myhr et al. | |
| 2019/0105520 A1 | 4/2019 | Sverdlik et al. | |
| 2019/0143149 A1 | 5/2019 | Sverdlik et al. | |
| 2021/0252314 A1 | 8/2021 | Sverdlik et al. | |

FOREIGN PATENT DOCUMENTS

| | | |
|---|---|---|
| CN | 102098982 | 6/2011 |
| CN | 102958565 | 3/2013 |
| CN | 103371850 | 10/2013 |
| CN | 103987334 | 8/2014 |
| EP | 2629736 | 2/2017 |
| WO | WO 00/45445 | 8/2000 |
| WO | WO 2006/114736 | 11/2006 |
| WO | WO 2013/033066 | 3/2013 |
| WO | WO 2014/022777 | 2/2014 |
| WO | WO 2016/090175 | 6/2016 |
| WO | WO 2015/106118 | 7/2017 |
| WO | WO 2017/212489 | 12/2017 |
| WO | WO 2020/194312 | 10/2020 |

OTHER PUBLICATIONS

"PDMS-MIT", 6.777J/2.751J Material Property Database, Massachusetts Institute of Technology, 2020.

International Preliminary Report on Patentability dated Dec. 20, 2018 From the International Bureau of WIPO Re. Application No. PCT/IL2017/050638. (16 Pages).

International Search Report and the Written Opinion dated Jan. 2, 2018 From the International Searching Authority Re. Application No. PCT/IL2017/050638. (26 Pages).

International Search Report and the Written Opinion dated Jun. 2, 2020 From the International Searching Authority Re. Application No. PCT/IL2020/050368. (36 Pages).

Invitation to Pay Additional Fees, Communication Relating to the Results of the Partial International Search and the Provisional Opinion dated Oct. 6, 2017 From the international Searching Authority Re. Application No. PCT/IL2017/050638. (19 Pages).

Notification of Office Action and Search Report dated Sep. 2, 2020 From the China National Intellectual Property Administration Re. Application No. 201780044046.5 and Its Translation Into English. (10 Pages).

Notification of Office Action and Search Report dated Sep. 26, 2019 From the State Intellectual Property Office of the People's Republic of China Re. Application No. 201780044046.5. (10 Pages).

Official Action dated Feb. 17, 2021 From the US Patent and Trademark Office Re. U.S. Appl. No. 16/211,288. (37 Pages).

Restriction Official Action dated Oct. 27, 2020 from the US Patent and Trademark Office Re. U.S. Appl. No. 16/211,288. (8 pages).

Translation Dated Oct. 20, 2019 of Notification of Office Action dated Sep. 26, 2019 From the State Intellectual Property Office of the People's Republic of China Re. Application No. 201780044046.5. (8 Pages).

Translation Dated Sep. 21, 2020 of Notification of Office Action dated Sep. 2, 2020 From the China National Intellectual Property Administration Re. Application No. 201780044046.5. (8 Pages).

Epoxy Technology et al. "EPO-TEK Adhesives Applications", Epoxy Technology Inc., XP055410092, Data Sheets, p. 1-16, Dec. 31, 2013. p. 3-5.

Lee at al. "Flexible Piezoelectric Micromachined Ultrasonic Transducer (pMUT) for Application in Brain Stimulation", Microsystem Technologies, 23: 2321-2328, Pubhshed: Apr. 29, 2016.

Final Official Action dated Jan. 21, 2022 from US Patent and Trademark Office Re. U.S. Appl. No. 16/307,503. (38 pages).

Interview Summary dated Mar. 1, 2022 from US Patent and Trademark Office Re. U.S. Appl. No. 16/307,503. (3 pages).

Interview Summary dated Mar. 1, 2022 from US Patent and Trademark Office Re. U.S. Appl. No. 17/307,032. (2 pages).

Official Action dated Jan. 18, 2022 from US Patent and Trademark Office Re. U.S. Appl. No. 17/307,032. (26 pages).

Advisory Action dated Apr. 15, 2022 together with Interview Summary dated Apr. 12, 2022 from US Patent and Trademark Office Re. U.S. Appl. No. 16/307,503. (6 pages).

Final Official Action dated Apr. 11, 2022 from US Patent and Trademark Office Re. U.S. Appl. No. 17/307,032. (20 pages).

Official Action dated Oct. 14, 2022 from US Patent and Trademark Office Re. U.S. Appl. No. 17/307,032. (20 pages).

Final Official Action dated Feb. 6, 2023 from the US Patent and Trademark Office Re. U.S. Appl. No. 17/307,032. (25 pages).

\* cited by examiner

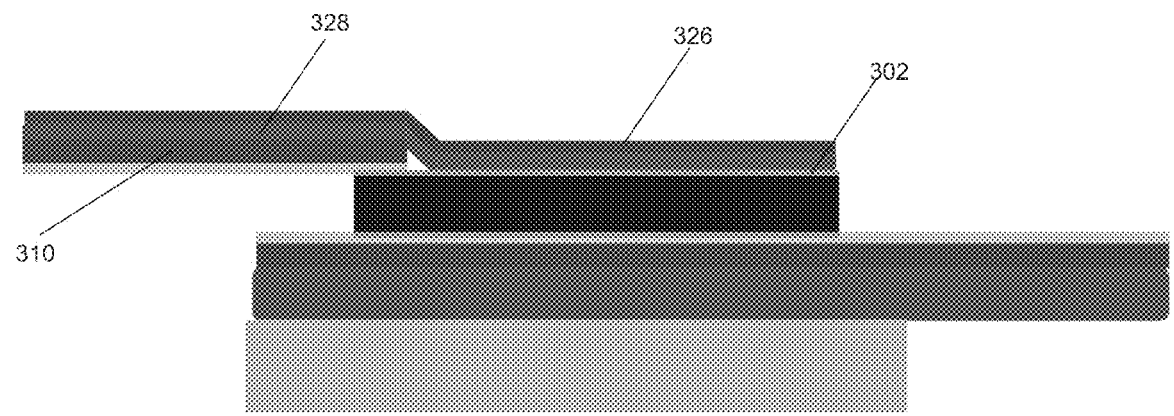
FIG. 3D
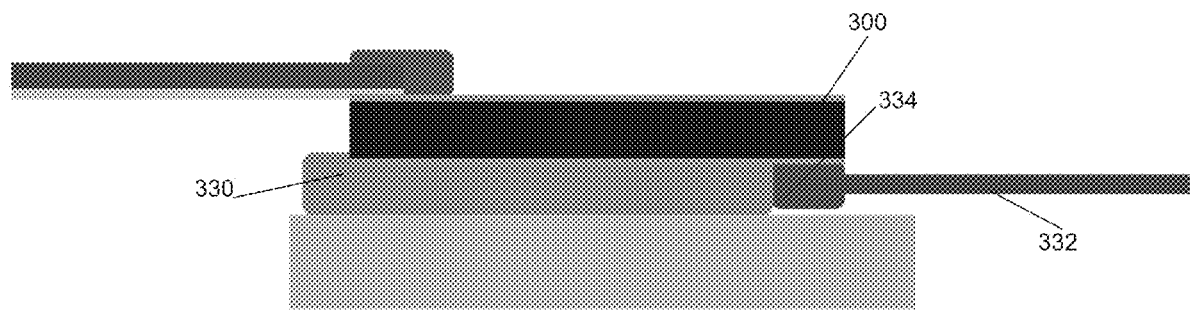
FIG. 3E
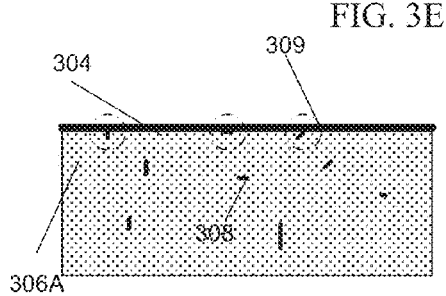 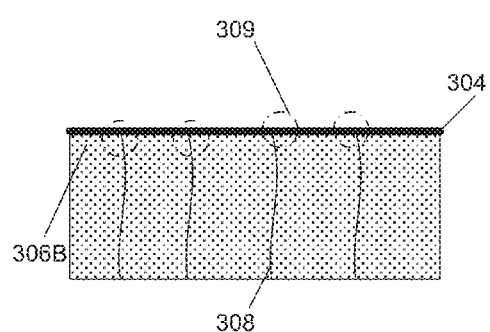
FIG. 3F

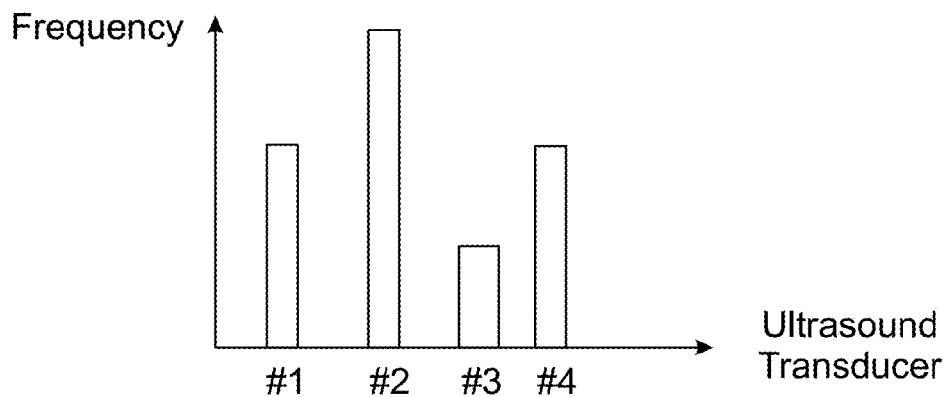

FIG. 9A

Freq set 01
  Element length [mm] = 5
  Element width [mm] = 1

| # | Element work modality | Working Frequency [MHz] | Penetration depth at 50% energy deposition [mm] | Transducer Efficiancy [%] | Ultrasonic intensity [W/cm^2] | Electric power [W] | Ultrasonic Tissue Heating [W] | Transducer Heat Losses [W] |
|---|---|---|---|---|---|---|---|---|
| 1 | High Intensity Ultrasound | 11 | 6 | 50 | 30 | 3.00 | 1.50 | 1.50 |
| 2 | Shallow heating, 2nd Harmonic | 22 | 2 | 20 | 8 | 2.00 | 0.40 | 1.60 |
| 3 | Shallow heating, 3rd Harmonic | 33 | 1 | 30 | 12 | 2.00 | 0.60 | 1.40 |
| 4 | Contact heating, off resonance | 9 | NR | 5 | 1.5 | 1.50 | 0.08 | 1.43 |
| 5 | Shallow heating, 3rd Harmonic | 33 | 1 | 30 | 12 | 2.00 | 0.60 | 1.40 |
| 6 | Shallow heating, 2nd Harmonic | 22 | 2 | 20 | 8 | 2.00 | 0.40 | 1.60 |
| 7 | High Intensity Ultrasound | 11 | 6 | 50 | 30 | 3.00 | 1.50 | 1.50 |
| 8 | Shallow heating, 2nd Harmonic | 22 | 2 | 20 | 8 | 2.00 | 0.40 | 1.60 |
| 9 | Shallow heating, 3rd Harmonic | 33 | 1 | 30 | 12 | 2.00 | 0.60 | 1.40 |
| 10 | Contact heating, off resonance | 9 | NR | 5 | 1.5 | 1.50 | 0.08 | 1.43 |
| 11 | Shallow heating, 3rd Harmonic | 33 | 1 | 30 | 12 | 2.00 | 0.60 | 1.40 |
| 12 | Shallow heating, 2nd Harmonic | 22 | 2 | 20 | 8 | 2.00 | 0.40 | 1.60 |
| 13 | High Intensity Ultrasound | 11 | 6 | 50 | 30 | 3.00 | 1.50 | 1.50 |
| 14 | Shallow heating, 2nd Harmonic | 22 | 2 | 20 | 8 | 2.00 | 0.40 | 1.60 |
| 15 | Shallow heating, 3rd Harmonic | 33 | 1 | 30 | 12 | 2.00 | 0.60 | 1.40 |
| 16 | Contact heating, off resonance | 9 | NR | 5 | 1.5 | 1.50 | 0.08 | 1.43 |
| 17 | Shallow heating, 3rd Harmonic | 33 | 1 | 30 | 12 | 2.00 | 0.60 | 1.40 |
| 18 | Shallow heating, 2nd Harmonic | 22 | 2 | 20 | 8 | 2.00 | 0.40 | 1.60 |
| 19 | High Intensity Ultrasound | 11 | 6 | 50 | 30 | 3.00 | 1.50 | 1.50 |

FIG. 9B

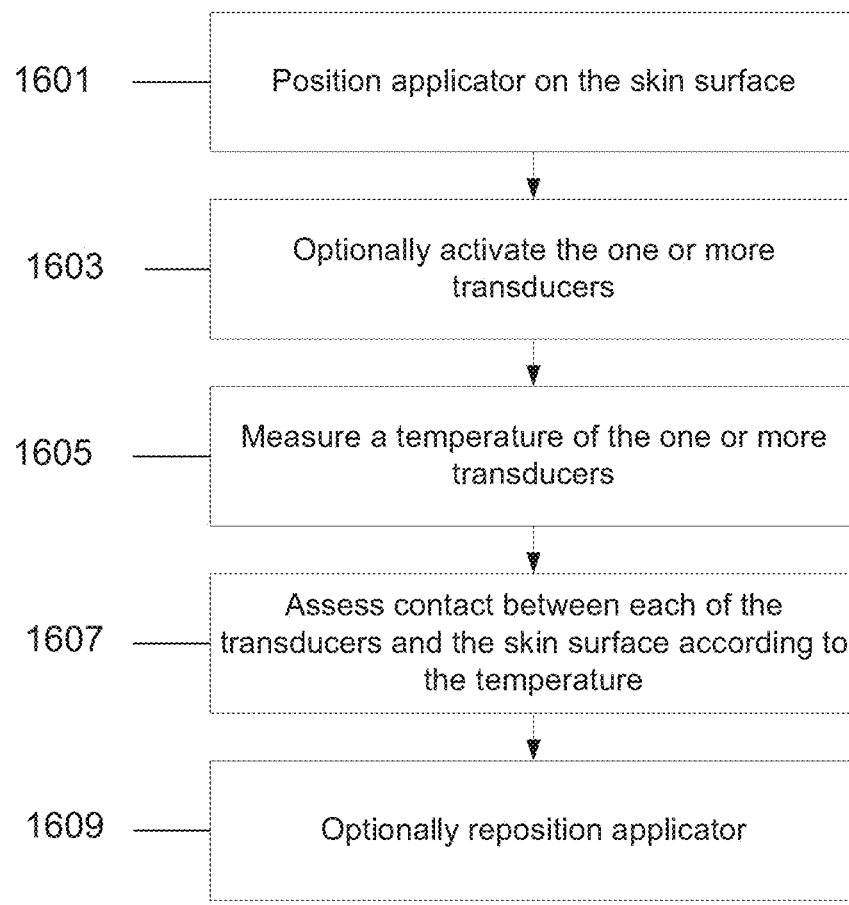
FIG. 16A1

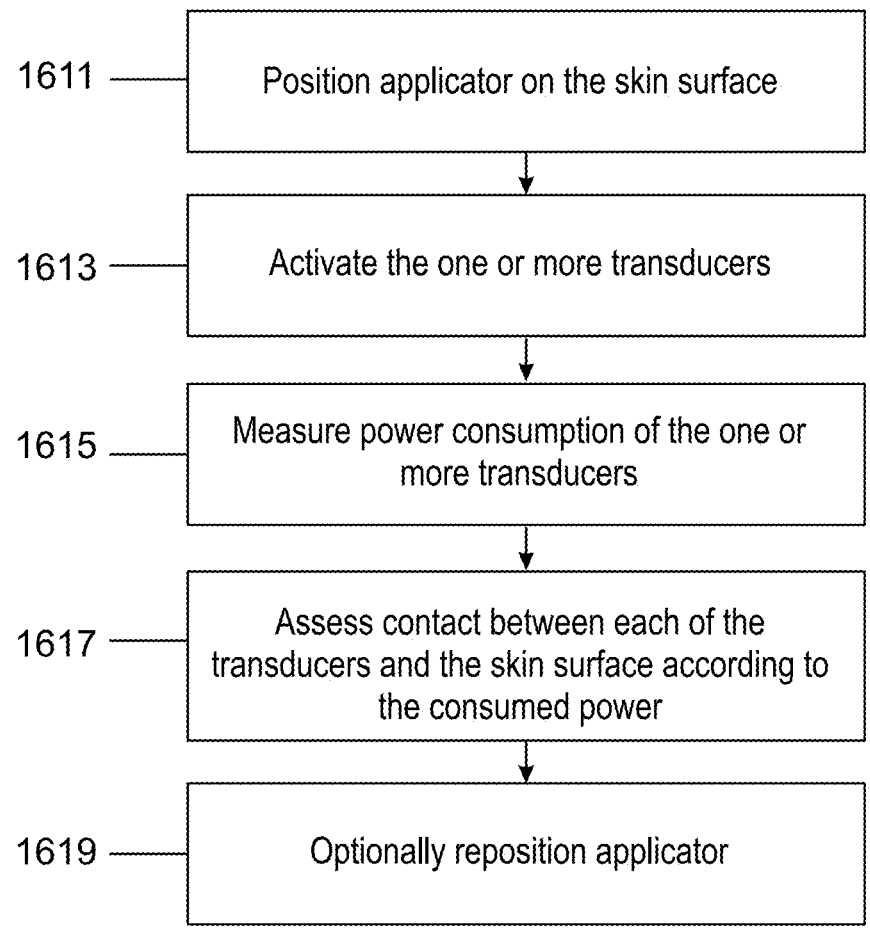
FIG. 16D1

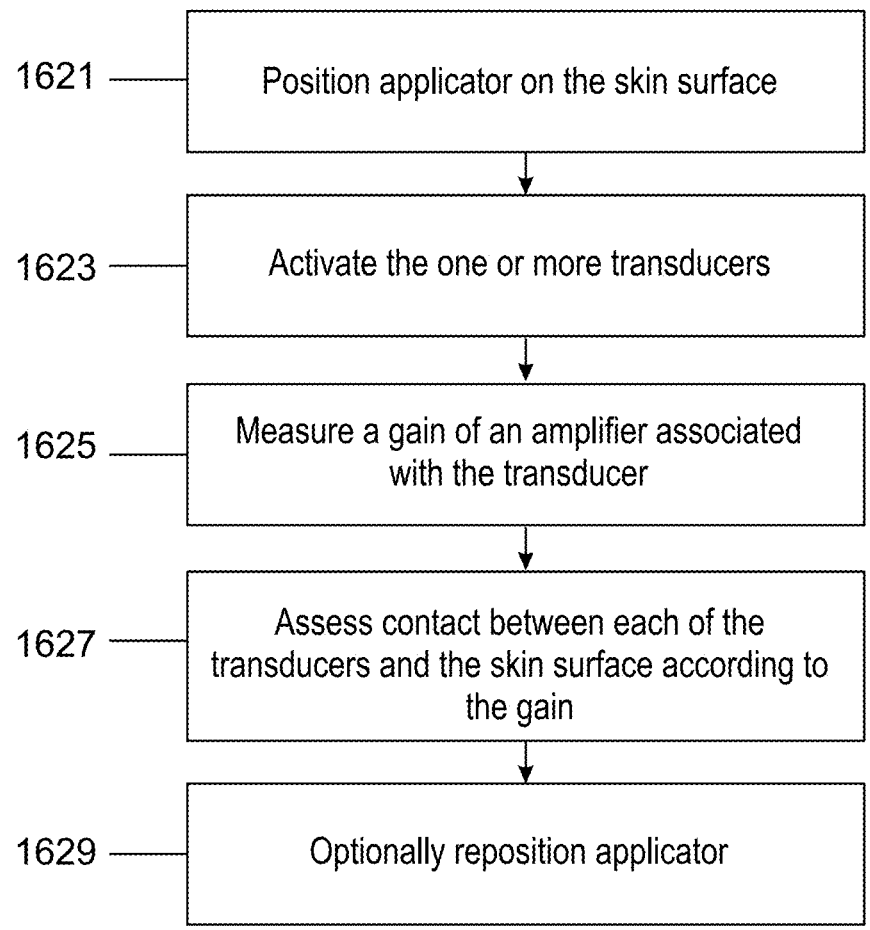
FIG. 16F1

Treatment Parameters and Setup

| Parameter | Setup |
|---|---|
| Transducer Active Length [mm] | 7 |
| Frequency [MHz] | 11.5 |
| No. of Active Transducers | 1, 7 |
| Pre-cooling [Sec] | 1 |
| Treatment Duration [Sec] | 4 |
| Treatment Duration [Sec] | 4 |
| Pig General Skin Temperature [C] | 31.6 |
| Treatment Start Skin Temp [C] (AVG) | 6.5 |
| Treatment End Skin Temp [C] (AVG) | 11.4 |

FIG. 19A

Intensities = 17.9, 20.0, 21.7 [W/cm^2] ; Points: 1-DEF
Visible burn on epidermis: No Intensities = 25.9, 27.8 [W/cm^2] ; Points: 1-HI
Visible burn on epidermis: No Intensity = 16.8 [W/cm^2] ; Point: 2-I
Visible burn on epidermis: NO Intensity = 17.8 [W/cm^2] ; Point: 2-M
Visible burn on epidermis: NO Intensity = 20.7 [W/cm^2] ; Point: 3-I
Visible burn on epidermis: NO Intensity = 23.5 [W/cm^2] ; Point: 5-M
Visible burn on epidermis: NO Intensity = 24.7 [W/cm^2] ; Point: 5-I
Visible burn on epidermis: YES Intensity = 26.4 [W/cm^2] ; Point: 5-A
Visible burn on epidermis: YES

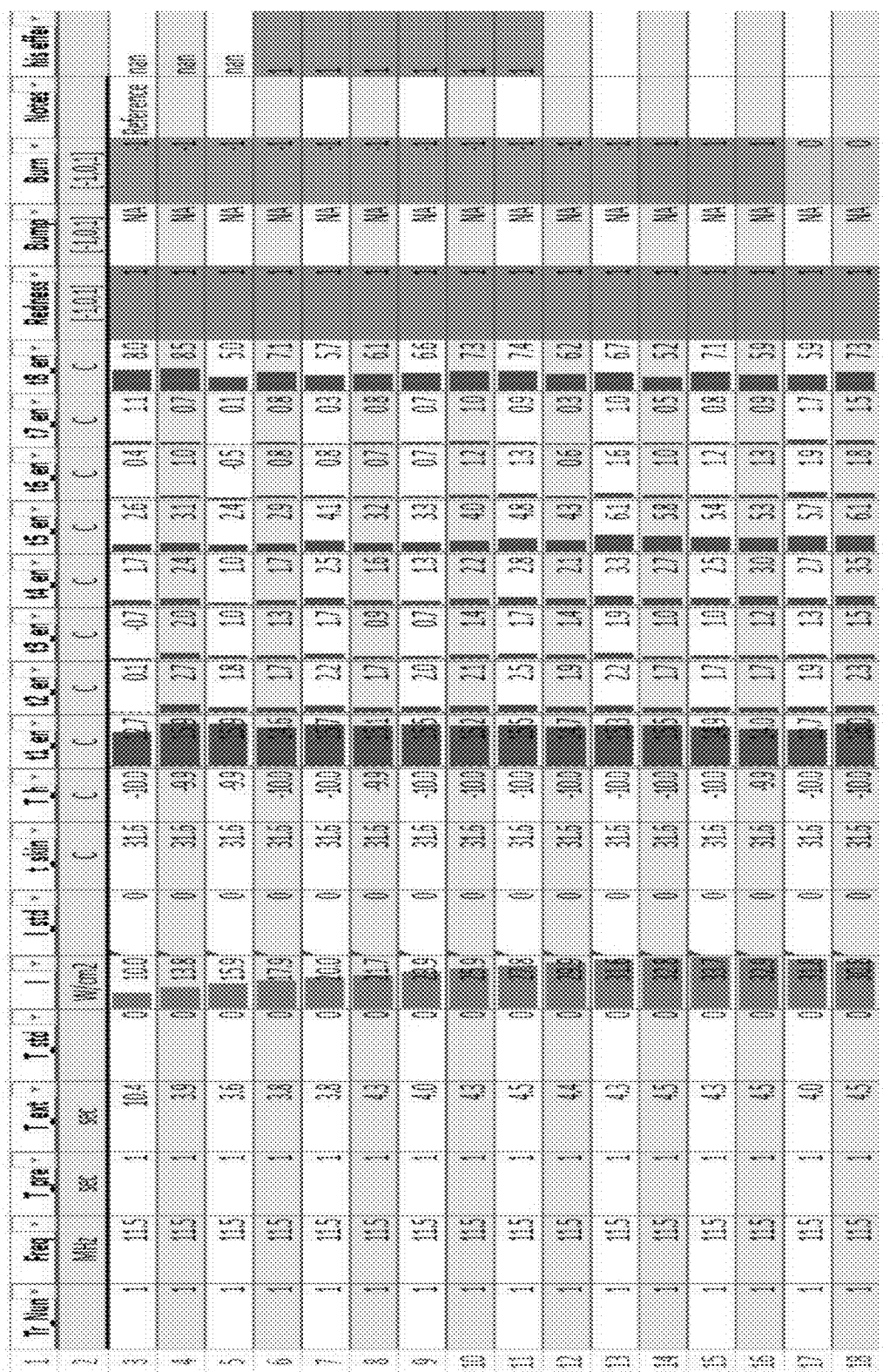
FIG. 19J1

FIG. 19J2

| Abbreviation | Meaning |
|---|---|
| Point | Treatment Point |
| Tr_Num | Tranducer number |
| Freq | Working Frequency |
| T_pre | Pre Cooling Time-Required |
| T_ext | Excitation Duration-Average |
| T_std | Excitation Duration-STD |
| I | Intensity-Average |
| I_std | Intensity-STD |
| t_skin | Skin Temperature |
| T_h | Holder Temperature |
| t1_end | End Excitation Temperature-Thermistor 1 |
| t2_end | End Excitation Temperature-Thermistor 2 |
| t3_end | End Excitation Temperature-Thermistor 3 |
| t4_end | End Excitation Temperature-Thermistor 4 |
| t5_end | End Excitation Temperature-Thermistor 5 |
| t6_end | End Excitation Temperature-Thermistor 6 |
| t7_end | End Excitation Temperature-Thermistor 7 |
| t8_end | End Excitation Temperature-Thermistor 8 |
| Redness | Redness |
| Bump | Bump |
| Burn | Epidermal Damage |
| Notes | Notes |

FIG. 19K

1 day follow-up: marked

2 day follow-up: marked

SKIN TREATMENT APPLICATOR

RELATED APPLICATIONS

This application is a Continuation of U.S. patent application Ser. No. 16/307,503 filed on Dec. 6, 2018, which is a National Phase of PCT Patent Application No. PCT/IL2017/050638 filed on Jun. 6, 2017, which claims the benefit of priority under 35 USC § 119(e) of U.S. Provisional Patent Application No. 62/345,918 filed on Jun. 6, 2016. The contents of the above applications are all incorporated by reference as if fully set forth herein in their entirety.

FIELD AND BACKGROUND OF THE INVENTION

The present invention, in some embodiments thereof, relates to treating tissue using ultrasound energy and, more particularly, but not exclusively, to an ultrasonic transducer and applicator for skin treatments.

US Publication number U.S. Pat. No. 6,595,934 B1 discloses "A method of skin rejuvenation by thermal ablation using high intensity focused ultrasound energy includes the steps of positioning an ultrasound emitting member adjacent an external surface of the skin, emitting ultrasound energy from the ultrasound emitting member into the skin, focusing the ultrasound energy in the skin, ablating the skin with the focused ultrasound energy to form an ablated tissue area below the external surface of the skin containing unablated tissue of the skin and a plurality of lesions at which the tissue of the skin is ablated, and removing the ultrasound emitting member from adjacent the external surface of the skin. The lesions cause collagen production by the skin to be stimulated. The lesions can begin and end at predetermined depths beneath the external surface of the skin so that the epidermis and the deep layer of the dermis are not damaged."

SUMMARY OF THE INVENTION

According to an aspect of some embodiments of the invention, there is provided an applicator for applying ultrasound energy to a tissue volume, comprising: an array comprising a plurality of ultrasound transducers, the transducers arranged side by side, the transducers configured to emit unfocused ultrasound energy suitable to thermally damage at least a portion of the tissue volume, each of the transducers comprising a coating thin enough so as not to substantially affect heat transfer via the coating to the tissue; and a cooling module configured to apply cooling via the transducers to prevent overheating of a surface of the tissue volume being contacted by the transducers.

In some embodiments, the coating is less than 50 μm thick.

In some embodiments, the coating is electrically insulating.

In some embodiments, the coating is thermally conductive, having a thermal conductivity coefficient between 0.1-0.3 W/m*K.

In some embodiments, the cooling module is positioned to cool a base portion of the applicator on which the transducers are mounted.

In some embodiments, the plurality of transducers are spaced apart from each other, and wherein thermal insulation exists between adjacent transducers.

In some embodiments, the cooling module comprises one or more of: a coolant and a pump configured for circulating the coolant; a thermoelectric cooler; a thermal reservoir block; and a fan.

In some embodiments, the cooling module is configured to cool at a rate high enough to overcome heating generated by the transducers.

In some embodiments, the coating is mounted on an electrode of each of the transducers by a thin uniform layer of glue.

In some embodiments, the applicator further comprises one or more temperature sensors disposed at or in proximity to the distal face and configured to indicate a temperature of one or both of an emitting surface of at least one transducer and a surface of the tissue.

In some embodiments, a thickness of each of the transducers is smaller than 1 mm.

In some embodiments, an emitting surface of each of the transducers is flat.

According to an aspect of some embodiments of the invention, there is provided an ultrasound transducer, comprising: a piezo element comprising top and bottom electrodes; an electrically conductive element in contact with the top electrode; a substrate layer on which the bottom electrode is mounted, the substrate layer comprising no more than 10% electrically conductive material in volume, the electrically conductive material sufficient for conducting electrical current to the bottom electrode.

In some embodiments, the substrate layer comprises at least 10 electrically conductive elements dispersed in an electrically insulating matrix, such that at least 90% of a surface area of the bottom electrode is in contact with the electrically insulating matrix, and less than 10% of a surface area of the bottom electrode is in contact with the electrically conductive elements; the less than 10% distributed across a total surface area of the bottom electrode.

In some embodiments, the substrate has a thickness smaller than 100 microns.

In some embodiments, the substrate is mounted on an electrically conductive layer, the electrically conductive layer mounted on an isolating layer, and the isolating layer is mounted on a base.

In some embodiments, the 10% of the surface area contacting the electrically conductive elements is in the form of a plurality of contact points between the bottom electrode and the electrically conductive elements.

In some embodiments, the electrically conductive elements comprise one or both of particles and fibers, the electrically conductive elements occupying between 1-20% of a total volume of the substrate.

In some embodiments, the substrate comprises a thermal conductivity lower than 0.5 [W/(m*K)].

In some embodiments, the piezo element is shaped to produce a substantially trapezoidal beam having an opening angle between 5-15 degrees.

According to an aspect of some embodiments of the invention, there is provided a flexible applicator for applying ultrasound energy to tissue, comprising: an array of flat piezo elements aligned along a long axis, with spaces defined in between adjacent elements; the array disposed in between two layers of flexible film such that the film layers contact opposing surfaces of each of the piezo elements, at least one of the film layers comprising electrical circuitry configured to excite the piezo elements; wherein each of the piezo elements is thin enough and narrow enough so as to reduce interference with flexure of the applicator, the piezo elements being spaced enough from each other so that a film portion in between them can be flexed.

In some embodiments, the flexible applicator further comprises one or more temperature sensors mounted on the flexible film, the temperature sensors configured to indicate at least one of a temperature of a surface of the tissue and a temperature of the piezo element.

In some embodiments, the electrical circuitry is printed on an inner side of the layer facing the piezo element.

According to an aspect of some embodiments of the invention, there is provided a method of applying ultrasound energy to tissue using an array of ultrasound transducers, comprising: selecting a first frequency so that an ultrasound beam emitted by at least a first transducer of the array is effective to heat tissue at least 1 mm deep; selecting a second frequency so that an ultrasound beam emitted by at least a second transducer of the array is effective to heat a surface of the tissue; and exciting the at least two transducers at the frequencies to control heating of the treated tissue.

In some embodiments, at least one transducer is excited at a resonance frequency and at least one second transducer is excited at a frequency which is two folds the resonance frequency.

In some embodiments, the second transducer is excited at a frequency between 5%-20% lower than a resonance frequency of the second transducer to reduce an efficiency of the transducer for raising a temperature of the transducer's emitting surface.

According to an aspect of some embodiments of the invention, there is provided a method for thermal ablation of skin tissue, comprising: selecting parameters of unfocused ultrasound suitable to produce a plurality of spaced apart thermal damage lesions at the dermis layer, the lesions separated by non-damaged tissue, while maintaining a temperature of the epidermis between 5-40 degrees Celsius; and emitting unfocused ultrasound at the selected parameters while not causing thermal damage to the epidermis.

In some embodiments, the parameters of the unfocused ultrasound are selected to generate thermal damage in a layer at a depth of 0.5-5 mm from the epidermis.

In some embodiments, emitting comprises heating tissue in the lesions to a temperature between 50-80 degrees C.

In some embodiments, the method comprises targeting fibrotic tissue while having low or no effect on fat tissue.

In some embodiments, the method further comprises, prior to the emitting, positioning one or more ultrasound transducers configured to emit the unfocused ultrasound energy in contact with the epidermis, and exciting the transducers according to the selected parameters.

In some embodiments, maintaining comprises cooling the epidermis by cooling a base on which the one or more transducers are mounted, the cooling being transferred via the transducers to the epidermis.

In some embodiments, the method comprises producing cylindrical thermal damage lesions.

In some embodiments, the spaced apart thermal damage lesions are connected by a thermally damaged region that extends between them.

In some embodiments, the method further comprises collecting feedback on the treatment by measuring a temperature of a surface of the tissue and/or a temperature of the one or more transducers.

In some embodiments, the method further comprises collecting feedback on a position of the transducers relative to the tissue surface.

In some embodiments, feedback is collected by measuring an electric power consumption of the one or more transducers.

In some embodiments, feedback is collected by measuring the gain of one or more amplifiers associated with the one or more transducers.

In some embodiments, feedback is collected by measuring a capacitance of the one or more transducers and/or a capacitance between adjacent transducers.

In some embodiments, the method further comprises collecting feedback on the treatment by measuring bio impedance of the tissue.

According to an aspect of some embodiments of the invention, there is provided a method of selectively producing a desired effect on tissue using ultrasound, comprising: selecting a target tissue layer; applying ultrasound to heat tissue of the target tissue layer only to a level that produces the desired effect, without causing substantial thermal damage to other tissue layers.

In some embodiments, the desired effect is a short term effect visible at 1 hour post treatment or earlier, and wherein a duration of applying ultrasound is selected to produce the desired short term effect.

In some embodiments, applying ultrasound comprises applying ultrasound to a level that heats the tissue enough to cause inflammation.

In some embodiments, the effect is a long term effect visible after 3 weeks or more post treatment.

In some embodiments, applying ultrasound is to a level that heats the tissue enough to induce generation of collagen and/or elastin.

In some embodiments, the method comprises selecting an energy intensity higher than 8 W/cm^2 and lower than 40 W/cm^2.

In some embodiments, the method comprises raising an energy intensity to increase a time period throughout which the desired effect lasts.

According to an aspect of some embodiments of the invention, there is provided a method for combining injection treatment and ultrasound treatment, comprising: selecting ultrasound energy parameters suitable to thermally damage a tissue layer deeper than the dermis; applying the ultrasound energy to the tissue; and applying injection treatment to the thermally damaged tissue layer or to tissue adjacent the thermally damaged tissue layer, such that injecting is facilitated due loosening of connective tissue caused by the applying of ultrasound energy.

According to an aspect of some embodiments of the invention, there is provided an ultrasound applicator configured of assessing contact with the skin, comprising: an array comprising a plurality of ultrasound transducers, the transducers arranged side by side, the transducers configured to emit unfocused ultrasound energy suitable to thermally damage at least a portion of the tissue volume; a plurality of temperature sensors positioned intermediate adjacent ultrasound transducers; and a controller configured to receive an indication of temperature from the temperature sensors and to assess contact between one or more of the plurality of ultrasound transducers with the skin according to the indication.

According to an aspect of some embodiments of the invention, there is provided an ultrasound applicator configured of assessing contact with the skin, comprising: an array comprising a plurality of ultrasound transducers, the transducers arranged side by side, the transducers configured to emit unfocused ultrasound energy suitable to thermally damage at least a portion of the tissue volume; a controller configured to receive an indication related to transducer behavior and to assess contact between one or more of the plurality of ultrasound transducers with the skin according to the indication.

According to an aspect of some embodiments of the invention, there is provided an ultrasound transducer, comprising: a piezo element comprising top and bottom electrodes; an electrically conductive element in contact with the top electrode; a substrate layer on which the bottom electrode is mounted, the substrate layer comprising at least 10 electrically conductive elements dispersed in an electrically insulating matrix, such that at least 90% of a surface area of the bottom electrode is in contact with the electrically insulating matrix, and less than 10% of a surface area of the bottom electrode is in contact with the electrically conductive elements; the less than 10% distributed across a total surface area of the bottom electrode.

In some embodiments, the substrate comprises a thickness smaller than 100 microns.

In some embodiments, the substrate is mounted on an electrically conductive layer.

In some embodiments, the electrically conductive layer is mounted on an isolating layer, and the isolating layer is mounted on a base.

In some embodiments, a total thickness of the transducer is smaller than 1 mm.

In some embodiments, the substrate is resilient enough to reduce interference with vibration of the piezo element.

In some embodiments, the 10% of the surface area contacting the electrically conductive elements is in the form of a plurality of contact points between the bottom electrode and the electrically conductive elements.

In some embodiments, the electrically conductive elements comprise one or both of particles and fibers, the electrically conductive elements occupying between 1-20% of a total volume of the substrate.

In some embodiments, the electrically insulating matrix comprises polymer material.

In some embodiments, the substrate is resilient enough to reduce interference with vibration of the piezo element.

In some embodiments, the substrate comprises a thermal conductivity lower than 0.5 [W/(m*K)].

In some embodiments, the piezo element is flat.

In some embodiments, the piezo element is shaped to produce a substantially trapezoidal beam having an opening angle between 5-15 degrees.

According to an aspect of some embodiments of the invention, there is provided a flexible applicator for applying ultrasound energy to tissue, comprising an array of flat piezo elements aligned along a long axis, with spaces defined in between adjacent elements; the array disposed in between two layers of flexible film such that the film layers contact opposing surfaces of each of the piezo elements, at least one of the film layers comprising electrical circuitry configured to excite the piezo elements; wherein each of the piezo elements is sized to be small enough so as not to interfere with flexure of the applicator.

In some embodiments, the flexible film comprises polyimide.

In some embodiments, the system further comprises one or more temperature sensors coupled to the flexible film, the temperature sensors configured to indicate at least one of a temperature of a surface of the tissue and a temperature of the piezo element.

In some embodiments, the electrical circuitry is printed on an inner side of the layer facing the piezo element.

In some embodiments, the first frequency is selected so that an ultrasound beam emitted by the first transducer is effective to heat tissue at least 1 mm deep, and wherein the second frequency is selected so that an ultrasound beam emitted by the second transducer is effective to heat a surface of the tissue. Alternatively, the first frequency is selected so that an ultrasound beam emitted by the first transducer is effective to heat tissue at least 1 mm deep, and the second frequency is selected so that an ultrasound beam emitted by the second transducer is effective to heat tissue deeper than 1 mm (as measured relative to the tissue surface).

In some embodiments, at least one transducer is excited at a resonance frequency and at least one second transducer is excited at a frequency which is two folds the resonance frequency.

In some embodiments, the method further comprises measuring a temperature of a surface of the tissue and modifying the frequencies according to the temperature.

In some embodiments, controlling the heating of the tissue further comprises powering the first transducer at a first power level and the second transducer at a second power level.

In some embodiments, an efficiency of the first transducer is higher than an efficiency of the second transducer.

In some embodiments, the second transducer is excited at a frequency between 5%-20% lower than a resonance frequency of the second transducer to reduce an efficiency of the transducer for raising a temperature of the transducer's emitting surface.

According to an aspect of some embodiments of the invention, there is provided a system for applying ultrasound to tissue, comprising an array of a plurality of ultrasound transducers, the array shaped and sized for contacting the tissue; a controller configured to excite, concurrently, at least two transducers out of the plurality of transducers at different frequencies to control heating of the treated tissue to reduce thermal damage to a surface of the tissue; wherein the different frequencies comprise at least first and second frequencies, the second frequency being at least 10% higher or at least 10% lower than the first frequency.

In some embodiments, the transducers are aligned side by side and define a substantially flat surface configured to contact the tissue.

According to an aspect of some embodiments of the invention, there is provided an applicator for applying ultrasound energy to a tissue volume, comprising: an array comprising a plurality of ultrasound transducers, the transducers arranged side by side and spaced apart from each other by thermal insulation, the transducers configured to emit unfocused ultrasound energy suitable to thermally damage at least a portion of the tissue volume; and a cooling module configured to regulate a temperature of the transducers to reduce thermal damage to a surface of the tissue volume.

In some embodiments, the array is configured on a distal face of the applicator, the distal face shaped and sized to contact a surface of the tissue volume.

In some embodiments, the thermal insulation comprises air.

In some embodiments, the cooling module comprises a coolant and a pump configured for circulating the coolant.

In some embodiments, the cooling module comprises one or more of: a thermoelectric cooler; a thermal reservoir block; and a fan.

In some embodiments, one or more of the plurality of transducers are configured to receive echo signals reflected by the tissue in response to ultrasound emission by the transducers.

In some embodiments, the applicator further comprises one or more temperature sensors disposed at or in proximity to the distal face and configured to indicate a temperature of one or both of an emitting surface of at least one transducer and a surface of the tissue.

According to an aspect of some embodiments of the invention, there is provided a method for thermal ablation of skin tissue, comprising: emitting unfocused ultrasound to produce a plurality of spaced apart thermal damage lesions at the dermis layer, the lesions separated by non-damaged tissue, while maintaining a temperature of the epidermis between 5-40 degrees Celsius.

In some embodiments, parameters of the unfocused ultrasound are selected to generate thermal damage in a dermis layer at a depth of 0.5-3 mm from the epidermis.

In some embodiments, emitting comprises heating tissue in the lesions to a temperature between 60-70 degrees C.

In some embodiments, the unfocused energy is effective to target fibrotic tissue while having low or no effect on fat tissue.

In some embodiments, the method further comprises, prior to the emitting, positioning one or more ultrasound transducers configured to emit the unfocused ultrasound energy in contact with the epidermis.

In some embodiments, maintaining comprises cooling the epidermis by cooling an emitting surface of the one or more transducers.

In some embodiments, the thermal damage lesions are cylindrical.

In some embodiments, the method further comprises collecting feedback on the treatment by measuring a temperature of the tissue.

In some embodiments, the method further comprises collecting feedback on the treatment by measuring bio impedance of the tissue.

In some embodiments, the bio impedance is assessed by having one or more ultrasound transducers used for the emitting stimulate the tissue.

According to an aspect of some embodiments of the invention, there is provided a method of manufacturing an array of a plurality of ultrasonic transducers, comprising: providing an elongated piezoelectric plate; constructing an elongated transducer by mounting one or more layers onto the piezoelectric plate; dicing the elongated transducer into a plurality of separately operable ultrasonic transducers.

In some embodiments, the plurality of ultrasonic transducers are substantially identical in thickness.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a block diagram of a system for applying ultrasound to tissue, according to some embodiments;

FIG. 2 is a flowchart of applying ultrasound energy to tissue while controlling heating of the tissue surface, according to some embodiments;

Figure 1:
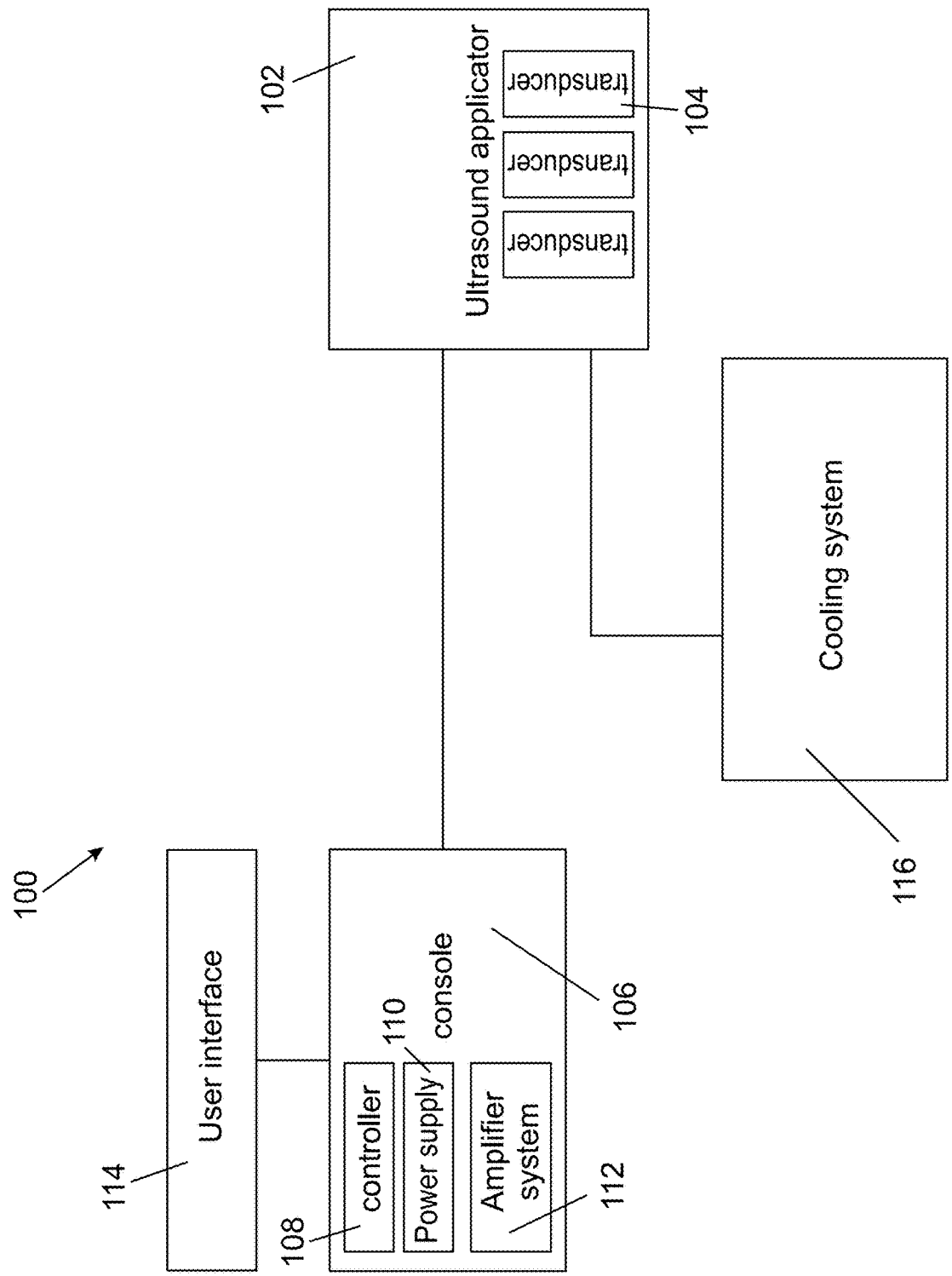
Figure 4:
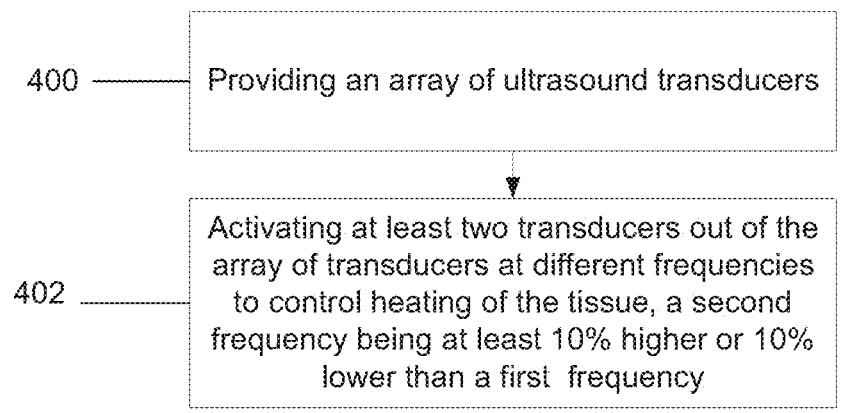
Figure 5:
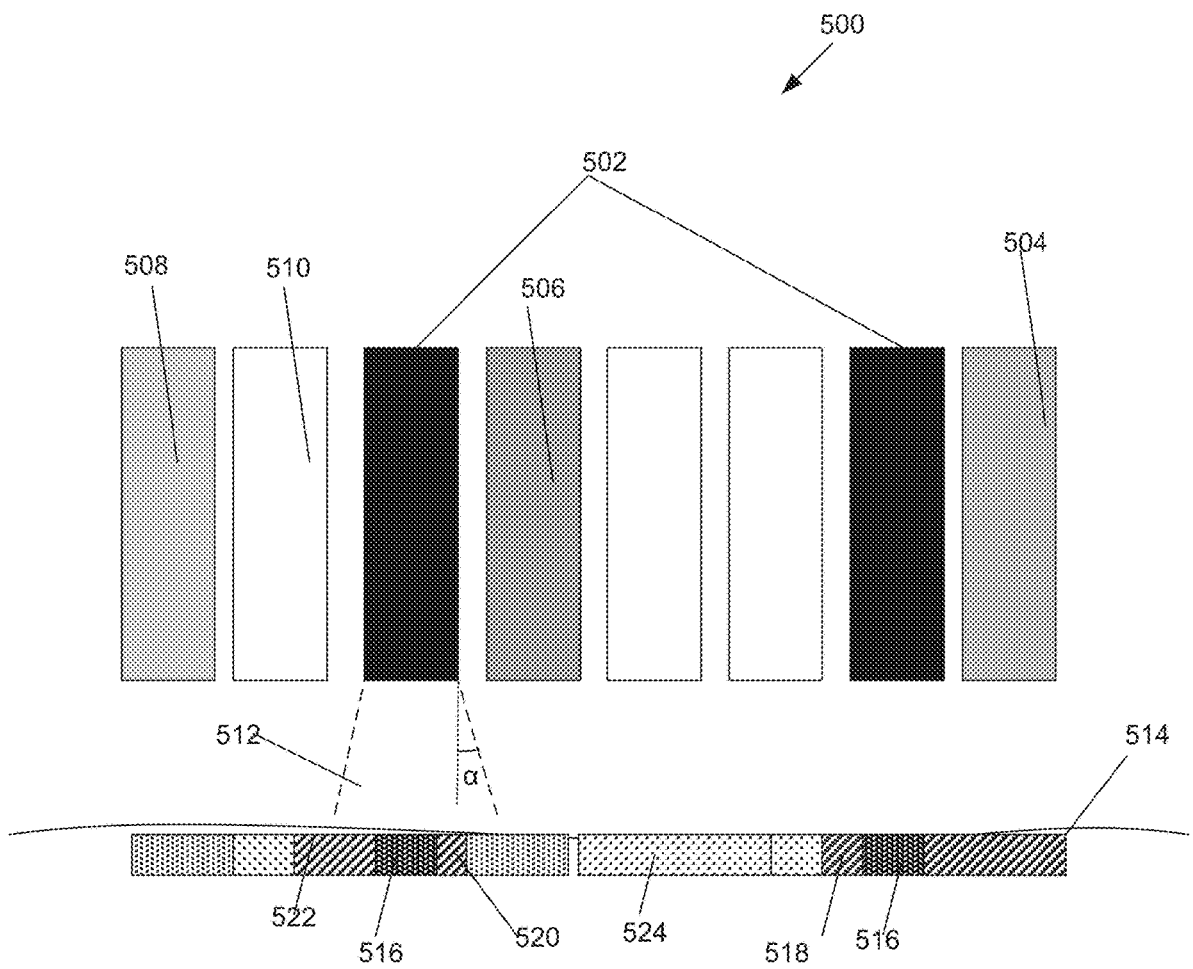
Figure 6:
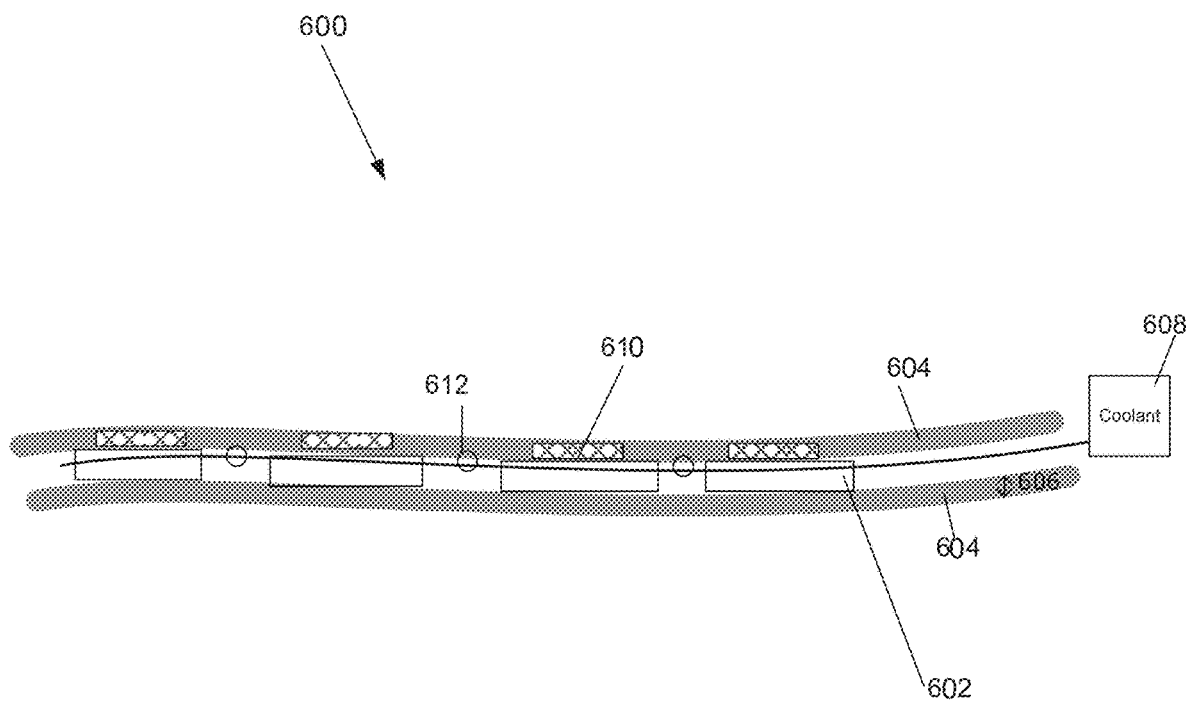
Figure 7:
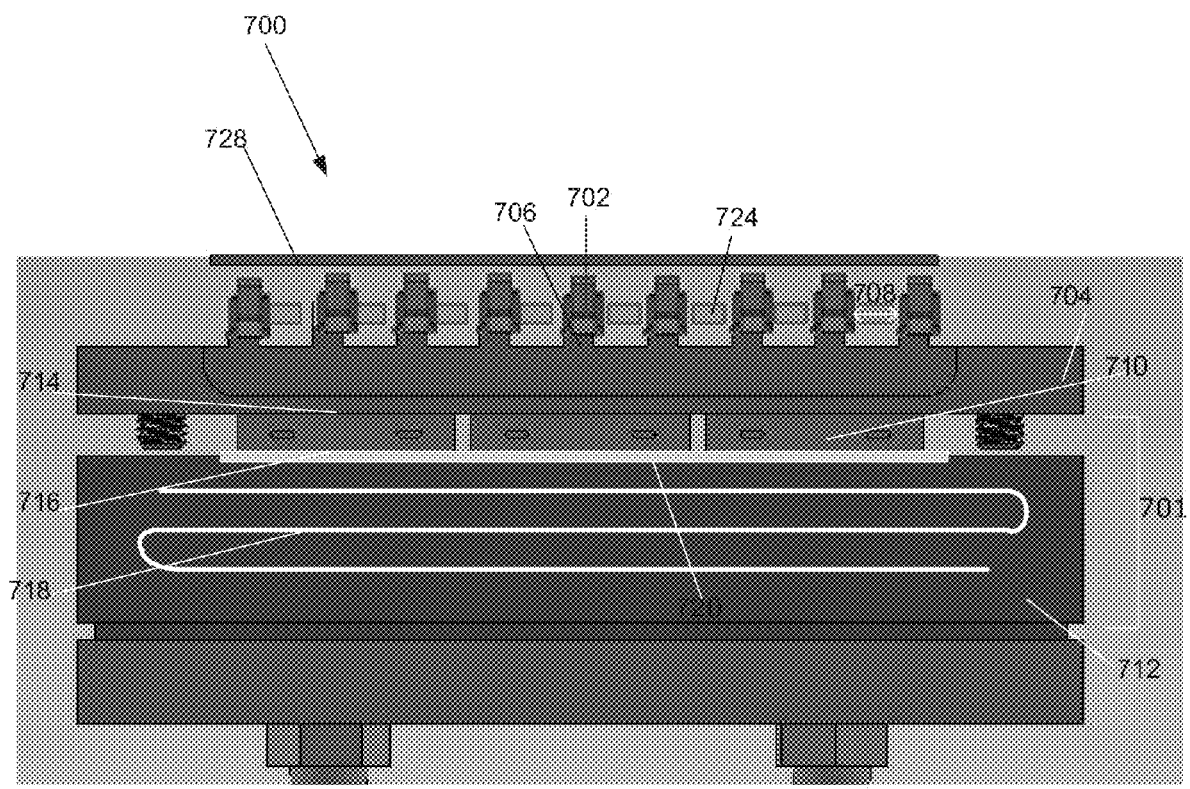
Figure 8A:
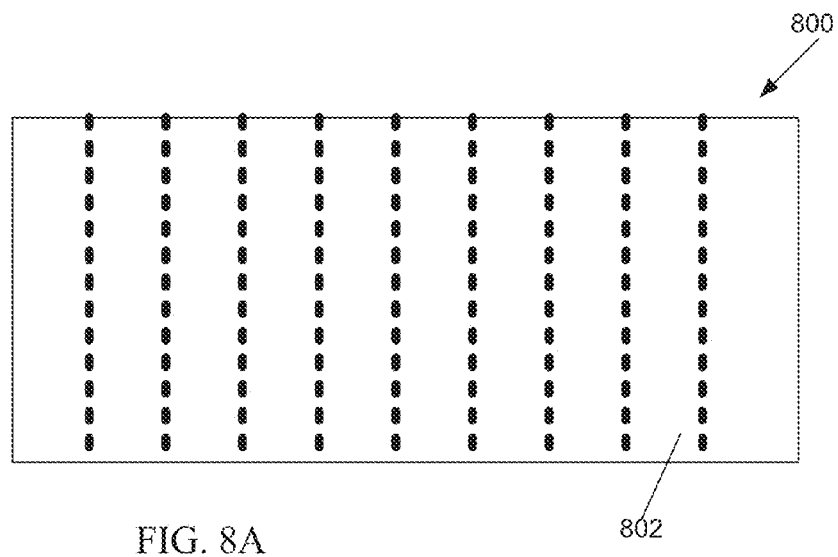
Figure 8B:
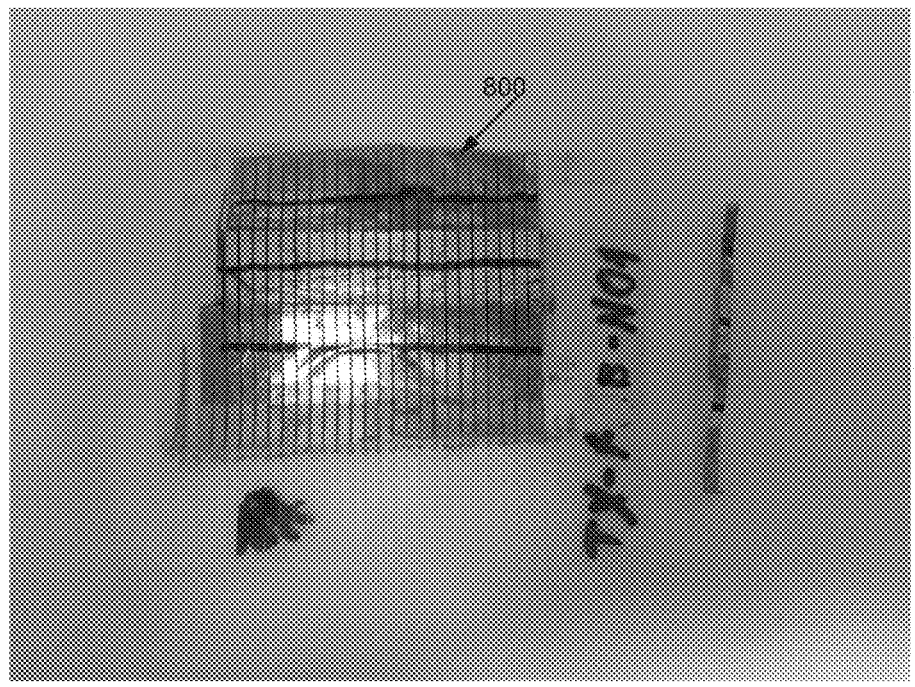
Figure 8C:
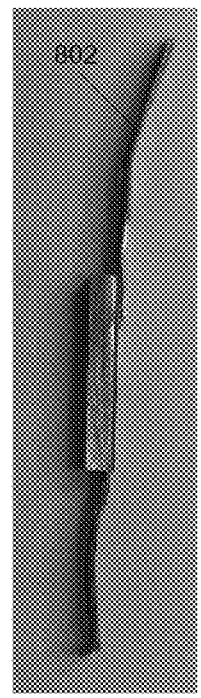
Figure 10:
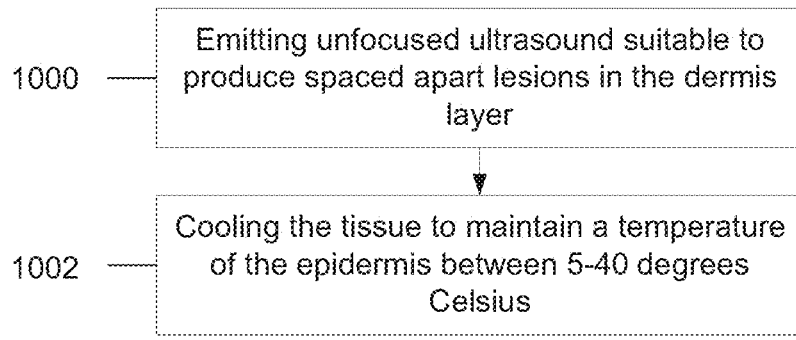
Figure 11:
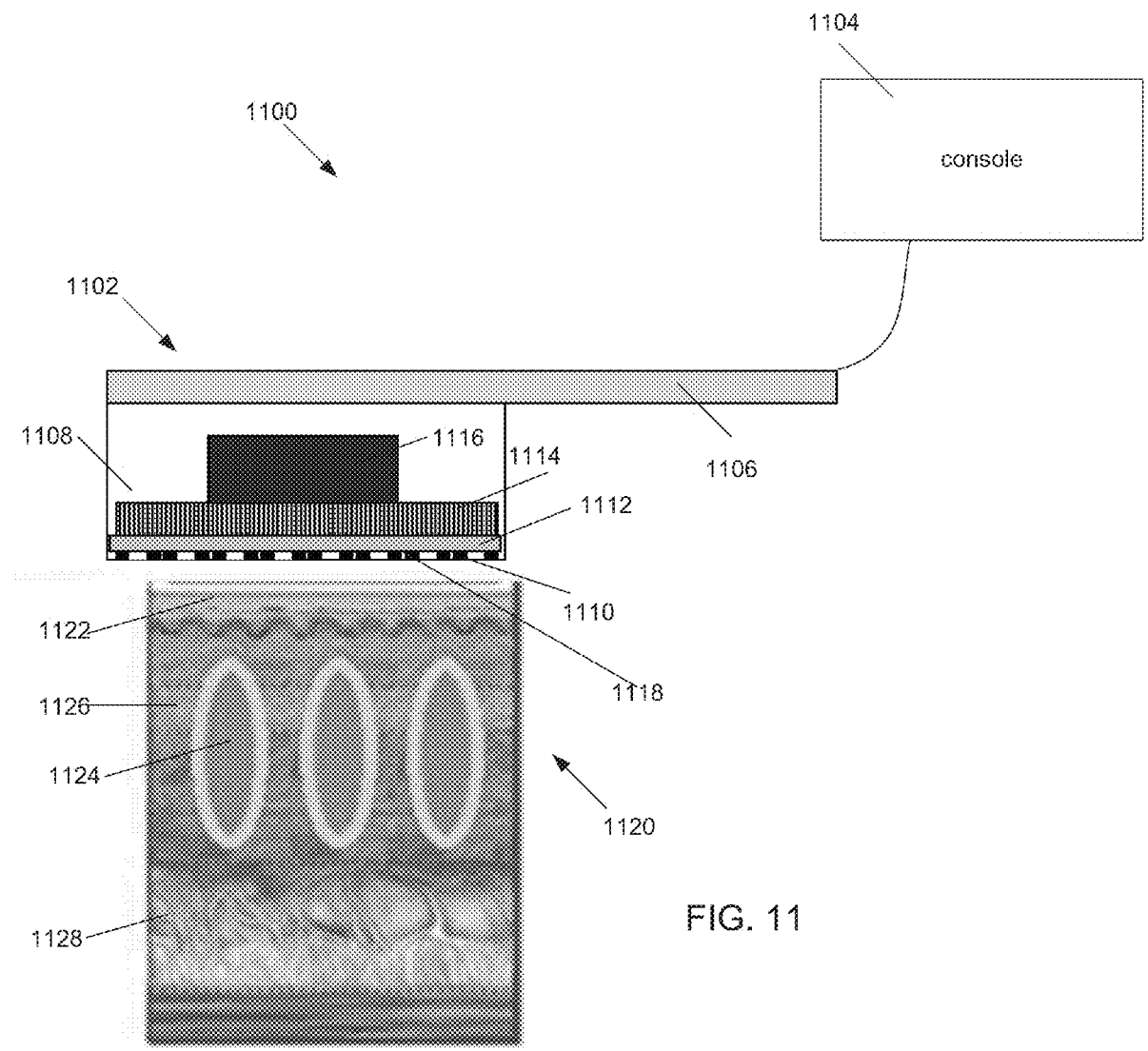
Figure 13A:
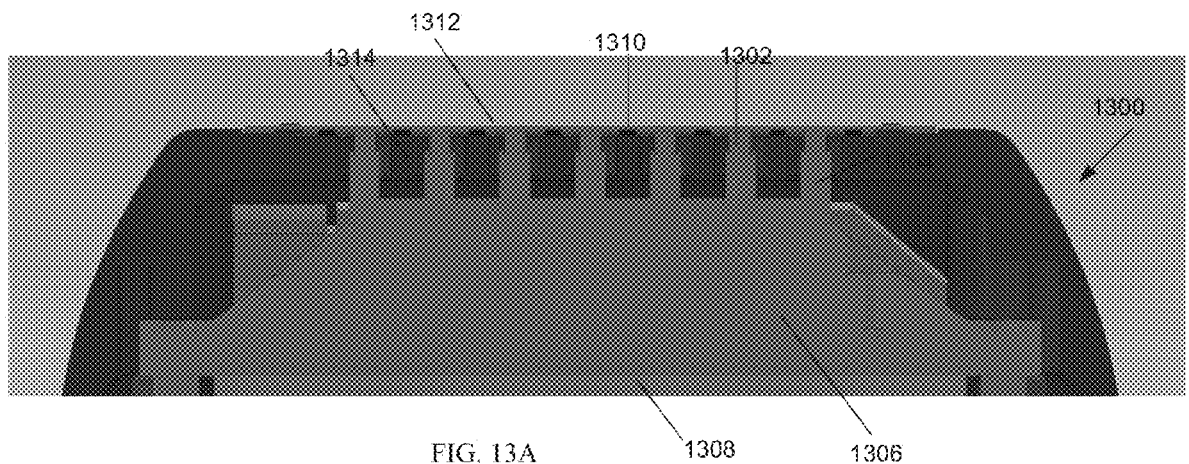
Figure 13B:
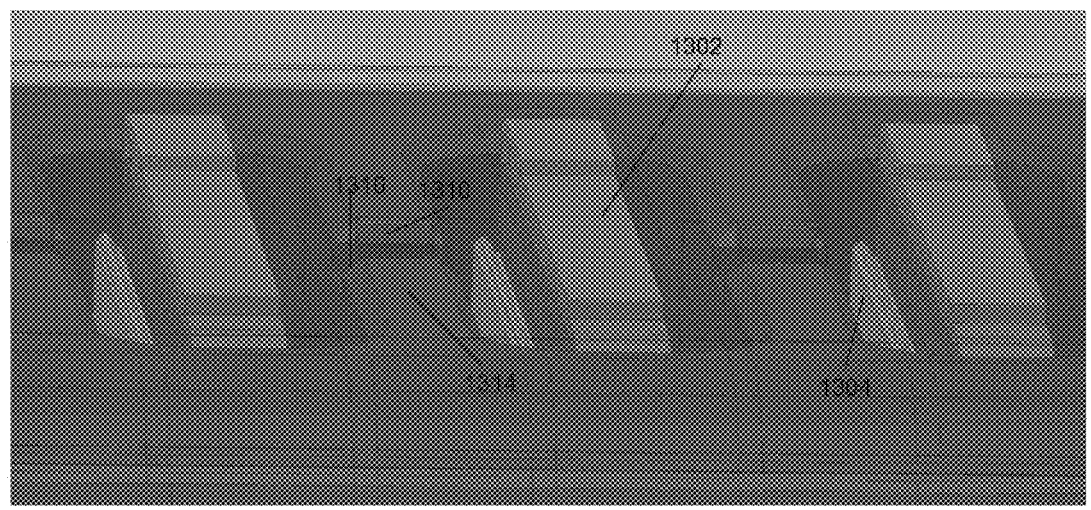
Figure 15A:
Figure 15B:
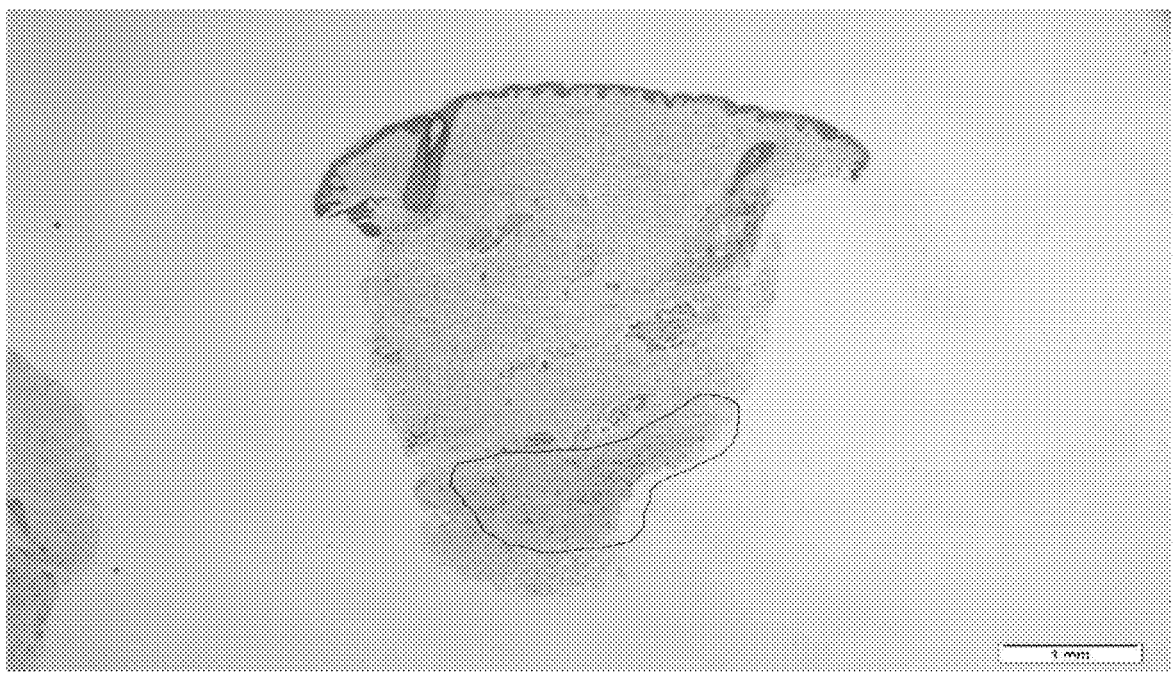
Figure 16A:
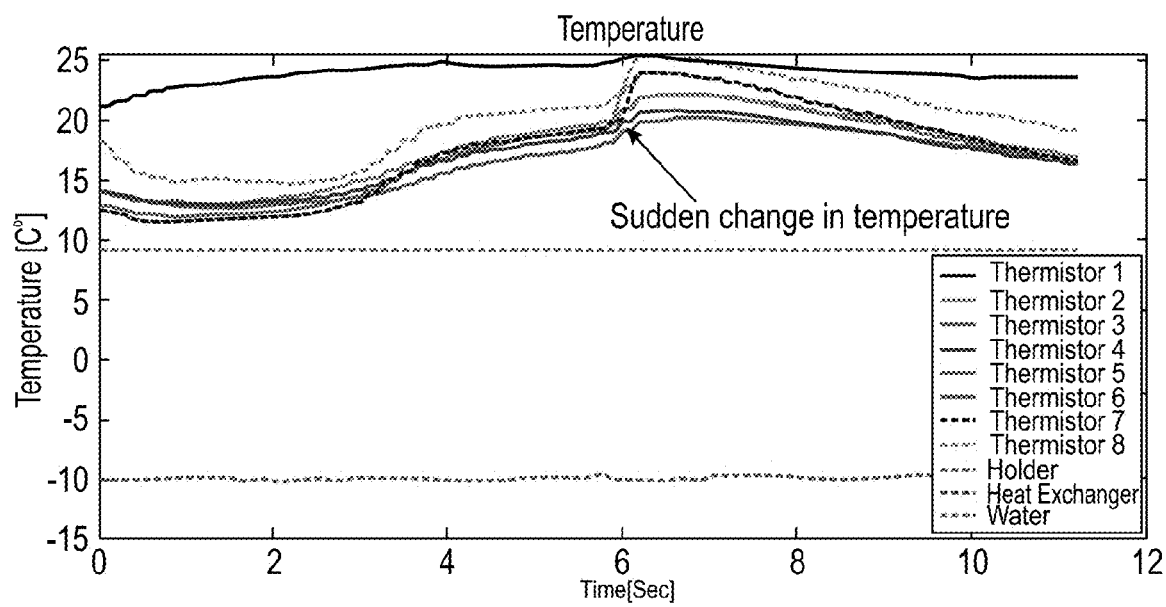
Figure 17A:
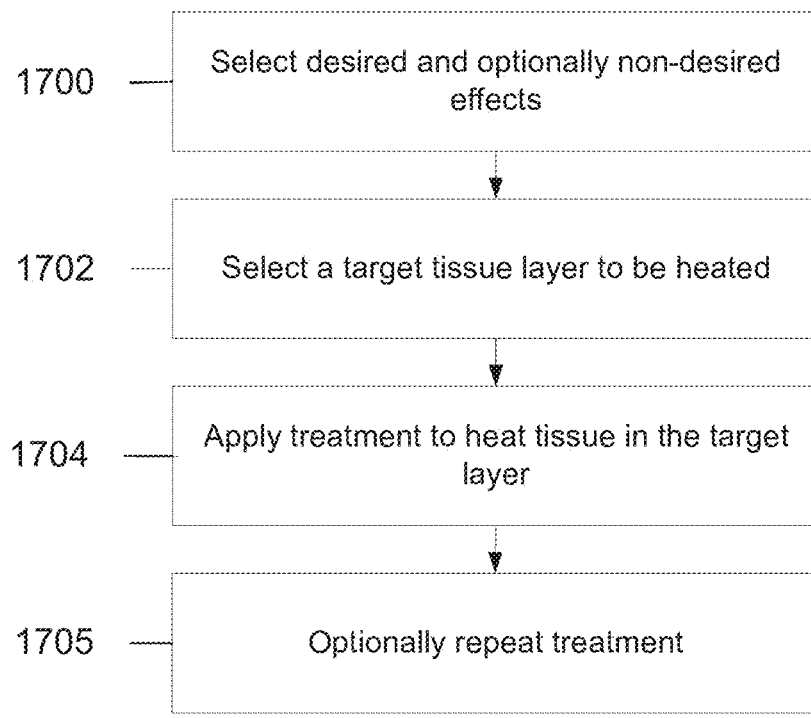
Figure 17B:
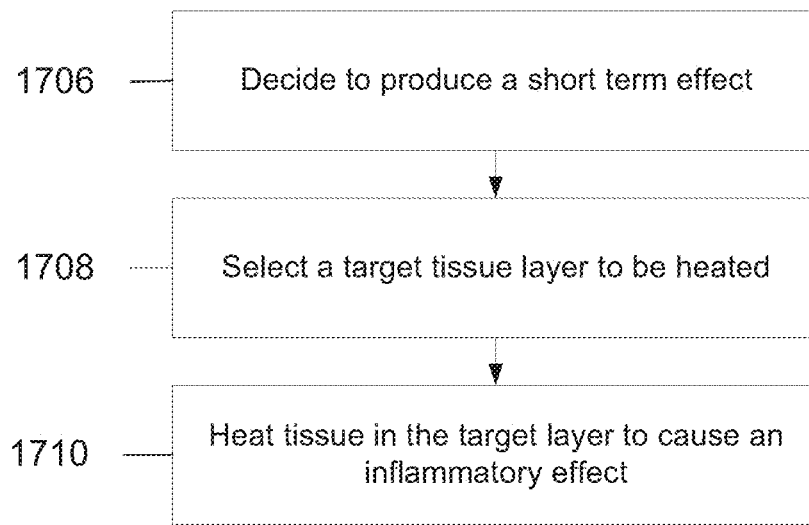
Figure 17C:
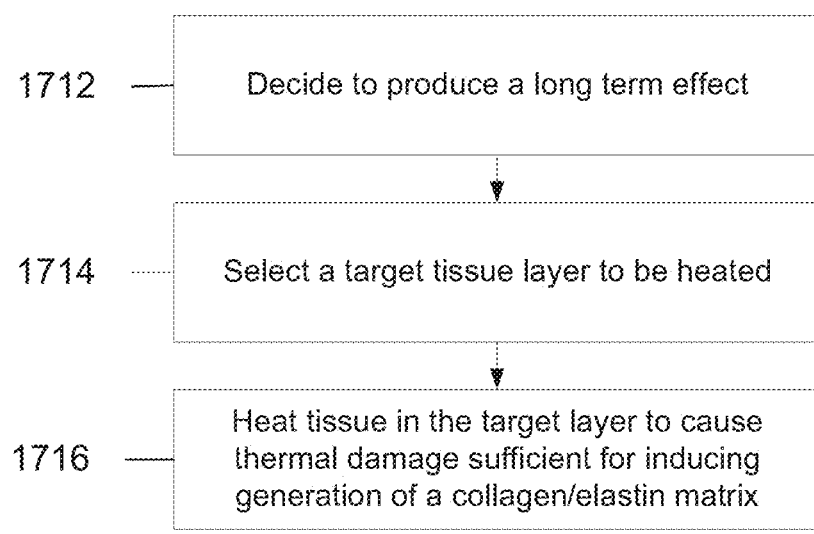
Figure 18:
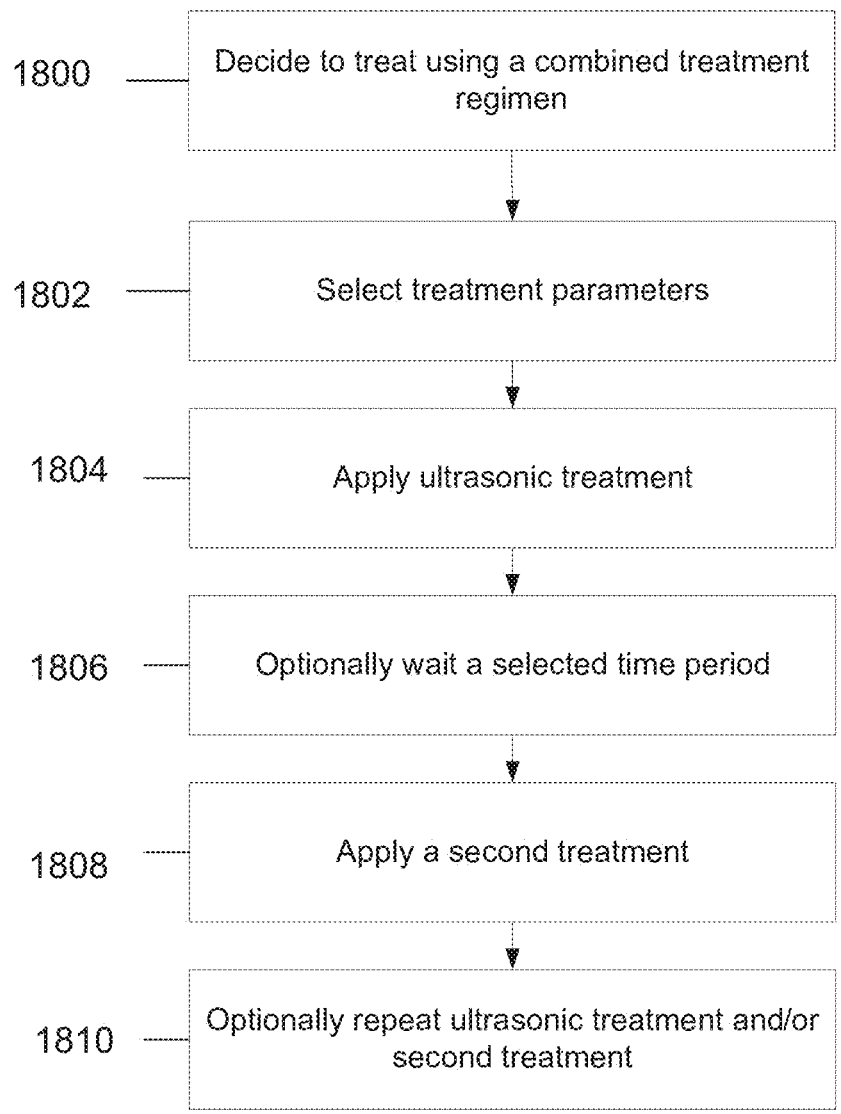
Figure 20A:
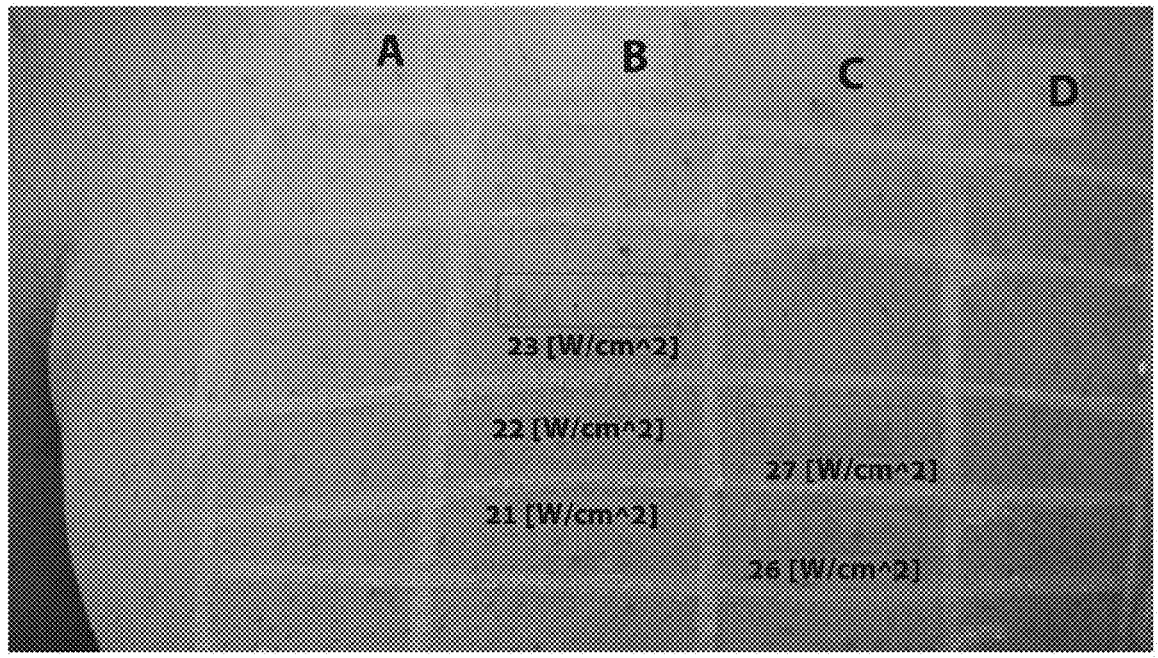
Figure 20B:
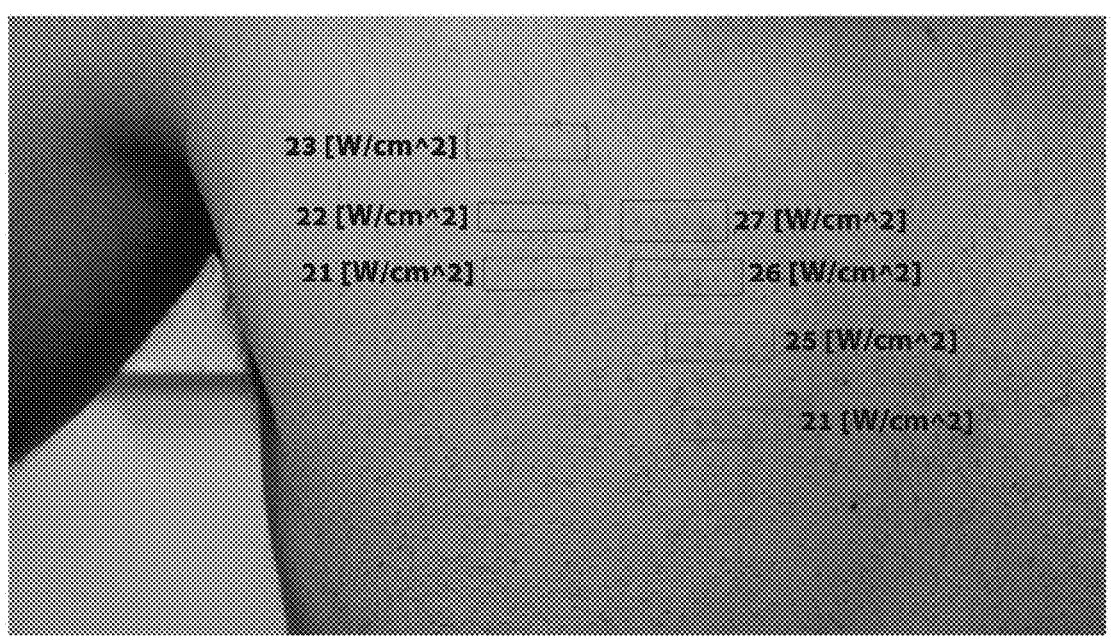
Figure 21:
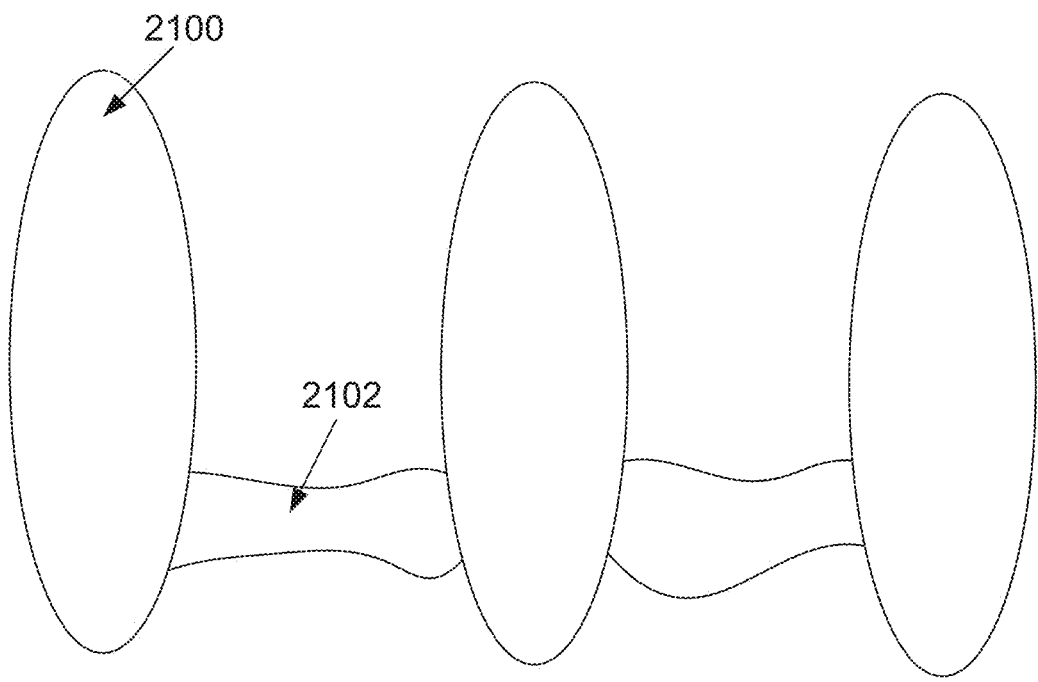
Figure 22:
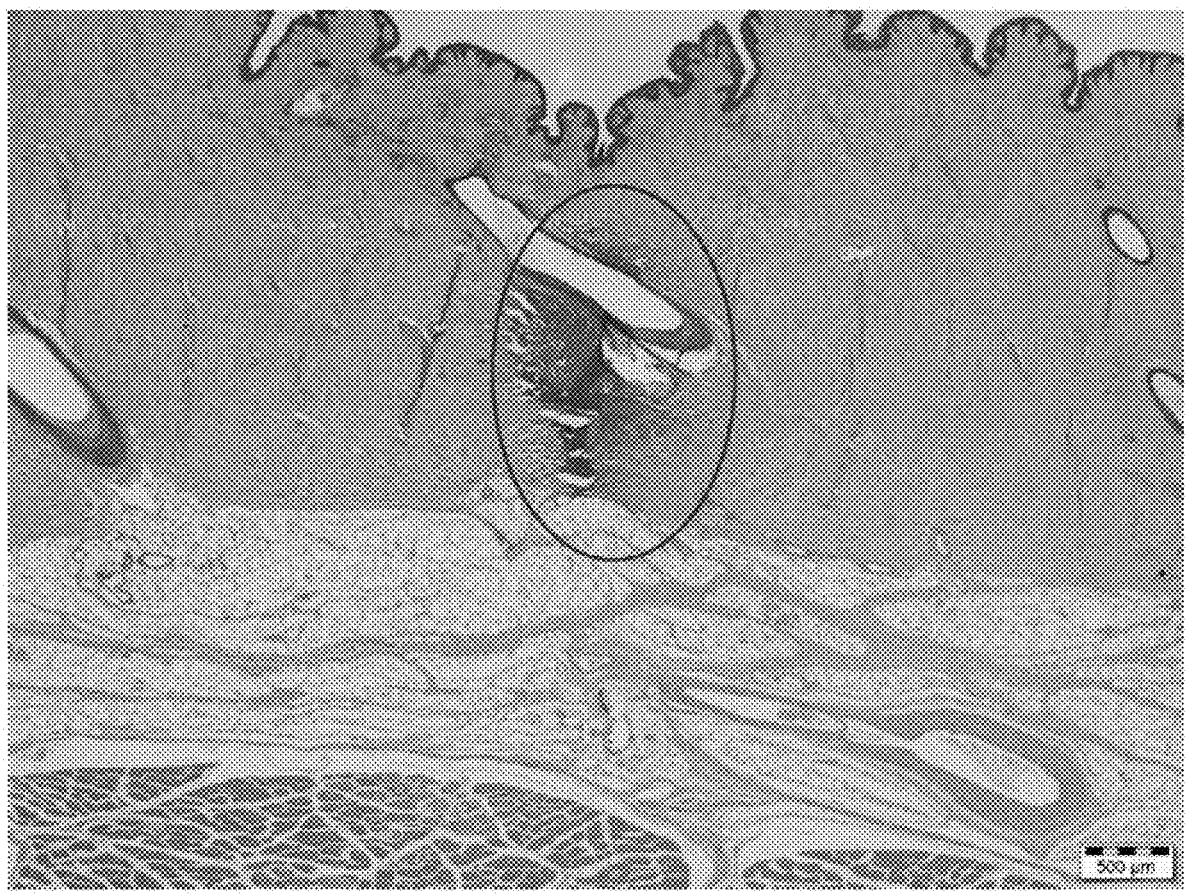

FIGS. 3A-F are cross section views of various structures of an ultrasound transducer, according to some embodiments;

FIG. 4 is a flowchart of a method for activating an array of ultrasound transducers, according to some embodiments;

FIG. 5 schematically illustrates activation of an array of ultrasound transducers at various frequencies, and a thermal effect on tissue surface being treated by the transducers, according to some embodiments;

FIG. 6 illustrates a flexible ultrasound applicator comprising an array of ultrasound emitting elements sandwiched between film layers, according to some embodiments;

FIG. 7 is an exemplary configuration of an ultrasound applicator comprising a cooling module, according to some embodiments;

FIGS. 8A-C illustrate a large continuous ultrasonic transducer construct processed to form an array of separate transducers, according to some embodiments;

FIGS. 9A-B are exemplary graphs of activation of an array of ultrasound transducers, according to some embodiments;

FIG. 10 is a flowchart of a method for cosmetic ultrasound skin treatment, according to some embodiments;

FIG. 11 is a schematic diagram of a system for ultrasound skin treatment, according to some embodiments;

FIGS. 12A-F are schematic isotherms representing a temperature distribution in the tissue following applying of different energy types and/or different energy parameters, according to some embodiments;

FIGS. 13A-B are a side view and an enlarged view of an ultrasound applicator head, according to some embodiments;

FIGS. 14A-D are histopathology slides obtained in a swine cadaver model during an experiment performed in accordance with some embodiments of the invention;

FIGS. 15A-B are histopathology slides obtained in-vivo in human skin during an experiment performed in accordance with some embodiments of the invention;

FIGS. 16A1-J illustrate various methods for assessing contact between the applicator and the skin, according to some embodiments;

FIGS. 17A-C are flowcharts of methods for obtaining a desired effect, including short term effects (see FIG. 17B) and/or long term effects (see FIG. 17C), according to some embodiments;

FIG. 18 is a flowchart of a method for combining ultrasonic treatment and a second treatment, according to some embodiments;

FIGS. 19A-L are various results obtained in a live swine model experiment, performed in accordance with some embodiments;

FIGS. 20A-B are photographs of treated human skin at 1 and 2 days post treatment;

FIG. 21 is a schematic illustration showing a contiguous damage effect on tissue, according to some embodiments of the invention; and FIG. 22 is a histopathology image showing ablation of hair follicles, according to some embodiments of the invention.

DESCRIPTION OF SPECIFIC EMBODIMENTS OF THE INVENTION

The present invention, in some embodiments thereof, relates to treating tissue using ultrasound energy and, more particularly, but not exclusively, to an ultrasonic transducer and applicator for skin treatments.

A broad aspect of some embodiments relates to treating tissue using unfocused ultrasound, while optionally cooling at least a portion of the tissue to reduce thermal damage to the tissue surface and/or other tissue layers. Some embodiments relate to controlled heating of tissue. Optionally, heat is applied to the tissue by an applicator comprising a plurality of transducers configured to emit unfocused ultrasound energy, the applicator comprising a cooling module configured to cool at least a surface of the tissue (e.g. skin) by applying cooling via the transducers that come in contact with the skin. In some embodiments, the extent of heating and/or cooling are controlled to obtain thermal damage at a selected depth relative to the tissue surface. In some embodiments, a structure and/or size (e.g. thickness) and/or materials of the transducer are selected to optimize heat transfer, such as heat transfer from the emitting surface of the transducer to the tissue and/or heat transfer from a cooling module of the applicator, via the transducer, to the tissue. An aspect of some embodiments relates to a thin ultrasound transducer for applying ultrasound to tissue, in which an ultrasound emitting element is mounted on a substrate comprising no more than 10% electrically conductive material in volume, dispersed within the substrate. In some embodiments, at least 80%, at least 90%, at least 95% or intermediate, higher or smaller percentage of the substrate volume comprises electrically insulating material. In some embodiments, a bottom electrode of the ultrasound emitting element is mounted on the substrate, and electrical current for exciting the emitting element is conducted via the electrically conductive material of the substrate. In some embodiments, the electrically conductive material is in the form of a plurality of elements, such as a plurality of particles and/or fibers, disposed in a matrix of insulating material (for example a polymer matrix).

In some embodiments, the ultrasound emitting element is mounted on the substrate such that at least 80%, at least 90%, at least 95% of a surface area of the bottom electrode contacts the insulating material of the substrate. In some embodiments, less than 10%, less than 5%, less than 2% of the bottom electrode surface comes in contact with the electrically conductive material dispersed within the substrate. In some embodiments, electrical contact is distributed across the mating surfaces of the bottom electrode and the substrate, such that the contact points are spaced apart from each other, randomly and/or in a predefined pattern.

A potential advantage of a substrate comprising electrically conductive elements occupying only a small (e.g. less than 10%) volume of the total volume of the substrate may include providing a layer which is resilient enough to reduce interference with vibration of the ultrasound emitting element (e.g. due to the polymer matrix), yet electrically conductive. This may provide an advantage over, for example, a layer that is fully or mostly composed of electrically conductive material (e.g. comprising more than 60%, more than 80%, more than 90% electrically conductive material in volume), which may impose a higher resistance to vibration. Another potential advantage may include providing a spatially-spread electrical contact, which may allow a more uniform distribution, for example as opposed to using a local contact, such as via a wire.

In some embodiments, a thickness of the substrate is selected so that an efficiency of the transducer, which is affected by damping provided by the transducer layers, is not lower than 40%, not lower than 30%, not lower than 20% or intermediate, higher or lower efficiencies. In some embodiments, a thickness of the substrate is selected so that the rate of heat transfer from the emitting element towards the tissue is at least 1 W/(m^2K), at least 1.5 W/(m^2K), at least 3 W/(m^2K). Optionally, a thickness of the substrate is between 10-30, between 20-80 microns, between 1-100 microns or intermediate, higher or lower thicknesses.

In some embodiments, the transducer comprises a layer structure in which a plurality of thin layers are arranged in a "sandwich" structure in which they are mounted one on top of the other. In some embodiments, the layer structure comprises, for example, an ultrasound emitting element having top and bottom electrodes; an electrically conductive element in contact with the top electrode; a substrate underlying the bottom electrode; and an electrically conductive layer or base underlying the substrate. In some embodiments, a total thickness of the transducer is less than 1 mm, less than 1.5 mm, less than 0.7 mm or intermediate, larger or smaller size.

In some embodiments, at least a distal face of the transducer is configured to come in contact with the tissue, directly and/or via a thin coating disposed on the transducer. In some embodiments, the distal face of the transducer comprises a substantially flat geometry. Optionally, a thickness of the coating layer that separates a distal emitting face of the transducer from the tissue being contacted is less than 50 μm, less than 100 μm, less than 25 μm or intermediate, higher or lower thicknesses. A potential advantage of a thin coating may include reducing interference with ultrasonic energy transmission, as absorption of the energy in the coating remains low, yet providing an electrical isolation between the transducer and the tissue surface. In some embodiments, the thickness is selected in accordance with a working frequency of the transducer. In some embodiments, a thickness of the coating is low enough so that cooling applied via the transducer can be passed on to the tissue surface being contacted. Optionally, the coating is formed of a material that provides for minimal thermal resistance. In some embodiments, a thermal conductivity coefficient of the coating material is high enough to allow transfer of heat (and/or cooling) from the transducer surface to the tissue surface. Optionally, a thermal conductivity coefficient of the coating is between 0.1-0.3 W/m*K, 0.5-0.8 W/m*K, 0.05-0.2 W/m*K or intermediate, higher or lower ranges. In an example, the coating comprises polymide having a thermal conductivity coefficient of 0.12 W/m*K.

An aspect of some embodiments relates to an applicator configured to apply unfocused ultrasound to a tissue volume while maintaining the tissue surface cool enough to reduce or prevent thermal damage to the tissue surface. In some embodiments, the applicator comprises an array of ultrasonic transducers arranged side by side on a ribbed frame with thermal isolation between the transducers.

Optionally, thermal isolation is achieved by spacing the transducers apart such that air and/or other material isolates between them.

In some embodiments, the transducers and/or tissue surface contacting the applicator are actively cooled, for example by a thermo electric cooler (TEC) element used in conjunction with a heat exchanger, and/or by circulation of fluid such as water and/or antifreeze and/or by a gas. Additionally or alternatively, the transducers and/or tissue surface are passively cooled, for example by a thermal reservoir block (e.g. a cooled block of copper).

In some embodiments, cooling is applied to prevent over heating of the transducer. Additionally or alternatively, cooling is applied to reduce a temperature of the tissue surface. Optionally, cooling of the tissue surface is achieved via the applicator, for example by cooling the transducer's emitting surface to a temperature lower than a current temperature of the tissue surface. Cooling may be applied to the tissue before, during and/or after applying energy.

In some embodiments, the transducer is selected to be thin enough so as to provide for cooling of the tissue via the transducer. Optionally, using a thin ultrasound emitting element, e.g. a PZT plate having a thickness between 90-250 microns, allows for cooling of the tissue surface via the transducer, even when high intensity and/or high frequency ultrasound energy is emitted by the transducer. As the resonance frequency of the PZT plate is determined by a thickness of the plate, a potential advantage of using a thin plate may include the ability to use high frequencies, for example between 8-22 MHz. In some embodiments, cooling is applied to the tissue to control or limit energy dissipation inside the tissue.

In some embodiments, the applicator comprises one or more temperature sensors (e.g. thermistors and/or thermocouples) configured to indicate a temperature of the one or more transducers and/or to indicate a temperature of the tissue, e.g. of the tissue surface. Optionally, cooling is controlled in accordance with temperature feedback provided by the one or more temperature sensors. In some embodiments, one or more temperature sensors are configured to indicate a temperature of the frame carrying the transducers. In some embodiments, one or more temperature sensors are configured to indicate a temperature of a heat exchanger and/or other components of the applicator's cooling system.

An aspect of some embodiments relates to a flexible applicator for applying ultrasound energy to tissue, comprising one or more ultrasound emitting elements sandwiched between two layers of flexible film (e.g. Kapton). In some embodiments, the emitting elements are arranged side by side. In some embodiments, electrical circuitry configured for activating the emitting elements is embedded and/or printed on an inner side of one or both of the film layers, facing the emitting elements. Optionally, the circuitry comprises thermoresistors configured for indicating a temperature of the tissue and/or a temperature of the emitting elements.

In some embodiments, the applicator can be flexed to be positioned on non-flat tissue surfaces, such as on the forehead and/or around the neck. Optionally, each of the ultrasound emitting elements is narrow enough so as to reduce interference with bending, folding and/or otherwise shaping the flexible applicator. In some embodiments, the emitting elements are spaced enough from each other so that a flexible film portion in between them remains wide enough to be bent or otherwise flexed, enabling moving one element with respect to its adjacent element.

An aspect of some embodiments relates to controlling a thermal effect on tissue at located different depths. In some embodiments, a first thermal effect is produced on tissue located at a first depth, and a second thermal different than the first thermal effect is produced on tissue located at a second depth, different from the first depth. Some embodiments relate to controlling a thermal effect on a tissue surface by exciting adjacent ultrasound transducers at different frequencies. In some embodiments, at least two transducers are excited, a first transducer at a frequency suitable for producing thermal damage to deeper tissue layers of the tissue and a second transducer at a frequency suitable for locally heating the tissue surface, the second frequency being at least 10% or at least 10% lower than the treating frequency of the first transducer.

In some embodiments, one or more transducers are excited at treatment frequencies (e.g. between 9-22 MHz), while one or more other transducers, for example transducers positioned in between the treating transducers, are excited at a frequency different than the treatment frequency (for example activated at a frequency which is twofold the resonance frequency) to produce sufficient heat for avoiding over-cooled tissue surface regions (overcooling may occur in tissue regions which are contacted by the actively cooled applicator, but are not contacted by the treating transducers). Alternatively, the non-treating transducers are not activated. Optionally, when not activated, the transducers are effective to cool the tissue surface in the vicinity of the heating transducers. In some cases, heating of the tissue surface is obtained by using relatively low power energy, optionally applied over a longer duration, for example as compared to high power which may result in undesired non-linear effects.

In some embodiments, the different frequencies are selected in accordance with ultrasound attenuation in the tissue. Optionally, increasing the frequency results in faster energy absorption in the tissue, such that the tissue layers closer to the emitting element are heated more than deeper tissue layers.

Additionally or alternatively to using different frequencies, the thermal effect is controlled by setting powering of the transducers, for example so that the second transducer (e.g. non-treating transducer)'s efficiency is relatively low, producing heating of the emitting element as a byproduct of activation which in turn heats the tissue surface. In some embodiments, heating (e.g. of the tissue surface) is provided by a heating element, for example a heating element mounted a tissue facing portion of the applicator.

An aspect of some embodiments relates to treating tissue by targeting a tissue layer and/or a tissue type located at a selected depth with respect to a surface of the tissue. Some embodiments relate to treating skin (e.g. to cause tightening of the skin) by producing controlled thermal damage at a depth of between 1-3 mm from the epidermis, using unfocused ultrasound energy.

In some embodiments, the unfocused ultrasound energy is applied to produce multiple spaced apart thermal damage lesions in the tissue, for example in the reticular dermis layer of the skin. In some embodiments, the lesions are substantially cylindrical. Alternatively, the lesions are of a different geometry, or optionally arbitrary shaped. A potential advantage of forming spaced-apart lesions may include that non-damaged tissue between lesions may promote healing by generating growth of elastin and/or collagen fibers. In some embodiments, use of unfocused ultrasound enables producing a repeatable spatial lesion pattern. A potential advantage of unfocused ultrasound may include covering a relatively wide surface area, reducing a need for repetitive movement of the applicator and potentially obtaining a more uniform distribution of the damage, for example as compared to use of focused ultrasound.

In some embodiments, a thermally damaged region extends between the spaced apart lesion and optionally connects the regions. For example, a thermally damaged layer of connective tissue (e.g. fat tissue) may extend between two or more cylindrical lesions produced in the reticular dermis of the skin, extending for example at the bottom of the lesions.

In some embodiments, the unfocused energy selectively targets fibrotic tissue (e.g. collagen fibers), while its effect on other types of tissue such as fat and/or connective tissue is relatively small since a sensitivity of these tissue types to the applied heat is reduced relative to the sensitivity of the fibrotic tissue, so that fat forms a natural barrier to the thermal damage.

In some embodiments, treatment parameters are selected for obtaining a desired effect. In an example of parameter selection, an intensity of the emitted ultrasound is selected to be between 8-40 W/cm^2, between 12-22 W/cm^2, between 10-17 W/cm^2, between 14-18 W/cm^2 to produce thermal damage in the dermis yet avoid damage to the epidermis; or, for example, above 22 W/cm^2 to produce thermal damage in the dermis and in the epidermis, if such is desired. In some embodiments, selection of intensity should be correlated with the excitation duration and/or other parameters such as the extent of active cooling applied. In an example, intensities listed above are applied over a 4 second excitation duration, along with active cooling of the transducer base to a temperature of −10 degrees Celsius. Other examples of treatment parameters include a duration of treatment, a number of repetitions, excitation frequency, a number of activated transducers, and/or others. In some embodiments, treatment parameters are selected to obtain damage at a selected depth, such as between 0.5 to 5 mm from the epidermis. In some embodiments, treatment parameters are selected to obtain lesions of a specific size or geometry, for example lesions having a length of 1-4 mm.

Some embodiments relate to a system for aesthetic treatment, comprising an ultrasound applicator for example as described herein, a console and/or a user interface. In some embodiments, the applicator is configured to be moved across a surface of the skin (e.g. facial skin). In some embodiments, the system is configured to receive input, such as input pertaining to a desired effect, and to automatically select treatment parameters for obtaining that effect.

An aspect of some embodiments relates to manufacturing an array of a plurality of independently operable ultrasound transducers from a large transducer construct. In some embodiments, one or more layers are mounted on a continuous PZT plate to form a large transducer construct, and the construct is then is diced and/or otherwise processed to form an array of transducers.

In some embodiments, the continuous PZT plate comprises a porous PZT.

An aspect of some embodiments relates to assessing contact between one or more transducers of the applicator and the tissue (e.g. the skin). In some embodiments, one or more parameters relating to transducer behavior (e.g. power consumption, impedance, temperature, and/or others) are assessed for determining contact.

In some embodiments, a temperature of the one or more transducers (or associated with the one or more transducers) is monitored, and a change in temperature, in value and/or trend (e.g. a rise above a threshold) is indicative of loss of contact.

In some embodiments, a level of power applied to the one or more transducers for activation is monitored, and a change in the consumed power, in value and/or trend (e.g. a rise above a threshold) is indicative of loss of contact.

In some embodiments, capacitance is measured between upper electrodes of adjacent transducers or between upper and lower electrodes of the same transducer, and a change in capacitance, in value and/or trend is indicative of loss of contact.

In some embodiments, when loss of contact is detected (either partial or full loss of contact), activation of the transducers is automatically ceased. In some embodiments, when loss of contact is detected, the applicator is repositioned on the surface of the tissue. A potential advantage of monitoring contact between the one or more transducers and the tissue may include reducing a risk of burn out of the transducer. Another potential advantage may include reducing a risk of unwanted damage to the tissue, such as damage caused by an overheated transducer which was overheated due to loss of contact with the tissue.

An aspect of some embodiments relates to obtaining a desired effect on the tissue (and optionally avoiding non-desired effects) by targeting a tissue layer to be heated. In some embodiments, a tissue layer is targeted and heated while other tissue layers and/or tissue located sideways (i.e. on a horizontal axis) remain substantially unaffected.

Desired effects include, for example, one or more of smoothing out wrinkles; reducing a visibility of stretch marks; evening out skin complexion and/or other effects.

In some embodiments, the effects comprise short term effects, long term effects, or a combination of both.

In some embodiments, treatment parameters are selected for producing a short term effect, such as one that is visible as soon as several minutes or several hours post treatment. In some embodiments, the treatment parameters are selected for producing a short term effect that lasts at least 6 hours, at least 1 day, at least 3 days, at least 1 week or intermediate longer or shorter time periods. Additionally or alternatively, the treatment parameters are selected for producing a long term effect, such as one that is visible only at 3 weeks post treatment, 2 months post treatment, 6 months post treatment or intermediate, longer or shorter time periods. In some embodiments, the treatment parameters are selected for producing a long term effect that lasts at least 1 month, at least 3 months, at least 1 year, at least 5 years or intermediate, longer or shorter time periods.

In some embodiments, a short term effect is obtained substantially without damaging a surface of the tissue. In some embodiments, a short term effect is obtained without a long term effect. In some embodiments, obtaining of short term effects is associated with a thermal damage sufficient to cause an inflammatory effect, including for example edema, irritation, swelling and/or others. Optionally, the thermal damage is limited only to an extent that results in inflammation but does not induce long term effects such as fibroblast penetration and/or substantial inducing of collagen and/or elastin generation.

In some embodiments, obtaining of long term effects is associated with a higher extent of thermal damage, such as one that induces generation of collagen and/or elastin and/or a general healing reaction. In some embodiments, a deeper tissue layer is targeted for obtaining a long term effect as compared to a layer that would be targeted for obtaining a short term effect.

In some embodiments, the system is configured to receive as input one or more of: a desired effect, a non-desired effect, a timing of the effect (e.g. short term or long term), a time period over which the effect should last, and/or other input, and to automatically select treatment parameters suitable for obtaining that effect. For example, the system selects parameters suitable for targeting a specific tissue layer while avoiding damage to other layers.

An aspect of some embodiments relates to combining ultrasonic treatment with one or more additional aesthetic treatments, such as filler injection treatment, topical cremes, neuro-toxin injection (BOTOX) and/or other treatments. In some embodiments, ultrasound treatment is applied as preparation for a second treatment. In some embodiments, ultrasound treatment affects the tissue in a manner that facilitates applying the second treatment. Additionally or alternatively, the two treatments work together for obtaining an effect, optionally an effect that cannot be obtained by each treatment separately. Optionally, applying both treatments obtains a desired effect in a time shorter than would have been required if each of the treatments was applied alone.

In an example, in the case of filler injection, ultrasound can be applied to cause loosening of connective tissue which may facilitate the process of injection; in another example, ultrasound is applied to thermally damage tissue at or adjacent a site of injection, for example to induce generation of a new collagen/elastin matrix.

Some embodiments relate to a method for obtaining an immediate visible effect on skin, comprising determining a time by which an effect should be visible; and applying heating to tissue underlying the epidermis, without thermally damaging the epidermis, less than 24 hours before the determined time. In some embodiments, unfocused ultrasound is applied by contacting said skin. In an exemplary application, a subject is treated in order to prepare for an event occurring on the same day or a day after. Optionally, the effect lasts over 1 day, 2 days, 5 days, 1 week or intermediate, longer or shorter time periods.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Referring now to the drawings, FIG. 1 is a block diagram of a system for applying ultrasound to tissue, according to some embodiments.

In some embodiments, system 100 comprises an ultrasound applicator 102, configured for applying ultrasound energy to tissue, such as skin. In some embodiments, applicator 102 comprises a handle operable by a clinician, such as a physician or a nurse.

In some embodiments, applicator 102 comprises one or more ultrasound emitting elements, such as one or more ultrasound transducers 104. In an example, applicator 102 comprises an array of ultrasound transducers, for example comprising 5 transducers, 7 transducers, 9 transducers, 12 transducers or intermediate, larger or smaller number of transducers.

In some embodiments, system 100 comprise a console 106. In some embodiments, console 106 comprises a controller 108. In some embodiments, controller 108 is configured to control operation of the system, for example controlling emission of ultrasound energy by applicator 102. In some embodiments, the controller comprises a memory which stores, for example, setup data, records of previous treatments, and/or others. In some embodiments, In some embodiments, console 106 comprises one or more components for operating the system, for example including power supply 110 (and/or connection to an external power source), an amplifier system 112 and/or other components such as an oscilloscope. In some embodiments, console 106 is portable, for example placed on a cart. In some embodiments, console 106 comprises a user input module. Optionally, a user (e.g. physician) inserts one or more of: treatment parameters, patient data, desired and/or non desired treatment effects, and the controller selects one or more of: treatment parameters, a tissue layer to be targeted, a number of treatments, timing of treatments and/or treatment duration according to the inserted input.

In some embodiments, system 100 comprises a user interface 114 for receiving input from a user such as a physician and/or for providing information to the user. In some embodiments, user interface 114 is configured for receiving operation parameters, for example including energy parameters such as frequency, intensity, and/or usage parameters such as treatment duration. In some embodiments, user interface 114 is configured to receive patient data (e.g. age, weight, height, gender, medical condition, and/or other patient related data). Optionally, user interface 114 is configured to automatically select a treatment regimen in accordance with the patient parameters.

In some embodiments, user interface 114 comprises a display. In some embodiments, user interface comprises a computer such as a laptop or a tablet computer.

In some embodiments, system 100 comprises a cooling system 116. In some embodiments, cooling system 116 is configured to cool one or more portions of applicator 102, for example configured for cooling transducers 104. Additionally or alternatively, cooling system 116 is configured to cool a tissue surface to which the energy is applied, for example cooling tissue being contacted by the applicator and/or surrounding tissue.

In some embodiments, cooling system 116 comprises a circulating coolant in the form of liquid and/or gas, for example water or antifreeze fluid. Optionally, circulation is actuated by a pump.

In some embodiments, cooling system 116 comprises an active cooling element, such as a thermoelectric cooler. In some embodiments, cooling system 116 comprises a fan. In some embodiments, a chiller is used for cooling the liquid and/or gas.

Additionally or alternatively, cooling system 116 comprises a passive cooling element, such as a thermal reservoir block, for example a copper block. Optionally, the copper block is precooled to a temperature sufficient to provide cooling of the transducers and/or the tissue surface throughout the treatment.

In some embodiments, cooling system 116 is coupled to applicator 102. In some embodiments, cooling system 116 is an inherent component of applicator 102.

In some embodiments, system 100 is activated to emit ultrasound energy towards the treated tissue. In some embodiments, the ultrasound energy is non-focused energy. Alternatively, in some embodiments, the ultrasound energy is focused.

In some embodiments, parameters of the emitted energy are selected to produce a thermal damage effect in the treated tissue. In some embodiments, the parameters are selected to achieve a certain extent of damage (e.g. dimensions of the damaged tissue volume) and/or a certain level of damage (e.g. minor damage, intermediate damage, strong damage) and/or a certain location of damage.

In some embodiments, transducers 104 are cooled by cooling system 116 to control a thermal effect on the tissue, for example to reduce thermal damage (e.g. necrosis, protein denaturation, and/or blood thrombosis) to the tissue surface.

In some embodiments, a thickness of a transducer 104 is selected to be low enough so that the transducer is efficiently cooled by the cooling system. In some embodiments, the transducer cools the tissue surface it comes in contact with.

A potential advantage of a thin transducer may include improved resistance to breakage, for example breakage caused by thermal stresses resulting from strong cooling applied before, after and/or during excitation of the transducer.

In some embodiments, each transducer is configured to be excited independently of the other transducers. In some embodiments, amplifier system 112 comprises a separate power amplifier for each of the transducers.

Alternatively, two or more transducers are configured to be excited together.

Optionally, the transducers are connected in a parallel configuration.

Alternatively, the transducers are connected in a serial combination.

Alternatively, the transducers are connected in a combination of serial and parallel sets.

In some embodiments, the circuitry comprises one or more electrical components (e.g. resistors, coils and/or capacitors) for controlling powering of each of the transducers, for example by setting an impedance on a branch leading to one of the transducers.

In some embodiments, the applicator is wirelessly activated. Optionally, the applicator is battery powered. In some embodiments, the battery is charged via a charging station and/or by wireless induction (e.g. using electromagnetic radiation).

In some embodiments, the applicator is portable.

Figure 2:
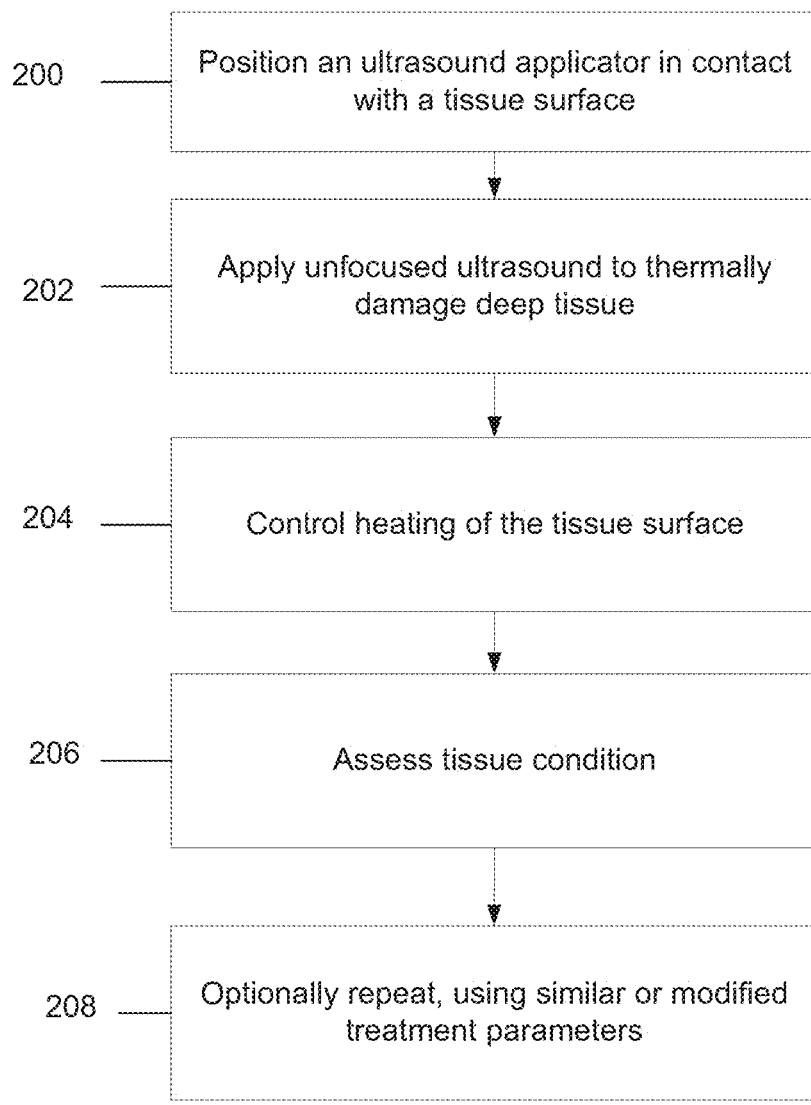

FIG. 2 is a flowchart of applying ultrasound energy to tissue while controlling heating of the tissue surface, according to some embodiments.

In some embodiments, an ultrasound applicator comprising one or more ultrasound transducers is positioned in contact with a tissue surface (200), for example in contact with the skin. In some embodiments, contact is between an external surface of the one or more ultrasound transducers and the tissue. Optionally, contact is achieved when at least 60%, at least 80%, at least 90% or intermediate, higher or smaller percentage of an external surface area of the ultrasound transducer(s) contacts the tissue surface.

In some embodiments, unfocused ultrasound energy is applied to thermally damage deep target tissue (202), for example tissue located at least 1.5 mm, at least 3 mm, at least 5 mm or intermediate, shorter or longer distances beyond the tissue surface.

In some embodiments, unfocused ultrasound energy is applied for treating skin tissue. Optionally, the energy is applied selectively, for example to cause thermal damage to deeper skin layers such as the dermis while damage to upper layers such as the epidermis is reduced or prevented. In an example, dermis tissue at a depth of 2 to 1.55 mm is thermally damaged.

In some embodiments, the applied energy is sufficient to raise a temperature of the target tissue, for example to a temperature between 50-80 degrees Celsius, such as 60-70 degrees Celsius, 55-65 degrees Celsius, 70-75 degrees Celsius or intermediate, higher or lower temperatures. Optionally, the energy is applied over a time period between 1-60 seconds, such as 5-10 seconds, 10-20 seconds, 15-30 seconds or intermediate, longer or shorter time periods.

In some embodiments, the applied energy ablates the target tissue. In some embodiments, target tissue (e.g. collagen) is denatured and/or coagulated.

In some embodiments, the energy is applied selectively to thermally damage lesions separated by areas area of healthy, substantially undamaged tissue. A potential advantage of controlling application of the ultrasound energy to produce lesions separated by healthy tissue may include promoting healing, for example by inducing growth of elastin and/or collagen fibers.

In some embodiments, a lateral distance between thermally damaged lesions is between 1-5 mm, for example 2-4 mm, 3-5 mm, 1-2 mm or intermediate, longer or shorter distances. In some embodiments, each thermally damaged lesion is between 0.5 $mm^3$-5 $mm^3$ in volume, for example 2 $mm^3$, 4 $mm^3$, 1 $mm^3$ or intermediate, larger or smaller volumes.

In some embodiments, the produced lesion is substantially cylindrical.

Alternatively, a lesion is spherical, cubical, cone shaped.

In some embodiments, the energy selectively targets tissue, for example targeting tissue of the reticular dermis such as collagen, elastic fibers and/or extrafibrillar matrix. Optionally, the effect of the emitted energy on other types of tissue such as fat tissue and/or connective tissue is small, so that fat tissue forms a natural barrier to the damage (e.g. a layer of fat tissue below the dermis). A potential advantage of applying unfocused ultrasound energy which produces a thermal effect that is naturally reduced or limited by certain types of tissue such as fat tissue may include reduced sensitivity to anatomical variations (e.g. inter-patient variations in tissue structure and/or thickness).

In some embodiments, heating of the tissue surface is controlled (204). In some embodiments, cooling is applied to the tissue surface to reduce a thermal effect of the emitted ultrasound beam on the tissue surface.

In some embodiments cooling is applied via the ultrasound transducer(s), for example by cooling a transducer's emitting surface to a temperature lower than a current temperature of the tissue. Additionally or alternatively, cooling is applied by delivering cold liquid and/or gas to the tissue, for example through designated holes formed in the transducer surface.

In some embodiments, heat is conducted to and/or from the tissue surface contacting the emitting surface of the ultrasound transducer.

In some embodiments, the transducer's emitting surface contacts the tissue directly. Alternatively, a thin layer of an isolating material such as Kapton and/or other polyimide film and/or Parylene and/or PEEK and/or PTFE and/or Silicon rubber and/or Latex, is disposed on the emitting surface of the transducer which faces the tissue. Optionally, a face of the applicator which faces the tissue is coated by a protective layer, for example a thin thermally and/or electrically insulating layer.

In some embodiments, cooling systems and/or methods for example as described herein are used for cooling the transducer's emitting surface (e.g. cooling using fluid circulation, a thermal reservoir block, a thermos electric cooler and/or other methods). Optionally, cooling is applied before, after and/or in between energy emission periods.

Additionally or alternatively, cooling is applied to tissue surface in a vicinity of the tissue area contacting the transducer's emitting surface. Optionally, non-active transducers and/or transducers activated using different parameters than the treatment parameters cool the tissue in a vicinity of the treating transducer.

Additionally or alternatively, cooling of the tissue surface before, during and/or after energy emission is achieved by directly cooling the tissue surface, for example using gel. In some embodiments, the gel is an ultrasonic conductive gel. Optionally, the gel fills up gaps between the transducer's emitting surface (or a coating thereon) and the tissue. Additionally or alternatively, a liquid filled balloon is used for cooling the tissue surface.

In some embodiments, one or more parameters are taken into consideration when controlling heating of the tissue surface, such as: heat dissipation to the surroundings (depending, amongst other parameters, on the ambient temperature); parameters of the emitted ultrasound beam (e.g. intensity profile, frequency profile, beam angle, beam shape); the type of tissue being treated; thermal conductivity, thermal capacitance and/or heat dissipation coefficients of the tissue being treated; absorption and/or attenuation coefficients of the ultrasound waves in the tissue; a geometry and/or dimensions of the piezo element and/or other parameters.

In some embodiments, heating of the tissue surface is controlled by selecting a piezo element having a certain thickness and/or width. For example, the piezo element is selected with a thickness which defines a resonance frequency between 9-22 MHz.

In another example, a width of the piezo element is selected to provide an ultrasonic beam having a pre-defined opening angle, for example a width between 0.5-3 mm is selected to provide a beam having an opening angle between 5-45 degrees.

Optionally, increasing the beam angle (e.g. by providing a piezo element of increased width) reduces a thermal effect on the surface of the tissue.

In some embodiments, a temperature of the emitting surface of the transducer is determined. Optionally, the temperature is measured via one or more temperature sensors. Additionally or alternatively, a temperature of the emitting surface is determined by measuring a capacitance of the transducer during excitation. In some embodiments, a temperature of a material coating the transducer's emitting surface (e.g. Kapton) is determined. Additionally or alternatively, tissue bio-impedance is measured (for example by stimulating the tissue via the transducers) as an indication of a thermal condition of the tissue. Additionally or alternatively, the tissue temperature is determined using ultrasound signals reflected from the tissue.

Optionally, the signals are received by the applicator (e.g. by one or more receivers configured on the applicator, and/or by one or more transceivers. In some embodiments, one or more transceivers are configured for both emitting the treating energy and receiving the reflected signals).

In some embodiments, a tissue condition is assessed (206). Optionally, the tissue condition is assessed during treatment and/or following treatment. In some embodiments, the extent of thermal damage is assessed.

In some embodiments, the extent of thermal damage is assessed by analyzing echo signals reflected from the tissue. In some embodiments, the device is configured to receive echo signals, and optionally the device's controller is configured for performing such analysis. Optionally, one or more of the applicator's transducers are configured to function as transceivers configured to receive the returning signals.

In some embodiments the tissue condition is assessed after a certain time period has passed from the treatment, for example 1 day, 1 week, 3 weeks, 1 month, 3 months or intermediate longer or shorter time periods from the treatment. For example, in some embodiments, a visible effect can be observed on treated skin following treatment, for example tightening of the skin.

Optionally, treatment is repeated (208). In some embodiments, treatment is repeated until a desired effect is achieved, for example visible tightening of the skin.

In some embodiments, one or more treatment parameters are modified, for example energy parameters (e.g. frequency, intensity); a temperature profile of the transducer(s); a treatment duration; a shape and/or size of the applicator.

In some embodiments, treatment is applied to tissue other than skin, for example tissue of the reproductive system, urinary tract, gastrointestinal tract, airways and/or any other tissue approachable via natural orifices of the body.

FIGS. 3A-F are cross section views of various structures of an ultrasound transducer, according to some embodiments.

Figure 3A:
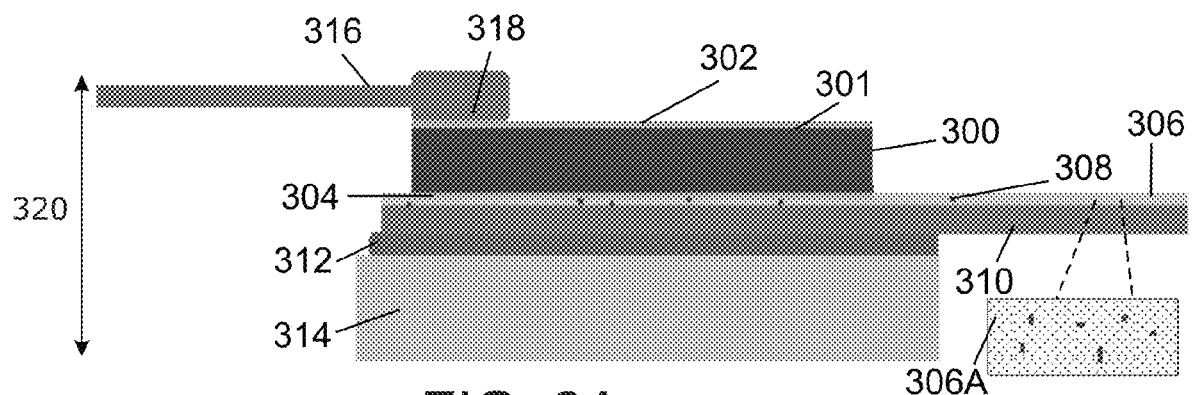

In some embodiments, for example as shown in FIG. 3A, the transducer comprises an ultrasound emitting element, such as a piezoelectric element (PZT) 300 configured to vibrate under excitation to produce ultrasound waves. In some embodiments, PZT 300 comprises a top electrode 302 and/or a bottom electrode 304.

In some embodiments, PZT 300 comprises a rectangular profile. Optionally, PZT 300 comprises a flat emitting surface 301.

In some embodiments, dimensions of emitting surface 301 are, for example, 1 mm×8 mm, 2 mm×5 mm, 3 mm×4 mm or intermediate, larger or smaller dimensions. Optionally, a thickness of PZT 300 is between 80-300 microns. A potential advantage of a PZT comprising relatively small length and/or width may include reducing a risk of mechanical fracture of the PZT. A potential advantage of a PZT comprising relatively small thickness may include improved heat conduction and a higher resistance against thermal stress.

Alternatively, PZT 300 comprises a different cross section profile, for example circular, squared, and/or any other profile defining at least one substantially flat emitting face.

In some embodiments, PZT 300 is mounted on a substrate 306. Optionally, a thickness of substrate 306 ranges between, for example, 10-150 microns, such as 15 microns, 25 microns, 30 microns, 80 microns, 100 microns, 120 microns or intermediate, higher or lower thicknesses.

In some embodiments, substrate 306 comprises a plurality electrically conductive elements 308 disposed in a matrix of electrically insulating material, such as a polymer matrix, for example comprising Kapton and/or other polyimide film and/or Parylene and/or PEEK and/or PTFE and/or Silicon rubber and/or Latex. In some embodiments, substrate 306 comprises at least 10 electrically conductive elements, at least 50 electrically conductive elements, at least 100 electrically conductive elements, at least 1000 electrically conductive elements or intermediate, higher or lower number. In some embodiments, electrically conductive elements 308 comprise electrically conductive material, such as metal or metal alloys for example including tungsten, aluminum, and/or other electrically conductive material, such as carbon. In some embodiments, an electrically conductive material with a relatively low density is used. A potential advantage of a low density material may include imposing less resistance against PZT 300, for example during vibration of the PZT.

In some embodiments, the electrically conductive elements are in the form of particles (see enlarged view 306A), e.g. rounded particles disposed in the polymer matrix. Optionally, a diameter of the particle ranges between 5-30 microns, such as 10 microns, 15 microns, 20 microns or intermediate, larger or smaller diameter. In some embodiments, the electrically conductive elements are in the form of thin fibers (see enlarged view 306B). Optionally, the fibers extend along a thickness of substrate 306.

Optionally, a thickness of the fibers is between 0.0001-0.5 mm. Optionally, a length of a fiber corresponds with the thickness of substrate 306, for example between 5-50 microns. In some embodiments, carbon fibers (e.g. in the form of a mesh of carbon nano-tubes) are used.

In some embodiments, a volume percentage of the electrically conductive elements in the polymer matrix is between, for example, 0.1% and 30%, such as 0.5%, 1%, 5%, 10%, 15% or intermediate, larger or smaller percentage. In some embodiments, the electrically conductive content of substrate 306 is relatively small.

Optionally, at least 80%, at least 90%, at least 95% or intermediate, larger or smaller percentages of a bottom surface area of bottom electrode 304 contacts the electrically insulating polymer of substrate 306. Optionally, less than 20%, less than 10%, less than 5% or intermediate larger or smaller percentages of a bottom surface area of bottom electrode 304 contacts electrically conductive material (e.g. particles and/or fibers).

FIG. 3F schematically illustrates substrate layers 306A and 306B (each shown underneath bottom electrode 304). 309 marks examples of contact points (marked with a dashed circle) between a bottom surface (e.g. proximally facing) surface of bottom electrode 304 and the electrically conductive elements 308 of substrate 306, such as particles (306A) and/or fibers (306B). In some embodiments, contact points 309 are randomly districted across the interface between bottom electrode 304 and substrate 306. Additionally or alternatively, the contact points are arranged in a pattern.

Optionally, the distribution of contact points 309 depends on the location and/or position of conductive elements 308 within the substrate. In some embodiments, contact points 309 are distributed across the mating surfaces such that the contact points are spaced apart from each other.

In some embodiments, substrate 306 comprises electrically conductive glue.

Optionally, the glue is pressure sensitive and is configured to conduct current when pressure is applied to the layer, for example pressure above a certain threshold, such as above $1N/cm^2$, above $3 N/cm^2$, above $0.5N/cm^2$ or intermediate, higher or lower thresholds. In some embodiments, the applied pressure deforms substrate 306 such that the electrically conductive elements contact each other and/or contact electrically conductive layers positioned above and below substrate 306.

In some embodiments, substrate 306 is resilient. Optionally, substrate 306 is resilient enough so as to reduce interfering with vibration of PZT 300. In some embodiments, a shape and/or size of the electrically conductive elements is selected to reduce a rigidity of substrate 306. In some embodiments, substrate 306 comprises silicon rubber, silicon glue (RTV), soft polyurethane and/or other material resilient enough to reduce interfering with vibration of the PZT. In some embodiments, substrate 306 is mounted on and/or otherwise in contact with an electrically conductive layer 310. In some embodiments, layer 310 conducts current for exciting PZT 300. Optionally, current is conducted via substrate 306 to the bottom electrode 304. Optionally, layer 310 comprises copper.

In some embodiments, electrically conductive layer 310 is attached to a base 314 via an isolating layer 312, for example comprising electrically insulating glue.

Optionally, later 312 is rigid.

In some embodiments, base 314 is a portion of a holder element of an applicator for applying ultrasound to tissue. In some embodiments, base 314 comprises or is formed of a metal or metal alloy. In some embodiments, base 314 comprises aluminum. Additionally or alternatively, base 314 comprises copper. A potential advantage of using copper may include a relatively high heat transfer rate.

In some embodiments, a thickness of base 314 is between, for example 0.3-1 mm, 0.5-2 mm, 1.5-4 mm, or intermediate, higher or lower thicknesses.

In some embodiments, electrical current is conducted to top electrode 302 via wiring 316, for example comprising a copper wire. Optionally, wiring 316 is coupled to the electrode by a soldering 318.

In some embodiments, a total thickness 320 of the transducer is smaller than 1 mm, smaller than 2 mm, smaller than 1.5 mm, smaller than 5 mm, or intermediate, larger or smaller thickness.

In some embodiments, substrate 306 is mounted directly on base 314.

Figure 3B:
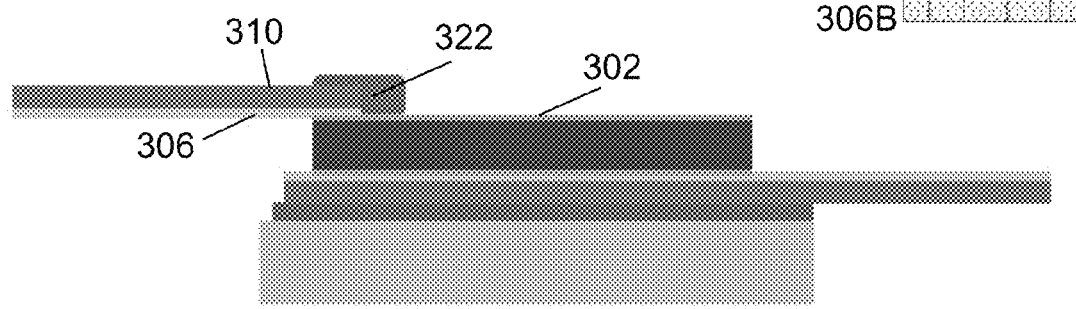

In FIG. 3B, a portion of top electrode 302 (e.g. less than 10%, less than 30%, less than 50% of the surface area of top electrode 302) is in contact with a substrate layer, for example a layer having similar properties to layer 306. In some embodiments, an electrically conductive layer for example having properties similar to layer 310 is configured above the substrate layer. Optionally, an attachment 322 connects substrate layer 306 and conductive layer 310 to the top electrode, for example using glue.

Figure 3C:
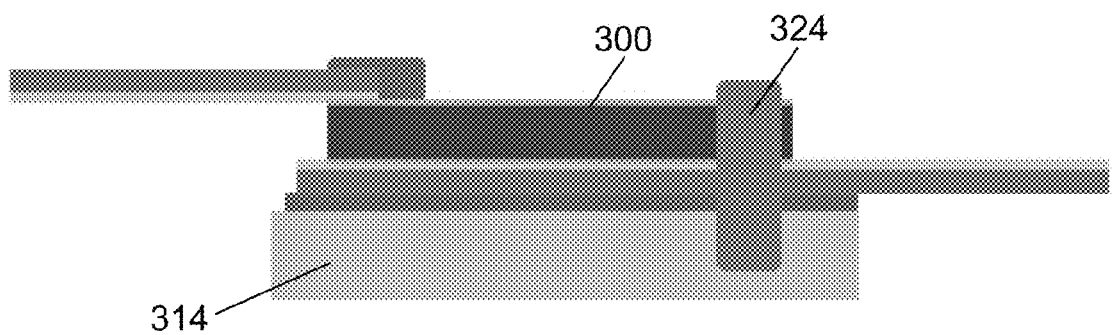

In FIG. 3C, the transducer comprises a reinforcing element 324. In some embodiments, reinforcing element 324 extends across at least a portion of a thickness of the transducer, strengthening an attachment between two or more layers such as between PZT 300 and base 314. In some embodiments, a transducer as shown in FIG. 3C is coated, at least in part (e.g. on a tissue facing end of the transducer), by a biocompatible coating, for example as described hereinbelow in FIG. 3D.

In FIG. 3D, an external top coating 326 extends over at least an exposed portion of top electrode 302, and/or over electrically conductive layer 310. Optionally, coating 326 is suitable for contacting tissue, for example, in some embodiments, coating 326 comprises a biocompatible material. In some embodiments, coating 326 comprises a rigid material. Alternatively, coating 326 is soft. In some embodiments, coating 326 comprises a polymer material, for example Kapton and/or other polyimide film and/or Parylene and/or PEEK and/or PTFE and/or Silicon rubber and/or Latex.

Optionally, a thickness of coating 326 is low enough so as to reduce interference with the ultrasound energy that is transmitted via the coating. Optionally, a thickness of coating 326 ranges between, for example, 10-25 microns, 5-50 microns, 20-40 microns or intermediate, larger or smaller thicknesses. In some embodiments, coating 326 is produced in a chemical vapor deposition process.

In some embodiments, coating 326 is mounted on an adhesive layer 328, which couples coating 326 to top electrode 302. Optionally, layer 328 comprises electrically insulating glue. In some embodiments, adhesive layer 328 comprises a two-part epoxy adhesive. Optionally, adhesive layer 328 is thin enough to least interfere with energy transmission, yet thick enough to hold coating 326 in place, for example having a thickness between 1-10 microns.

FIG. 3E illustrates a transducer in which PZT 300 is mounted, at least in part, on an electrically insulating substrate 330. Optionally, at least 60%, 70%, 80%, 90%, 95% of a surface area of bottom electrode 304 contacts substrate 330. In some embodiments, a thickness of substrate 330 is between, for example, 30-90 microns, such as 50 microns, 70 microns, 85 microns or intermediate, higher or lower thickness.

In some embodiments, substrate 330 comprises glue, for example a double sided glue or tape.

In some embodiments, electrical current is conducted to bottom electrode 304 via wiring 332, for example via a copper wire. Optionally, wiring 332 is coupled to the electrode by a soldering 334.

In some embodiments, a thickness of one or more layers of the transducer "sandwich" structure, for example layers underlying the PZT such as substrate 306 and/or substrate 330 is selected so that an efficiency of the transducer is not lower than 50%, not lower than 60%, not lower than 40% or intermediate, higher or lower efficiencies.

In some embodiments, to maintain a selected efficiency of the transducer, one or more layers of the transducer (e.g. substrate 306 on which the PZT may be mounted) comprise a density low enough so as to impose only a low resistance to vibration of the PZT. Optionally, if the layer comprises conductive particles or fibers, for example as described above, their volumetric percentage in the layer is low enough (e.g. under 1%, under 3%, under 5%) so that the PZT surface substantially does not contact these higher density particles or fibers and its efficiency is substantially undisturbed by these particles or fibers.

In some embodiments, a thickness of the one or more layers is selected so that the rate of heat transfer from the PZT is at least 2-5 Watt/(m^2K). Optionally, in a layer that exhibits low thermal conductivity properties (e.g. layers that comprise polymeric materials), a low enough thickness compensates for the low thermal conductivity.

FIG. 4 is a flowchart of a method for activating an array of ultrasound transducers, according to some embodiments.

In some embodiments, an array comprising a plurality of ultrasound transducers, such as 2, 3, 5, 7, 10, 20, 30 or intermediate, larger or smaller number of transducers is provided (400). Optionally, the array of transducers is a part of an applicator, such as a hand held applicator for applying ultrasound to tissue.

In some embodiments, a thermal effect produced by the array of transducers is controlled by activating two or more transducers of the array at different frequencies to control heating of the tissue (402). In some embodiments, a first transducer is activated a first frequency, and a second transducer is activated at frequency which is at least 10% higher, at least 20% higher, at least 40% higher, at least 70% higher than the first frequency. Alternatively, the second transducer is activated at a frequency which is at least 10% lower, at least 20% lower, at least 40% lower, at least 70% lower than the first frequency.

In some embodiments, one or more transducers are excited at treatment frequencies (e.g. between 10-20 MHz), while one or more other transducers, for example transducers positioned in between the treating transducers, are activated at a frequency different than the treatment frequency. Optionally, the non-treating transducers produce sufficient heat for avoiding over-cooled tissue surface regions, such as tissue surfaces contacted by the cooled applicator which are not directly contacted by the treating transducers. Alternatively, the non-treating transducers are not activated and their contacting surfaces cool the tissue surface in the vicinity of the treating transducers. Alternatively, the non-treating transducers are activated at RF frequencies, for example between 300 KHz to 1 MHz. Optionally, the RF emitting transducers contact the tissue and generate heating of the tissue.

In some embodiments, the number of transducers emitting non-treating energy (e.g. transducers configured in between the transducers that emit energy suitable for producing a thermal damage) is selected in accordance with a desired lateral distance between the thermally damaged tissue regions. Optionally, the distance ranges between 1-5 mm, such as 2 mm, 3 mm, 4 mm, or intermediate, longer or shorter distances.

In some embodiments, the non-treating transducers are heated enough to reduce a temperature difference of tissue surfaces being contacted by transducers activated at different frequencies, for example at the borderline between a transducer that emits thermally damaging energy and an adjacent non-treating transducer.

In some embodiments, an activation frequency of a non-treating transducer is selected relative to the resonance frequency of the transducer. Optionally, the activation frequency is higher than the resonance frequency, for example twice the resonance frequency. Alternatively, the activation frequency is lower than the resonance frequency. A potential advantage of activating a non-treating transducer at a frequency different than the resonance frequency, in which the transducer is most efficient in converting electrical energy to acoustic energy may include converting more electrical energy to heat (rather than to ultrasound energy), for efficiently heating the tissue surface yet reducing thermal damage to deeper tissue. Optionally, the non-treating transducers are activated at a lower intensity than the treating transducers.

FIG. 5 schematically illustrates activation of an array 500 of ultrasound transducers at various frequencies, and a thermal effect on tissue surface being treated by the transducers, according to some embodiments.

In some embodiments, one or more transducers 502 are activated at a frequency suitable for thermally damaging deep tissue, for example a frequency between 8-22 MHz, 10-20 MHz, such as 11 MHz, 15 MHz, 18 MHz.

In some embodiments, one or more transducers 504, 506, 508 are activated at non-treating frequencies, for example at a frequency higher than 20 MHz such as 22 MHz, 33 MHz, 45 MHz, or at a frequency lower than 10 MHz, such as 9 MHz, 5 MHz, 2 MHz. Optionally, transducers 504, 506, 508 are activated at similar frequencies; alternatively, transducers 504, 506 508 are activated at various frequencies.

In some embodiments, one or more transducers 510 are not activated.

In some embodiments, energy emitted by the one or more transducers comprise unfocused ultrasound energy. Additionally or alternatively, energy emitted by the one or more transducers comprises focused ultrasound energy.

In some embodiments, unfocused ultrasound and focused ultrasound are applied simultaneously or successively. A potential advantage of applying focused ultrasound and unfocused ultrasound simultaneously and/or successively may include obtaining a stronger thermal effect on the tissue, as the unfocused ultrasound will heat tissue surrounding the focal point of the focused ultrasound, raising the temperature of the tissue at the focal point. Another potential advantage of using focused ultrasound may include accurately targeting individual treatment points that are isolated from each other.

In some embodiments, focused ultrasound generates a cavitation bubble cloud, for example when applied at a frequency between 0.25-0.2 MHz. Optionally, applying a non-focused ultrasound beam simultaneously or successively to the focused ultrasound heats the cloud region and may provide for targeted ablation of the cloud region. An exemplary embodiment in which focused and unfocused ultrasound energy may be applied together includes hair removal applications, in which the focused ultrasound generates cavitation inside the hair duct, and the unfocused beam, optionally applied at a higher frequency than the focused beam, intensifies heating of the hair duct. Other applications may include sweat gland treatments, acne treatments and/or other treatments.

In some embodiments, energy fields produced by adjacent transducers overlap.

Optionally, the adjacent transducers emit different energy types (e.g. focused ultrasound, unfocused ultrasound, RF). Optionally, the adjacent transducers are driven at different frequencies. In some embodiments, overlapping fields generate a complex field which may include localized peaks of higher intensity.

In some embodiments, beam 512 comprises a substantially trapezoidal profile.

Alternatively, the beam comprises a different profile, such as a conical, rectangular, and/or other profiles. In some embodiments, an opening angle α of beam 512 is between, for example, 5-20 degrees, such as 10 degrees, 15 degrees, 19 degrees.

In some embodiments, an energy distribution of the emitted beam is controlled by selecting energy parameters. For example, in some embodiments, energy parameters (e.g. frequency and/or intensity) are selected so that the ultrasound field of the produced beam is stronger at base of the beam, for example effective to heat the contact point with the tissue more than at other beam portions. Additionally or alternatively, an intermediate portion of the beam is stronger, for example effective to heat tissue at a shallow depth from the surface. Additionally or alternatively, a distant portion of the beam is stronger, for example effective to heat deep tissue regions.

FIG. 5 further shows a thermal effect of an array for example as described herein on the tissue surface 514. In some embodiments, tissue surfaces 516 effected (e.g. by being contacted by) treating transducers 502 are heated the most, for example heated to a temperature between 20-40 degrees Celsius. In some embodiments, tissue surfaces such as 518, 520 and/or 522 which are effected by both the treating transducer and the adjacent optionally cooler transducer are heated to a lower temperature, for example a temperature between 10-30 degrees Celsius. In some embodiments, tissue surfaces such as 524 located further away from the treating transducer are heated to a lower temperature, for example between 5-25 degrees Celsius.

FIG. 6 illustrates a flexible ultrasound applicator 600 comprising an array of ultrasound emitting elements sandwiched between film layers, according to some embodiments.

In some embodiments, applicator 600 comprises one or more ultrasound emitting elements 602, for example PZT elements. Optionally, the emitting elements are disposed in between two film layers 604.

In some embodiments, emitting elements 602 are arranged in series, for example in a chain like configuration, through the elements may not be linked to each other by an element other than one or both of the film layers. Alternatively, the emitting elements are arranged in a two-dimensional array.

In some embodiments, film layer 604 comprises a thickness 606 low enough to provide for dissipating heat from the emitting surface(s) of the emitting element 602, for example a thickness lower than 150 microns.

Additionally or alternatively, applicator 600 comprises a circulating coolant 608, for example flowing adjacent emitting elements 602 for dissipating heat away from the transducers. Additionally or alternatively, emitting element 602 are mounted on a cooled base (not shown herein).

In some embodiments, film layer 604 comprises electrical circuitry 610 configured for activating elements 602. Optionally, circuitry 610 is printed on the film layer, for example on a surface of the layer facing elements 602.

In some embodiments, film layer 604 comprises a flexible material. A potential advantage of a flexible material may include the ability to shape applicator 600 in accordance with a contour of the tissue surface being treated. For example, in some embodiments, applicator 600 is flexed to extend across non-flat skin surfaces, for example across the forehead, around the neck and/or other facial and/or non-facial skin tis sue.

In some embodiments, film layer 604 comprises an electrically and thermally isolating material. In some embodiments, film layer 604 comprises a biocompatible material suitable for contacting tissue.

Optionally, film layer 604 comprises one or more materials such as Kapton, and/or other polyimide film and/or Parylene and/or PEEK and/or PTFE and/or Silicon rubber and/or Latex.

In some embodiments, applicator 600 comprises one or more temperature sensors 612, such as thermistors. Optionally, temperature sensor 612 is configured to indicate a temperature of the emitting element 602, for example by being placed adjacent element 602 (e.g. on and/or in proximity to an emitting surface of emitting element 602). Additionally or alternatively, temperature sensor 612 is configured to indicate a temperature of film layer 604. Additionally or alternatively, temperature sensor 612 is configured to indicate a temperature of the tissue surface being contacted by applicator 600, for example by being placed on and/or within film layer 604, such as on the externally facing surface of layer 604.

In some embodiments, applicator 600 comprises one or more elements for controlling a thermal effect on the tissue, for example including RF electrodes and/or heating resistors (not shown herein) for generating heat in addition and/or instead of the ultrasound emitting elements to control a thermal effect on the tissue, such as on the tissue surface.

In some embodiments an emitting element 602 is without top and/or bottom electrodes. Optionally, electrical connectivity is provided directly to the element (e.g. to the PZT) via circuitry 610 embedded and/or mounted on the top and/or bottom thin layers 604.

FIG. 7 is an exemplary configuration of an ultrasound applicator comprising a cooling module, according to some embodiments.

In some embodiments, applicator 700 comprises a one or more ultrasound transducers 702 (e.g. 9 transducers, 5 transducers, 15 transducers or intermediate, larger or smaller amount). In some embodiments, transducers 702 are mounted on a base 704. Optionally, each transducer 702 is mounted on a distally extending branch 706 of base 704. Optionally, transducers 702 are attached to base 704 by a thin layer of glue, for example thermally conductive and/or electrically conductive glue.

Optionally, for example as shown herein, branches are distanced away from each other a lateral distance 708 of between, for example, 1-6 mm, 2-4 mm, 0.5-3 mm or intermediate, shorter or longer distances. Optionally, a distance between the branches and/or a spatial orientation of the branches with respect to each other is selected in accordance with a lesion pattern intended to be formed in the treated tissue.

In some embodiments, a thermal and/or electrical isolation is configured in between branches 706. Optionally, air is allowed into the gaps defined between the branches for thermally and electrically separating between adjacent transducers.

Additionally or alternatively, a thermally and/or electrically isolating material such as polyurethane foam is disposed between the branches (not shown herein).

Alternatively, in some embodiments, base 704 including branches 706 is coated by a thermally and/or electrically isolating material (e.g. polyimide and/or Parylene, for example having a thickness between 10-20 microns). Optionally, the coating traps air in the gaps between the branches. Alternatively, in some embodiments, base 704 does not comprise branches, and the transducers are mounted directly onto the base. Optionally, base 704 is coated, at least in part, by a thermally and/or electrically isolating material e.g. polyimide and/or Parylene, for example having a thickness between 10-20 microns). In some embodiments, the coating comprises electrical circuitry (e.g. printed circuitry) configured for activating transducers 702 and/or for heating the tissue surface being contacted by the applicator, for example by heating the tissue directly and/or by heating the transducers.

In some embodiments, applicator 700 comprises a cooling module 701, configured for absorbing and/or dissipating heat away from the transducers and/or for actively and/or passively cooling the transducers. In some embodiments, cooling module 701 is configured to transfer heat away from the transducers at a rate fast enough to prevent over-heating of the transducers, such as overheating of an ultrasound emitting surface of the transducer. In some embodiments, the cooling rate is high enough to cool the transducers to a temperature lower than a current temperature of the tissue surface. Optionally, active cooling is provided. A potential advantage of cooling the transducers to a temperature lower than a current temperature of a surface of the treated tissue may include reducing the need for additional cooling elements, such as cooling elements configured to cool the tissue surface directly, as cooling is provided to the transducer and also via the transducer (e.g. via the transducer's emitting surface) cooling the tissue surface being contacted by the transducer. In some embodiments, cooling module 701 is controlled in accordance with activation of the transducers. Optionally, the cooling rate is high enough to overcome heating generated by the energy emitting transducers. Exemplary cooling rates may include 1 K/min or 5 K/min or 10 K/min, or 60 K/min or intermediate values, and heat transfer of 1-7 W/(m^2K), or intermediate values.

In some embodiments, cooling module 701 comprises one more cooling elements, such as a Peltier element, for example in the form of a thermoelectric cooler (TEC) 710. Optionally, one or more TEC elements (e.g. 3 as shown herein) are positioned in contact with base 704. In some embodiments, base 704 comprises aluminum and/or copper and/or brass and/or stainless steel.

In some embodiments, the cooling module 701 comprises a heat sink 712.

Optionally, heat sink 712 is configured to absorb and/or dissipate heat away from TEC elements 710, for example disposed under the TEC elements.

In some embodiments, TEC element 710 is positioned in between base 704 and heat sink 712. Optionally, a distally facing surface 714 of the TEC contacts, at least in part, base 704; a proximally facing surface 716 of the TEC contacts, at least in part, heat sink 712. Optionally, distally facing surface 714 is the cooled side of the TEC; proximally facing surface 716 is the hot side of the TEC. Optionally, power supply to TEC is provided via a power lead (not shown herein).

In some embodiments, each transducer is coupled to a single TEC element.

Optionally, a substrate (e.g. ceramic substrate) configured on distally facing surface 714 is removed, and a direct coupling is produced between the electrical circuitry of the TEC element and the transducer. Such direct coupling may be advantageous, for example, for independently controlling cooling of each of the transducers, for example in an operation mode in which one or more transducers are activated with a first set of energy parameters (e.g. frequency, intensity) and one or more other transducers are activated with a second set of energy parameters.

In some embodiments, a heat transferring layer 720 is disposed between TEC 710 and heat sink 712, and/or between the distally facing TEC surface 714 and base 704, for example comprising a thermally conductive glue, paste and/or pad.

In some embodiments, heat sink 712 comprises a coolant 718, for example comprising fluid and/or gas and/or antifreeze. In an example, the coolant comprises water. Optionally, the coolant is circulated within the heat sink, for example using a pump (not shown herein). In some embodiments, the coolant is cooled by a chiller (not shown herein), for example disposed within heat sink 712 and/or disposed externally to applicator 700.

In some embodiments, cooling module 701 comprises a fan (not shown herein), configured for providing additional heat removal and/or for replacing one or more cooling elements as described hereinabove (e.g. a TEC and/or a heat sink).

Additionally or alternatively, cooling module 701 comprises a thermal reservoir block (not shown herein), for example a block of copper. Optionally, the thermal reservoir block is pre-cooled to a temperature sufficient to cool transducers 702, for example via base 704, enough to reduce or prevent thermal damage to a surface of the tissue.

In some embodiments, base 704 is mounted directly on heat sink 712.

Optionally, in such configuration, a temperature of coolant 718 is reduced to an even lower degree (e.g. as compared to an applicator in which a TEC element is used).

In some embodiments, a continuous PZT plate may be used, for example replacing the branched structure of base 704. In some embodiments, the continuous PZT plate is processed to define multiple, optionally independently operable emitting elements for example as described hereinbelow.

Additionally or alternatively, a continuous porous PZT plate is used. In some embodiments, the porous PZT plate is coated by an electrically conductive layer (e.g. a silver layer), and the layer is removed (e.g. etched) in a pattern suitable to produce separate electrodes for exciting the respective PZT portions contacting the electrodes.

Additionally or alternatively, multiple emitting elements are produced by placing separate electrodes on the top and/or bottom faces of the porous PZT plate. In some embodiments, when using a porous PZT plate, a thickness of the plate is selected to be lower than, for example, a thickness of a non-porous PZT element, since the speed of sound is lower in the porous material.

In some embodiments, applicator 700 comprises an arrangement including more than one base which carries transducers. In an example, two bases are arranged to oppose each other (e.g. defining a mirrored symmetry). Optionally, a distance and/or angular position between the bases is selected and/or modified to produce a specific lesion pattern in the treated tissue. Optionally, each of the bases is coupled to a separate TEC element.

In some embodiments, applicator 700 comprises one or more temperature sensors 724. In some embodiments, sensors 724 are placed in between transducers 702. Optionally, sensors 724 are coupled to a coating (e.g. a polyimide and/or parlyene coating of the base, for example as described hereinabove) and/or coupled to an isolating material configured between the branches. In some embodiments, sensor 724 is configured to indicate a temperature of transducer 702, for example a temperature of the emitting surface of the transducer. Additionally or alternatively, senor 724 is configured to indicate a temperature of the tissue surface. Optionally, temperature sensor 724 is positioned in proximity to the transducer, for example between 0.1 mm to 1 mm from the transducer's emitting surface.

Additionally or alternatively, a temperature of the transducer is assessed by analyzing echo signals reflected by the tissue and received by applicator 700.

Optionally, applicator 700 comprises one or more ultrasound receiving elements. Optionally, one or more transducers 700 are configured to function both as emitter and as receivers.

In some embodiments, applicator 700 comprises one or more RF electrodes (not shown). Optionally, the RF electrodes are coupled to a coating of the base and/or coupled to an isolating material between the transducers. In some embodiments, the RF electrodes are used for applying additional heating to the tissue surface, for example so as to reduce thermal damage to the surface. Additionally or alternatively, the RF electrodes are used for measuring bio-impedance of the tissue. Optionally, bio-impedance measurements are performed to assess contact of the transducers with the tissue and/or as a measure of the tissue condition in response to treatment.

In some embodiments, a thin gel pad 728 (e.g. having a thickness between 0.1-1 mm) is disposed on a distal end of applicator 700. Optionally, gel pad 728 enhances contact between the transducers and the tissue. Optionally, gel pad 728 applies cooling to the tissue surface (e.g. pre-cooling the tissue prior to energy emission). In some embodiments, gel pad 728 is disposable and is replaced between treatment sessions and/or in between patients.

Additionally or alternatively, applicator 700 is inserted into a thin balloon, which can be replaced between treatment sessions and/or in between patients.

FIGS. 8A-C illustrate a large continuous ultrasonic transducer construct processed to form an array of separate transducers, according to some embodiments.

In some embodiments, an array of emitting elements such as an array of separately operable ultrasonic transducers 802 is manufactured by constructing a large transducer 800 and processing the large transducer to produce an array of separately operable transducers. In some embodiments, the large transducer is constructed by layering materials to form a construct for example as described herein (e.g. in FIGS. 3A-F).

In some embodiments, processing comprises dicing, etching and/or laser cutting the large transducer into the plurality of transducers.

In an example, a 30×8×0.2 mm large transducer is diced into, for example, 20-28 adjacent, independently operable transducers, each having an emitting surface of, for example, 8 mm length and 1 mm width.

In some embodiments, the plurality of transducers are independently operable.

Optionally, different transducers of the formed array are configured to be stimulated at different frequencies.

In some embodiments, processing the large transducer comprises cutting through a full thickness of the large transducer. Alternatively, processing the large transducer comprises cutting through a partial thickness only, for example to separate the transducers up to the upper electrode or up to the bottom electrode of each transducer.

In some embodiments, a distance between adjacent transducers is defined by a thickness of a blade of a saw (e.g. wafer saw) and/or other cutting element used for the cutting the continuous large transducer.

A potential advantage of manufacturing an array of transducers by processing a large transducer construct may include obtaining transducers that are similar to each other in size and therefore in properties.

FIG. 8B is an image of a large transducer construct, before being cut into a plurality of thin, separately operable transducers, such as transducer 802 shown in a side-view in FIG. 8C.

FIGS. 9A-B are exemplary graphs of activation of an array of ultrasound transducers, according to some embodiments.

In some embodiments, for example as schematically shown in FIG. 9A, various ultrasound transducers of an array are activated using different energy parameters sets (e.g. activated at different frequencies and/or at different intensities and/or at different durations and/or at different powers). In the schematic graph of FIG. 9A, 4 ultrasound transducers are activated at different frequencies. Optionally, activation is controlled to control heating of the tissue surface. Optionally, activation is controlled for reducing temperature differences between adjacent transducers.

Optionally, different transducers are activated with different parameter sets to produce a selected temperature distribution at deeper layers of the tissue.

FIG. 9B is a table of activation parameters of an array comprising a plurality of transducers, in this example including 19 transducers. In some embodiments, a higher or lower number of transducers may be used, for example between 1-50 transducers.

The exemplary parameters shown herein may be applied for treating skin tissue (e.g. for a skin tightening treatment).

In the described example, dimensions of a PZT element of each transducer included a rectangular emitting surface having a surface area of 5 mm^2, for example having a length of 5 mm and a width of 1 mm. It is noted that PZT elements of other shapes and/or dimensions may be used.

In some embodiments, use of thin transducers (e.g. transducers having a width of less than 4 mm, less than 2 mm, less than 1 mm) provides for arranging a plurality of transducers adjacent each other to form an array.

Optionally, two or more transducers of the array are activated simultaneously to emit unfocused ultrasound for targeting a plurality of spaced apart tissue regions.

A potential advantage of using thin transducers that emit unfocused ultrasound may include the ability to treat a plurality of tissue regions using an array of transducers that is small enough to be mounted on a head of a hand held applicator. This may provide an advantage over, for example, focused ultrasound, in which a single large transducer may be needed for focusing the energy towards a single focal point.

FIG. 10 is a flowchart of a method for aesthetic ultrasound skin treatment, according to some embodiments.

In some embodiments, ultrasound energy is emitted to produce spaced apart lesions of thermal damage, for example in the dermis layer of the skin (1000). In some embodiments, the energy is unfocused.

In some embodiments, the applied energy raises a temperature of defined volumes of dermis tissue, for example to a temperature between 60-70 degrees Celsius. Optionally, the thermally damaged volumes are configured a distance below the uppermost skin layer, the epidermis, for example a distance of at least 1 mm, at least 1.5 mm, at least 2 mm, at least 3 mm, at least 5 mm or intermediate, longer or shorter distances.

In some embodiments, cooling is applied to maintain a temperature of the epidermis between 5-40 degrees Celsius, such as 5-10 degrees, 10-20 degrees, 7-15 degrees, 20-30 degrees, or intermediate, higher or lower ranges. Optionally, the applicator's cooling module is set to a temperature of between −5 to −20, effective to reach the 5-40 degrees range on the tissue surface. In some embodiments, cooling of the epidermis to a temperature below 1 degree Celsius is avoided, for example to prevent a situation in which the skin adheres to the applicator.

In some embodiments, cooling is applied prior to energy emission.

Additionally or alternatively, cooling is applied in between periods of energy emission. Additionally or alternatively, cooling is applied during energy emission.

Optionally, the transducer's surface is continuously cooled. In some embodiments, cooling is applied in response to a temperature indication, for example if a temperature indicated by one or temperature sensors contacting the tissue is higher than a threshold, for example higher than 20 degrees, higher than 30 degrees, higher than 40 degrees or intermediate, higher or lower thresholds, stronger cooling is applied. Optionally, activation of the TEC element is controlled in accordance with the temperature indication.

FIG. 11 is a schematic diagram of a system for ultrasound skin treatment, according to some embodiments.

In some embodiments, system 1100 comprises a hand unit 1102 operably coupled to a console 1104. In some embodiments, hand unit 1102 is coupled to the console by a wired connection. Additionally or alternatively, hand unit 1102 is coupled to the console by a wireless connection.

In some embodiments, hand unit 1102 comprises a handle 1106 to which an ultrasound applicator 1108 is attached. In some embodiments, applicator 1108 comprises one more energy emitting elements, such as transducers 1110. In some embodiments, applicator 1108 comprises a cooling module, for example comprising a TEC element 1112; a heat sink 1114; and optionally a fan 1116. In some embodiments, one or more temperature sensors 1118 are incorporated in the applicator, for example positioned in proximity and/or on transducers 1110.

In some embodiments, applicator 1108 is positioned on the treated skin 1120.

Optionally, the applicator is positioned directly, for example such that the energy emitting surfaces of the transducers 1110 contact the skin directly.

Alternatively, gel is applied the skin. In some embodiments, a gel blister is coupled to applicator 1108. Optionally, the gel blister is configured for slow release of the gel to apply it to the skin, for example during treatment.

Alternatively, applicator 1108 is inserted into a thin balloon which in turn contacts the skin.

In some embodiments, during operation, handle 1106 is moved across a surface of epidermis 1122, for example by a physician. In some embodiments, the movement pattern is selected in accordance with the intended lesion pattern in the tissue. In some embodiments, movement is performed in a direction substantially perpendicular to the long axes of the transducers. Alternatively, movement is performed in a direction substantially parallel to the long axes of the transducers.

Alternatively, movement is performed in a direction substantially at an angle to the long axes of the transducers.

In some embodiments, a shape and/or size of the transducer's emitting surface and/or a manner in which the transducer is moved across the tissue surface are selected to produce a certain lesion pattern, for example movement of a rectangular transducer across the tissue, along the long axis of the transducer may produce continuous, spaced apart lines of strong thermal damage inside the tissue. Alternatively, movement of the rectangular transducer along its short axis may produce continuous, close lines of relatively weak thermal damage inside the tissue.

In some embodiments, a squared, circular, or semi-circular transducer surface having a maximal width of, for example, 2 mm, is moved intermittently across the tissue surface (e.g. with 3-10 second intervals between emissions)

to generate spaced apart points of thermal damage with undamaged tissue between them, in a fractional manner.

In some embodiments, moving the handle while setting a predetermined delay between excitation pulses of the plurality of ultrasound elements of the applicator provides for steering the emitted beam through a range of angles, to produce a desired thermal effect in the tissue.

In some embodiments, applicator 1108 is held against the tissue and energy is emitted for a time period of between 1-30 seconds, such as 3 seconds, 5 seconds, 9 seconds, 10 seconds, 20 seconds or intermediate, longer or shorter time periods before moving the applicator again to another location. Optionally, the emission duration and/or other energy parameters are selected in accordance with the tissue type and/or condition to be treated. For example, for treating wrinkles in the forehead each energy emission period may range between 8-10 seconds. When treating sagging skin in the neck area, the energy emission period may be longer, for example between 10-20 seconds. Optionally, the energy frequency is modified, for example a lower frequency is selected.

In some embodiments, energy is applied intermittently, for example with time intervals between 5-30 seconds between emission periods. Optionally, energy is applied in a duty cycle of between 1-50%. Alternatively, energy is applied in a continuous mode.

In some embodiments, one or more lesions 1124 are created in the tissue, for example in the reticular dermis 1126. Optionally, multiple lesions are created simultaneously (e.g. by using an array of transducers).

In some embodiments, a cross section profile of lesion 1124 comprises an elongated, substantially elliptical profile. In some embodiments, a volume of lesion 1124 is between 1 $mm^3$ to 3 $mm^3$, between 0.3 $mm^3$ to 2 $mm^3$, between 1 $mm^3$ to 7 $mm^3$ or intermediate, larger or smaller volume.

In some embodiments, lesions 1124 are spaced apart from each other, for example a distance 1128 of 1 mm, 2 mm, 4 mm, 6 mm, 8 mm or intermediate, longer or shorter distances. In some embodiments, damaged tissue within the lesion comprises denatured collagen and/or cells that underwent necrosis and/or coagulated blood In some embodiments, the damage induces an inflammatory wound-healing response of the tis sue.

In some embodiments, tissue between the lesions remains substantially undamaged. A potential advantage of healthy tissue between the lesions of thermal damage may include stimulating growth of tissue, such as collagen and/or elastin fibers, which in turn may lead to remodeling of the tissue, lifting and/or tightening the skin. In some cases, a visible effect on the skin may observed after 1 months, after 3 months, after 6 months, after 9 months or intermediate, longer or shorter time periods.

In some embodiments, epidermis 1122 remains substantially undamaged.

Alternatively, in some embodiments, minor thermal damage is caused to the epidermis. Optionally, the damage is higher towards the bottom of the epidermis, closer to the dermis, and lower towards the uppermost external surface of the dermis.

In some embodiments, tissue layer 1128 comprising fat and/or connective tissue define as a natural barrier of the thermal damage. In some embodiments, due to higher energy attenuation in the dermis as compared to energy attenuation in fat tissue, the unfocused ultrasound heats the dermis to a substantially higher temperature than the temperature in the fat tissue. Optionally, in such a setup, subcutaneous fat of the hypodermis defines a lower limit to the spatial spread of the thermal damage. A potential advantage of using unfocused ultrasound may include that the dermis is targeted regardless of anatomical variations, such as variations in a depth of the dermis and/or presence of wrinkles. This reduced sensitivity to anatomical variations may provide an advantage over, for example, focused ultrasound, in which a fixed focal point has to be predetermined and the energy may reach undesired tissue locations if the anatomy of the tissue is slightly different than the one taken into consideration.

In some embodiments, a contact between the applicator and the tissue surface (e.g. the epidermis) is assessed. In some embodiments, one or more of the following may be used for indicating contact with the tissue (e.g. whether contact has been established and/or whether the applicator is positioned in sufficient proximity to the tissue):

A. measuring a change in impedance of the one or more transducers (e.g. prior to contact and following contact with the tissue)

B. measuring electric power consumption of the one or more transducers, before, during and/or after excitation.

C. measuring a change in ringing attenuation of the one or more transducers following excitation D. measuring a change in a cooling curve of the one or more transducers following excitation E. measuring bio-impedance of the tissue, for example via two transducers F. measuring changes in a cooling curve of one or more temperature sensors before and/or during excitation G. measuring changes in acoustic signals received by one or more transducers H. measuring a change in amplifier gain I. measuring a change in the capacitance of the one or more transducers J. measuring capacitance differences between upper electrodes of different transducers, such as adjacent transducers.

In some embodiments, overheating of the transducer is reduced or prevented.

Optionally, a temperature of the emitting surface of the transducer is maintained below 20 degrees Celsius, 25 degrees Celsius, 15 degrees Celsius or intermediate, higher or lower temperatures.

In some embodiments, overheating of the tissue surface is reduced or prevented. Optionally, a temperature of the tissue surface is maintained below, for example, 40 degrees, 38 degrees, 41 degrees. In some embodiments, one or more of the following may be used for assessing a temperature of the transducer and/or the tissue:

A. measuring a temperature of the ultrasound emission element (e.g. PZT), for example before, during and/or following energy emission, for example using one or more temperature sensors.

B. measuring a capacitance of the ultrasound emission element as an indicator of temperature.

C. measuring a temperature of a coating disposed on the one or more transducers, for example using one or more temperature sensors positioned adjacent the coating and/or via thermo-resistors incorporated in circuitry embedded in the coating, in accordance with some embodiments.

D. measuring bio-impedance of the tissue and/or changes thereof.

E. measuring impulse response damping changes and assessing a temperature of the transducer based on a correlation between damping changes and temperature.

F. measuring impedance of the transducer.

Optionally, temperature sensitive materials are incorporated in the transducer, and a change in their properties affects the transducer's impedance. For example, viscosity of glue coupling a PZT element to the base changes in response to a change in temperature of the PZT element.

In some embodiments, one or more of the following may be used for reducing pain before and/or during and/or following treatment:

A. Exciting one or more transducers at a low frequency, for example a frequency between 50-400 KHz, such as 90 KHz 100 KHz, 200 KHz, 300 KHZ.

Optionally, the intensity is selected to be between 0.05 W/cm^2 to 1 W/cm^2.

In some embodiments, the low frequency is obtained by activating two or more adjacent transducers at close but not similar frequencies, to produce an acoustic beat.

Additionally or alternatively, the transducer is activated at a bending mode frequency.

B. Exciting one or more transducers at their bending mode resonance frequencies. Optionally, extensive cooling is applied simultaneously.

C. Exciting two or more adjacent transducers at slightly different frequencies that are close enough to each other to generate an acoustic beat, for example using frequencies in the range of 50-200 KHz, according to some embodiments.

D. Prior to treating, activating one or more transducers at an intensity that is higher than the intensity required for treatment, for a short period of time, to numb nerves at the targeted area. Optionally, partial blocking of pain is achieved by producing a low level of thermal damage in the tissue, as nerves are more sensitive to the high temperatures as compared to non-nervous tissue. In an example, energy is applied over 0.01-1 second at an intensity that is between 20-200% higher than the treatment intensity, to cause numbing of nerves. Optionally, the energy is applied as a pulse train.

FIGS. 12A-F show schematic isotherms representing temperature distribution in the tissue associated with applying of different energy types and/or energy parameters, according to some embodiments.

In some embodiments, a transducer 1201 is positioned on the tissue surface 1202, e.g. on the skin, and energy is emitted from the transducer. (For clarity, the schematic isotherms shown herein show a thermal effect on the tissue when no cooling is applied).

Figure 12D:
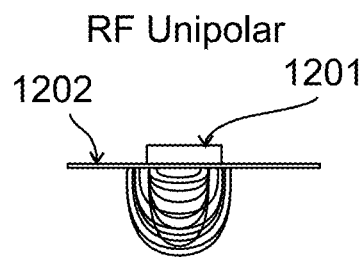
Figure 12A:
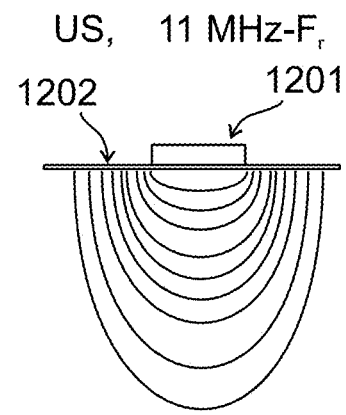
Figure 12E:
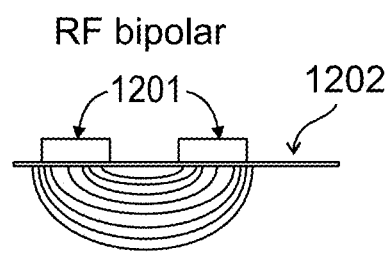
Figure 12B:
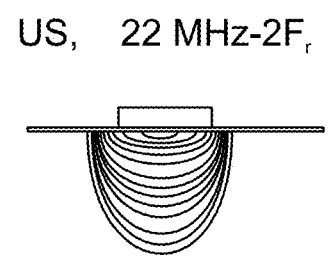
Figure 12F:
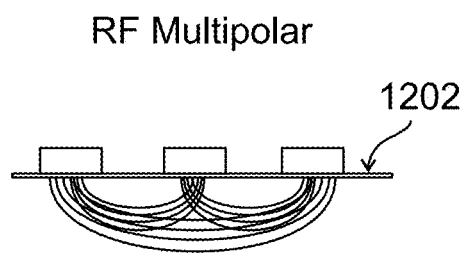
Figure 12C:
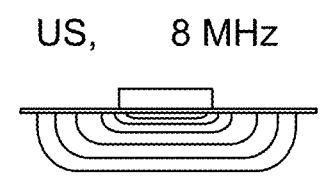

In some embodiments, the transducer is controlled to emit unfocused ultrasound energy having selected parameters. FIGS. 12A-C illustrate temperature distributions in the tissue in response to applying unfocused ultrasound energy at 3 different frequencies, for example as shown herein: 11 MHz, being the resonant frequency in this example (FIG. 12A), 22 MHz (FIG. 12B), and 8 MHz. (FIG. 12C).

Optionally, for example as shown herein, emission of unfocused ultrasound energy at the transducer's resonance frequency may produce a relatively widespread and deep thermal effect on the tissue (FIG. 12A); emission of energy at a frequency higher than the resonance frequency (e.g. twice the resonance frequency, FIG. 12B) may produce a relatively dense and narrow thermal effect on the tissue; emission at a frequency lower than the resonance frequency may produce a widespread and shallow thermal effect on the tissue.

In some embodiments, different energy types are applied to the tissue (e.g. ultrasound (focused and/or unfocused), RF (unipolar, bipolar, and/or multipolar), microwave and/or other energy forms. FIGS. 12D-F illustrate temperature distributions in the tissue in response to applying unipolar RF (FIG. 12D), bipolar RF, via two transducers (FIG. 12E), and multipolar RF, for example via 3 transducers (FIG. 12F).

As shown in the figure, applying of unipolar RF may produce a relatively narrow, dense and shallow thermal effect on the tissue (FIG. 12D); applying of bipolar RF may produce a more widespread, dense and shallow thermal effect on the tissue.

Optionally, the extent of the effect is set by a position of the transducers relative to each other; applying of multipolar RF may produce an even more widespread, dense and shallow thermal effect on the tissue.

In some embodiments, one or more energy types and/or energies having different parameters are applied simultaneously and/or successively to produce a desired thermal effect on the tissue. In some combinations, the temperature distribution produced in the tissue is an additive result of the combined energies.

Alternatively, the temperature distribution in the tissue in response to applying different energies produces a more complex, synergistic effect.

In some embodiments, heating of the tissue is generated by means other than energy emission, for example by applying resistive heating on the transducer's electrodes and/or by mechanically heating the transducer's tissue-facing surface.

FIGS. 13A-B are a side view (FIG. 13A) and an enlarged view (FIG. 13B) of an ultrasound applicator head, according to some embodiments.

In some embodiments, applicator head 1300 comprises an array of transducers 1302. Optionally, each transducer 1302 is mounted on a separate distally extending branch 1304 of a base 1306. In some embodiments, a cooling element such as a TEC element 1308 (shown in part) is disposed proximally to the base.

In some embodiments, thermal insulation exists between adjacent transducers. Optionally, the thermal insulation comprises air. Alternatively, one or more materials are placed at the spaces for providing thermal insulation. In some embodiments, the thermal conductivity coefficient of such materials is smaller than 0.1 W/m*K.

In some embodiments, head 1300 comprises one more temperature sensors, such as thermistors 1310. Optionally, the thermistors are disposed on a distal end of head 1300, in a position suitable to measure a temperature of the tissue, directly and/or via a thin coating layer 1312, for example a Kapton coating.

In some embodiments, coating 1312 seals the applicator head, defining air-filled lumens in between branches 1304. Optionally, one or more supporting beams 1314 extend between base 1306 and coating 1312. In some embodiments, a distal end face of beam 1314 comprises a dent 1316 (shown in the enlarged view of FIG. 13B) facing a thermistor 1310. Optionally, the thermistor is attached only to coating 1312 and does not lean on the beam. Dent 1316 formed in the beam face may provide an air spacing around the thermistor, so as to prevent the thermistor from being cooled by the beam.

In some embodiments, a thickness of coating 1312 is thin enough (e.g. smaller than 25 microns) so that when head 1300 contacts the tissue, thermistors 1310 immediately sense a rise in temperature, indicating that contact with the tissue has been established.

Figure 14A:
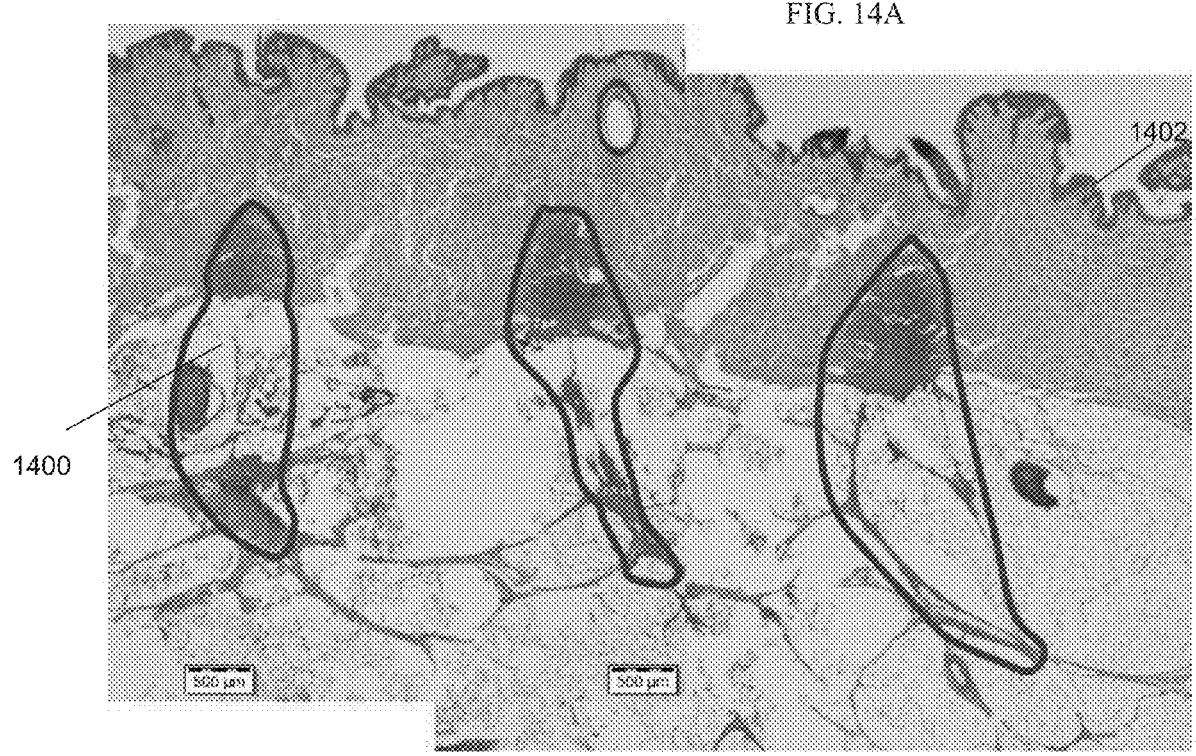
Figure 14B:
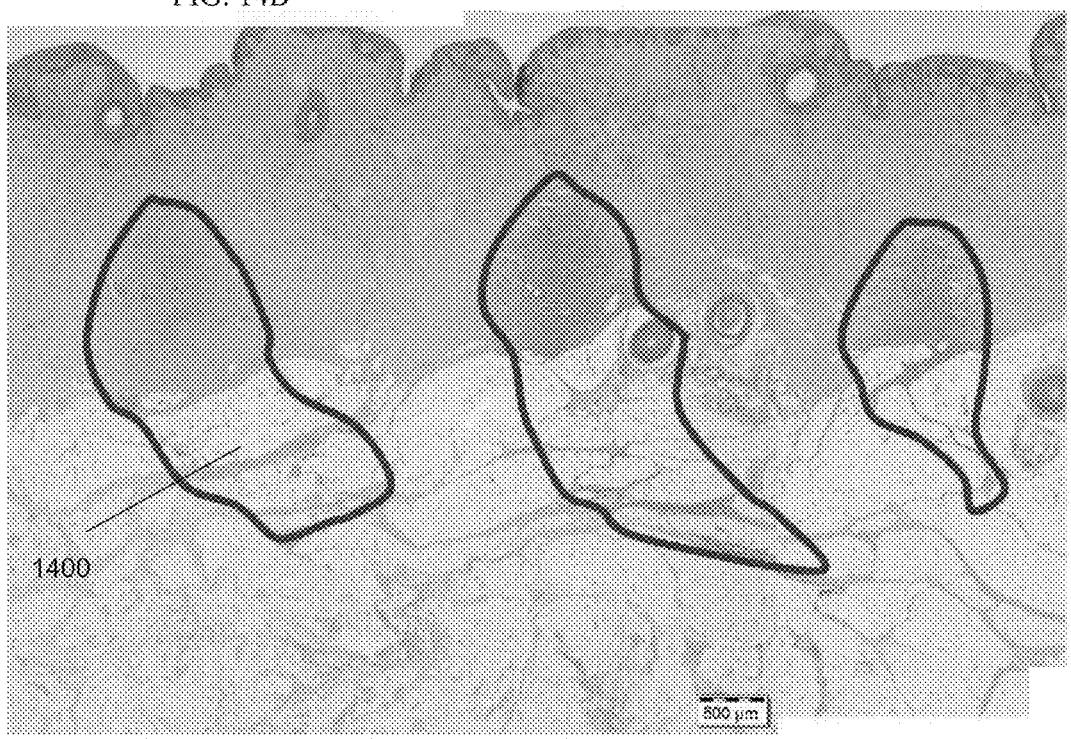

FIGS. 14A-D are histopathology slides obtained in a swine cadaver model during an experiment performed in accordance with some embodiments of the invention. FIGS. 14A-D show images obtained following treatment with unfocused ultrasound, using an applicator for example as described hereinabove in FIGS. 13A-B. In FIGS. 14A-B, unfocused ultrasound was emitted for a time period of 10 seconds, and cooling was applied simultaneously via the transducers. FIG. 14A shows the thermal effect of energy applied at an intensity of 21.5 W/cm^2. FIG. 14B shows the thermal effect of energy having a lower intensity, 18.3 W/cm^2. Spaced apart thermal damage regions 1400 were observed in the deep dermis, at a distance of at least 1 mm, at least 2 mm, at least 2 mm from the epidermis 1402. Substantially no damage was caused to the epidermis 1402.

Figure 14C:
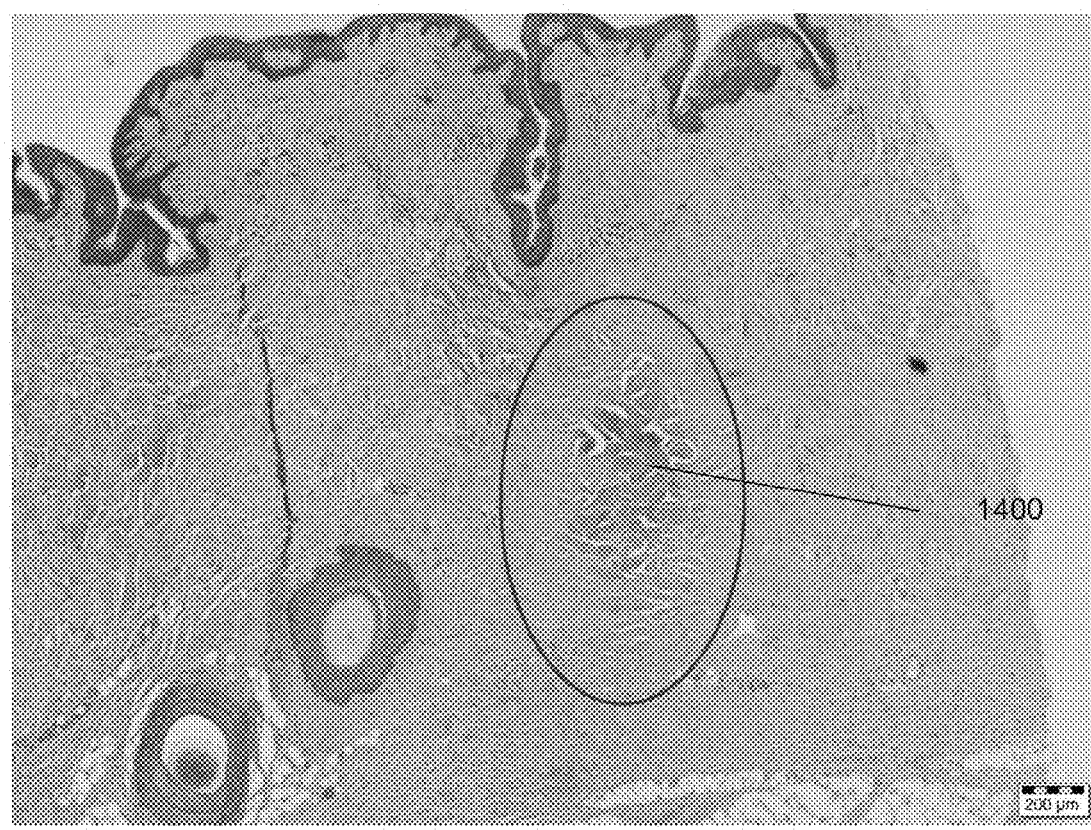
Figure 14D:
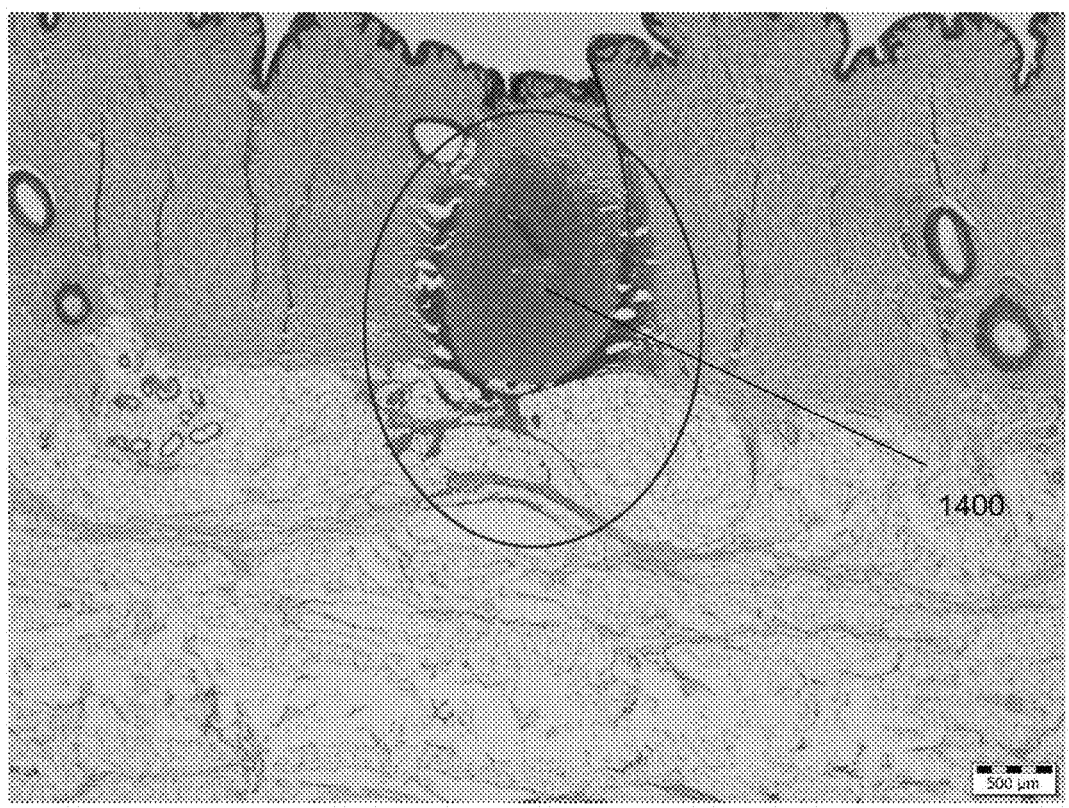

FIGS. 14C-D show the effect of treatment duration on the thermal damage. In FIG. 14C, unfocused ultrasound energy having an intensity of 22.5 W/cm^2 was applied for a time period of 10 seconds. In FIG. 14D, unfocused ultrasound energy having an intensity of 22.1 W/cm^2 was applied for a time period of 20 seconds. In both experiments, the skin temperature was maintained (by cooling) at a temperature of approximately 20 degrees Celsius.

In the experiments, the unfocused ultrasound was effective to raise a temperature of the tissue at the target regions to a temperature between 60-70 degrees Celsius for causing the thermal damage. In some embodiments, methods and/or devices for example as described herein may be used for aesthetic applications such as skin tightening, hair removal, treatment of excessive sweating, cellulite treatment and/or other aesthetic treatment.

FIGS. 15A-B histopathology slides obtained in-vivo in human skin during an experiment performed in accordance with some embodiments of the invention.

In this experiment, a device as described for example in FIGS. 13A-B was used for applying unfocused ultrasound onto human skin. FIG. 15A shows the results obtained by applying unfocused ultrasound at an intensity of 16 W/cm^2; FIG. 15B shows the results obtained by applying unfocused ultrasound at an intensity of 18 W/cm^2. In both, treatment was applied over a 10 second time period. Pre-cooling was applied to the skin over 5 seconds before emission of ultrasound. The skin surface temperature throughout the experiment was maintained at approximately 5 degrees C. The thermally damaged lesion is encircled by the black line.

FIGS. 16A1-J present various methods for assessing contact between the applicator and the skin, in accordance with some embodiments. In some embodiments, the contact is formed between a distal, emitting face of the transducer and the surface of the skin.

In some embodiments, contact of each of the one or more transducers of the applicator with the skin can be separately assessed. In some embodiments, contact is assessed prior to excitation of the transducers; additionally or alternatively, contact is assessed during and/or following excitation.

In some embodiments, if full or partial contact loss is detected, excitation is ceased. In some embodiments, a user (e.g. a physician) repositions the applicator on the skin until sufficient contact between all transducers and the skin is achieved. Optionally, sufficient contact between the transducer emitting face and the tissue surface is defined as having at least 70%, at least 80%, at least 90% of the surface area of the transducer's emitting face in contact with the tissue. Optionally, a thin layer of ultrasonic gel is applied at the interface between the transducer's emitting face and the skin.

In some cases, only partial contact between the transducer and the skin is preferred. For example, when treating scar dents (such as a scar dent formed due to acne), the dent may be filled with ultrasonic gel and the transducer will be placed on the skin such that only a part of it contacts skin surrounding the dent, and another part contacts the ultrasonic gel only. Optionally, the energy is transferred via the ultrasonic gel to the bottom of the scar dent.

In some embodiments, variations in one or more transducer parameters, in value and/or trend of parameters such as power, capacitance, a temperature of the transducer's emitting face and/or others are assessed to determine the quality of the contact with the skin. Optionally, a change in a parameter which is above a selected threshold is indicative of loss of contact.

FIG. 16A1 is a flowchart of a method for assessing contact between one or more transducers and the skin by measuring a temperature of the one or more transducers, according to some embodiments. In some embodiments, the applicator is positioned on the skin surface (1601). Optionally, the one or more transducers are activated (1603). In some embodiments, a temperature of one or more of the transducers (for example of the emitting face of the transducer) is measured (1605). In some embodiments, the transducer temperature is measured using one or more thermistors, located for example in between adjacent transducers of the applicator. Optionally, the measured temperature is of a thin coating of the transducer, being substantially similar to that of the transducer. In some embodiments, the temperature is measured periodically. Alternatively, the temperature is continuously monitored. In some embodiments, contact between the one or more transducers and the skin is assessed according to the temperature (1607). Optionally, a sudden change in temperature level and/or trend (e.g. a rise or drop in temperature) is indicative of loss of contact. In some embodiments, if loss of contact is detected, ultrasound emission is automatically ceased. In some embodiments, if loss of contact is detected, a user repositions the applicator on the skin surface (1609). Optionally, an automatic alert is provided to the user, potentially guiding the user how to reposition the applicator.

FIG. 16A presents a sudden change in temperature in multiple transducers of the applicator, during excitation of the transducers. In some embodiments, a sudden change in temperature during excitation is indicative of contact loss or change of the one or more transducers with the skin surface. In some cases, if the applicator is suddenly lifted or otherwise moved away from the skin surface, a temperature of the distal face of the transducer quickly rises. A rise in temperature during excitation may be caused due to the ultrasonic energy not being transmitted properly from the transducer surface to the skin, potentially resulting in excessive heating of the transducer, as most of the energy is converted to heat. At times in which no excitation is applied, lifting the applicator away from the skin may result in a sudden drop of transducer temperature, caused as a result of the active cooling of the transducer base and/or the loss of contact with the skin.

In some embodiments, a situation of interrupted contact with the skin (e.g. due to a sudden lift of the applicator from the skin surface) is detected by monitoring a temperature of the one or more transducers. In some cases, a temperature of the holder element of the applicator remains unchanged, while a temperature of the one or more transducers suddenly rises.

In some embodiments, the temperature of the one or more transducers is monitored in a closed feedback loop. Optionally, when the temperature rises above a threshold (or drops below a threshold), excitation is ceased. In an example, a high threshold above which excitation is ceased is set at 30 degrees, 32 degrees, 28 degrees, 37 degrees or intermediate, higher or lower temperatures. The change may be in an absolute value of the temperature, or in a relative value, or in a trend (slope) of the monitored temperature. In an example, a slope above which excitation is ceased is set at 1 degrees/sec, 1.5 degrees/sec, 3 degrees/sec, or intermediate, higher or lower ratios.

A potential advantage of ceasing activation when detecting a temperature value and/or trend beyond a threshold may include reducing a risk of permanent damage to the transducer, which may affect the transducer's efficiency or even disable its operation. Another potential advantage may include preventing damage to the skin (e.g. burns) which may be caused by an overheated piezo element, and/or reducing the likelihood of a non-uniform thermal effect on the skin.

Figure 16B:
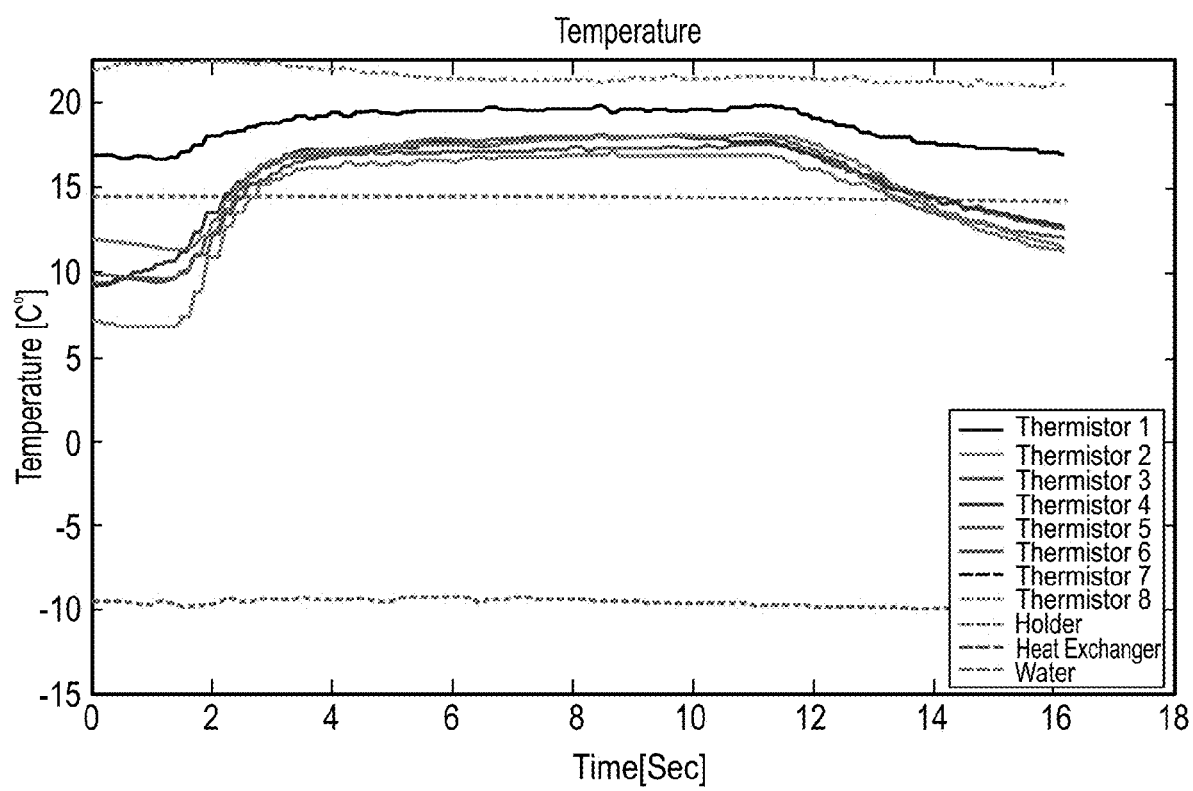

For comparison, FIG. 16B presents a measurement in which no sudden changes in temperature occurred. In this example, the measurement was performed over an 18 second period in which standard treatment excitation was applied.

Figure 16C:
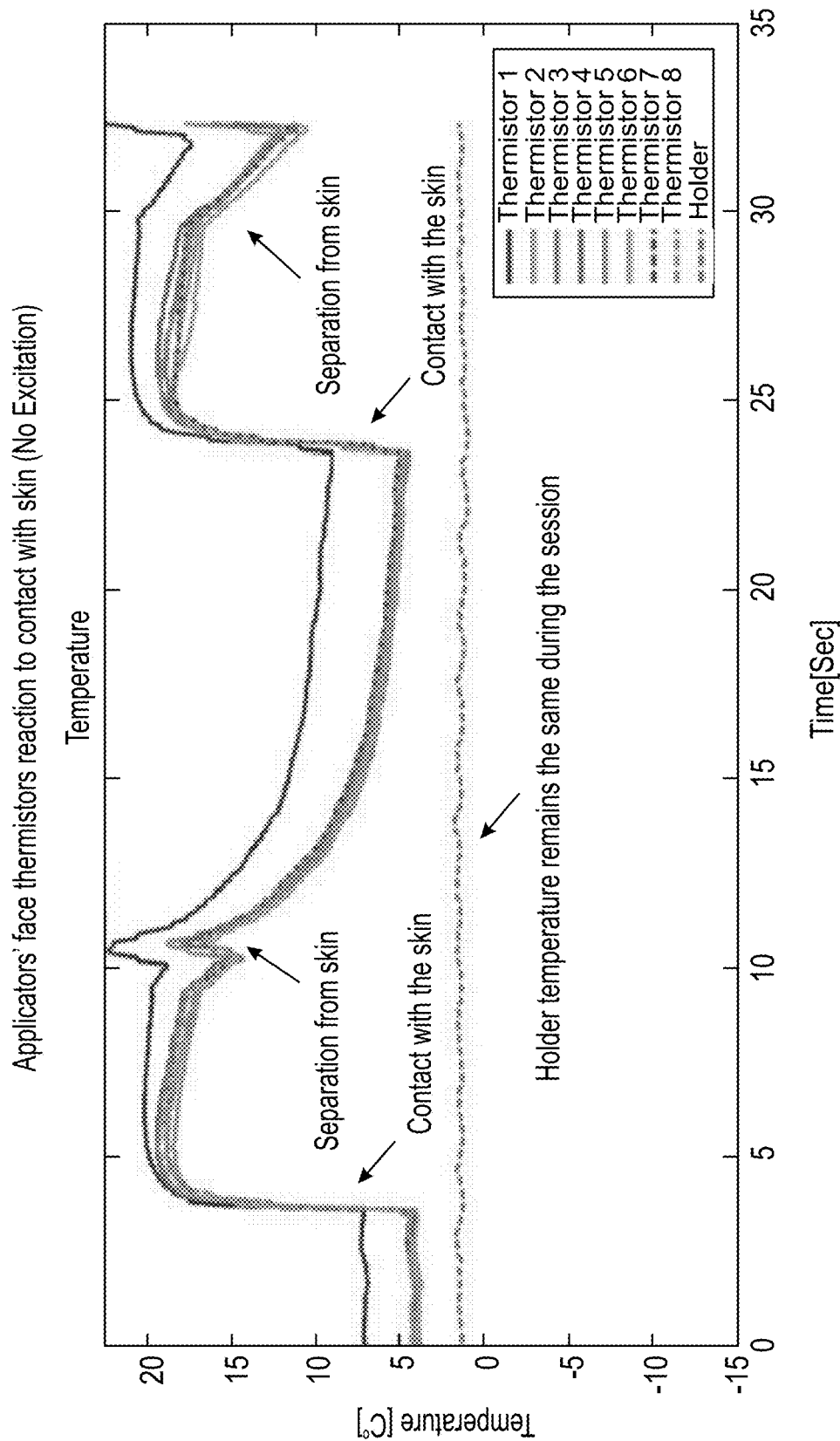

FIG. 16C presents a measurement of transducer temperatures obtained within a time period in which no excitation was performed, in accordance with some embodiments. The measurement indicates a temperature rise when contact is made with the skin, and a temperature drop when the applicator is moved away from the skin. As can be observed in this example, a temperature of the holder (e.g. a temperature of base 704, shown for example in FIG. 7) remains substantially the same during the measurement.

Figure 16D:
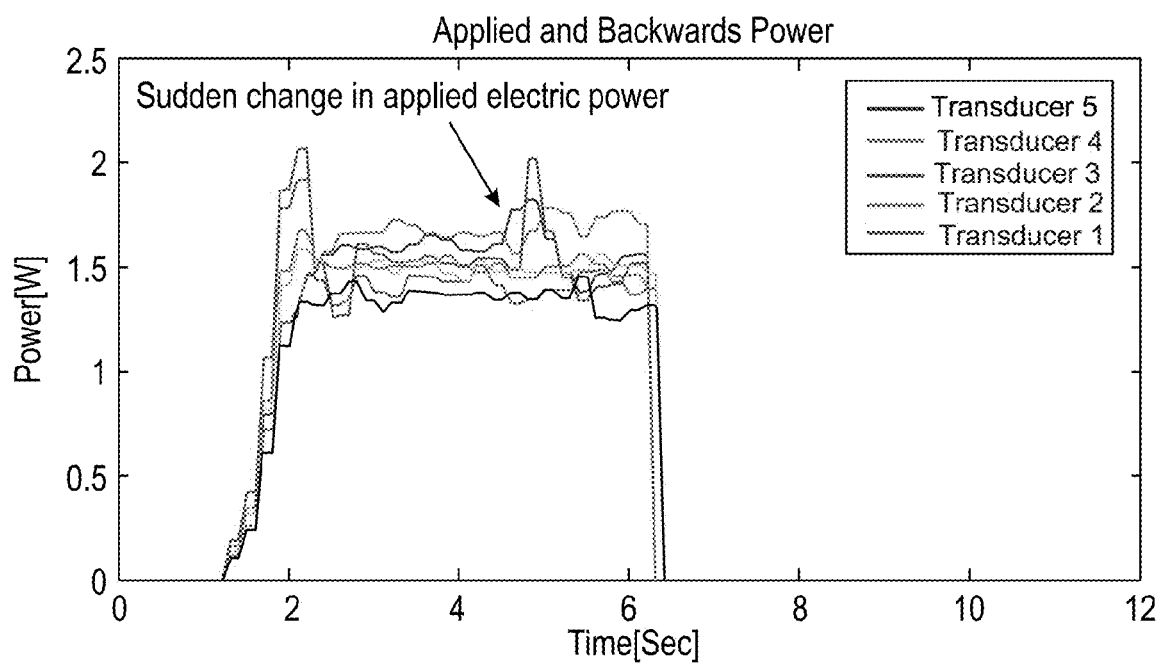

FIG. 16D1 is a flowchart of a method for assessing contact between one or more transducers and the skin by measuring power consumption of the one or more transducers, according to some embodiments. In some embodiments, the applicator is positioned on the skin surface (1611) and the one or more transducers are activated (1613). In some embodiments, a power consumed by the one or more transducers during operation is measured (1615), periodically or continuously. In some embodiments, loss of contact between the one or more transducers and the skin surface is assessed according to the consumed power levels of the transducers (1617). Optionally, a change in power above a certain threshold is indicative of loss of contact. In some embodiments, if loss of contact is detected, ultrasound emission is automatically ceased. In some embodiments, if loss of contact is detected, a user repositions the applicator on the skin surface (1619). Optionally, an automatic alert is provided to the user, potentially guiding the user how to reposition the applicator.

FIG. 16D presents a measurement in which sudden changes in the electric power applied to the transducer occurred. Optionally, a change in power is indicative of a change in the quality of contact with the skin. In some embodiments, the transducer impedance when the transducer is not in contact with the skin differs from the impedance when the transducer is in contact with the skin, thus affecting a power output of an amplifier supplying the transducer. In the exemplary measurement shown, a change in applied power was detected for three transducers (marked red, blue green). (The initial rise that appears in the graph is assumed to be a result of controller overshoot).

Figure 16E:
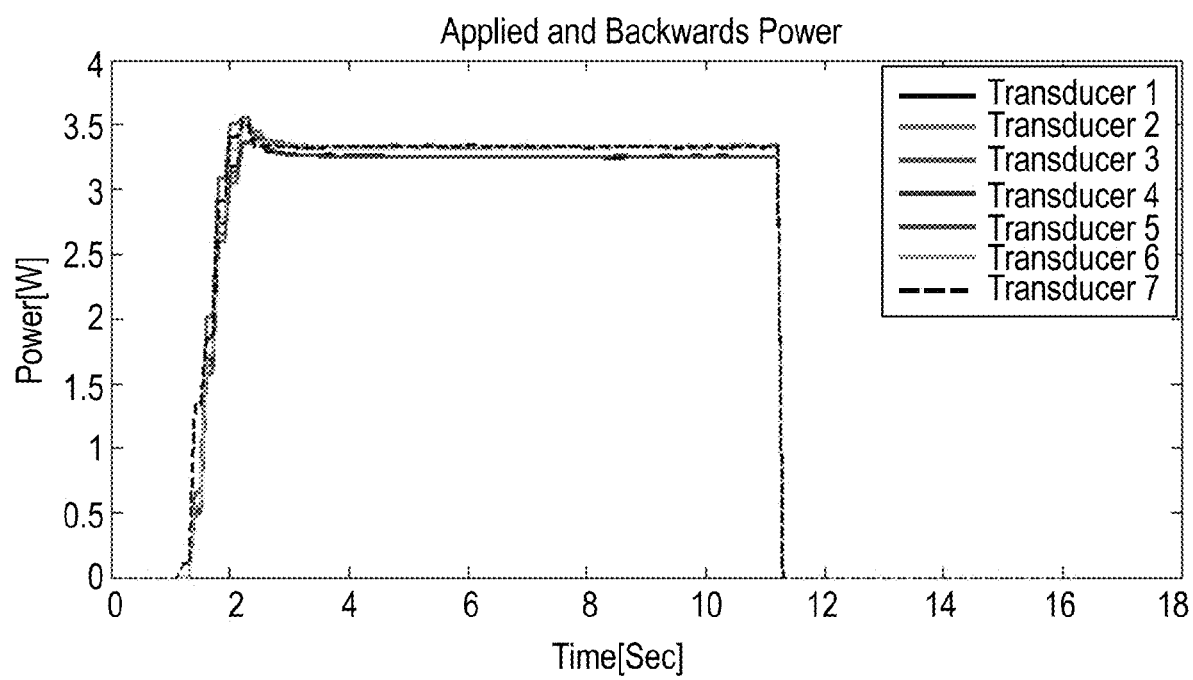

For comparison, FIG. 16E presents a measurement in which no sudden changes were observed.

Figure 16F:
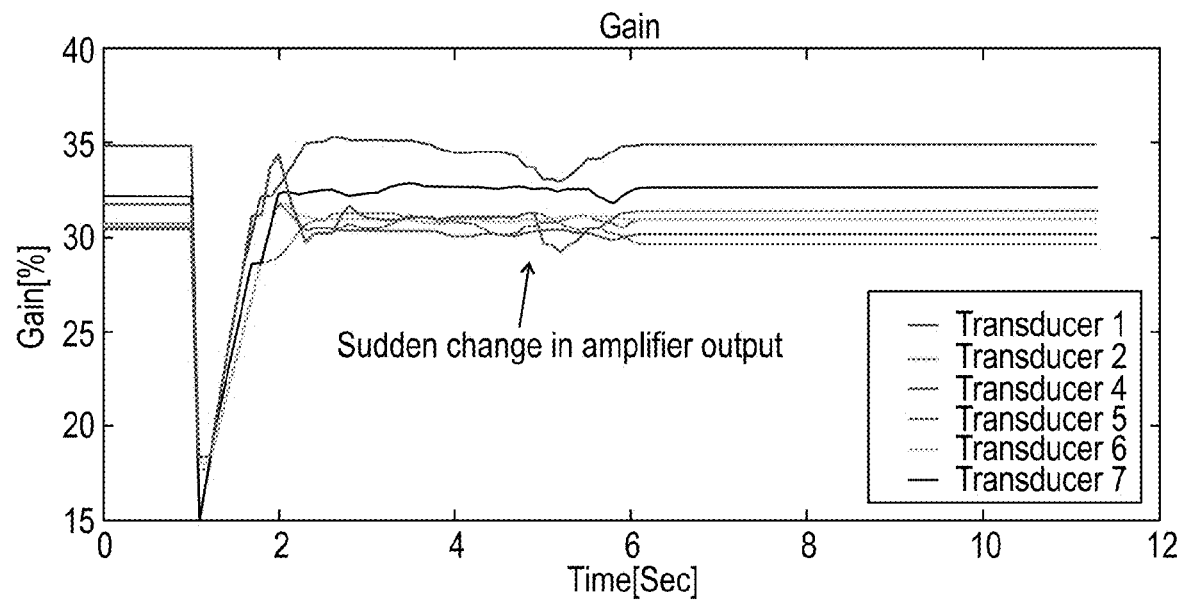

FIG. 16F1 is a flowchart of a method for assessing contact between one or more transducers and the skin by measuring amplifier gain associated with the one or more transducers, according to some embodiments. In some embodiments, the applicator is positioned on the skin surface (1621) and the one or more transducers are activated (1623). In some embodiments, a gain of an amplifier associated with the one or more transducers is measured during operation (1625). In some embodiments, loss of contact between the one or more transducers and the skin surface is assessed according to the change in amplifier gain (1627). Optionally, a change in amplifier gain above a certain threshold is indicative of loss of contact. In some embodiments, if loss of contact is detected, ultrasound emission is automatically ceased. In some embodiments, if loss of contact is detected, a user repositions the applicator on the skin surface (1629). Optionally, an automatic alert is provided to the user, potentially guiding the user how to reposition the applicator.

FIG. 16F presents a sudden change in the amplifier gain associated with two of the transducers (indicated by the red and blue lines). In some embodiments, a change in the amplifier gain is indicative of a change in the quality of contact with the skin. This correlation may be a result of a change in an electric impedance of the transducer, for example as described hereinabove. In some embodiments, during excitation, powering is controlled by a control loop, which sets the power on selected level. Optionally, a change in power causes the controller to adjust the amplifier gain accordingly.

Figure 16G:
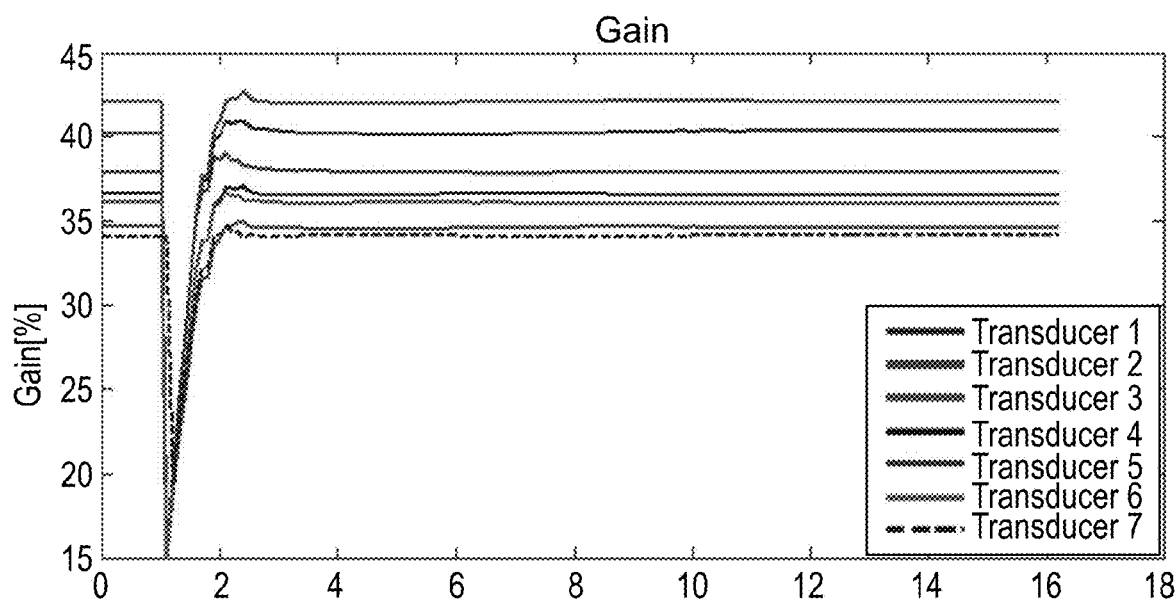

For comparison, FIG. 16G presents a measurement in which no major changes in the amplifier gain occurred.

Figure 16H:
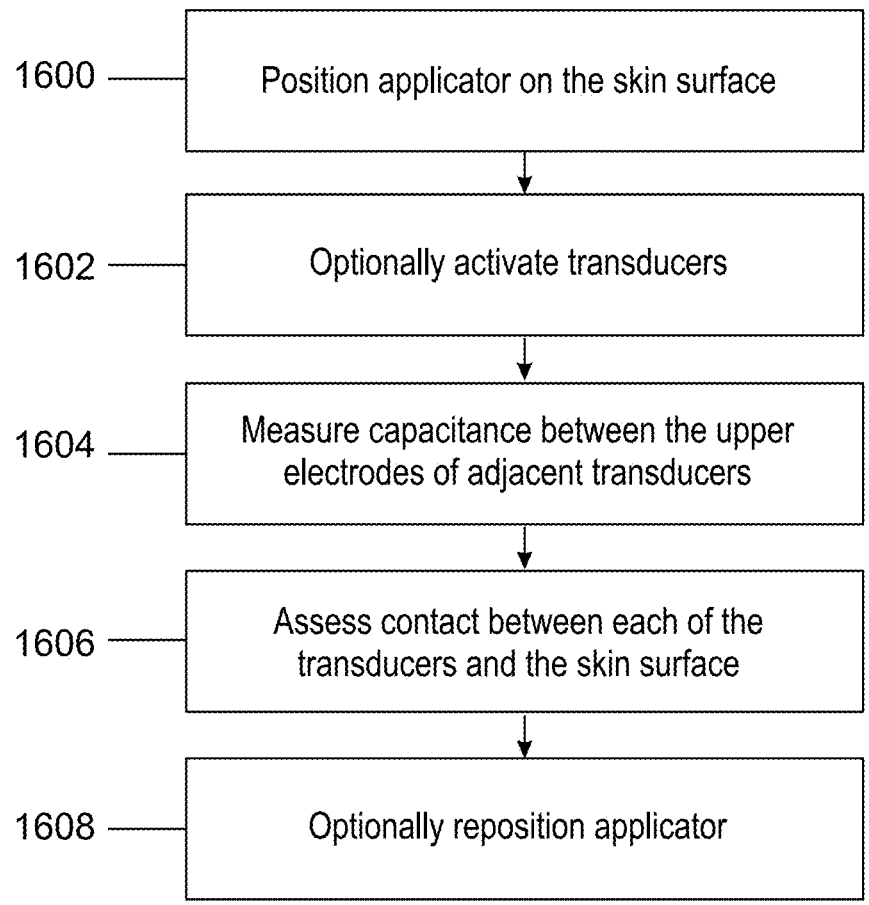
Figure 16I:
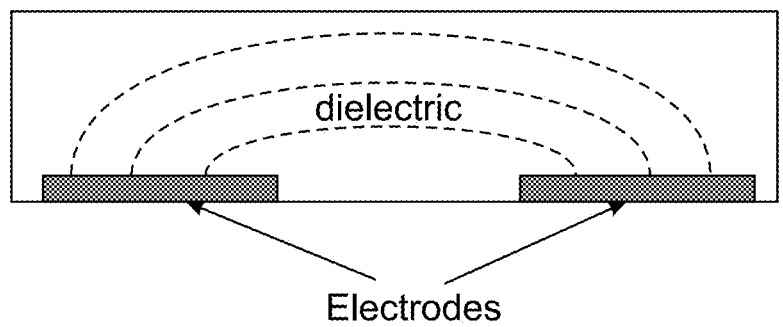

FIGS. 16H-I are a flowchart and a schematic illustration of a method for assessing contact between the transducers and the skin by measuring capacitance between the upper electrodes of adjacent transducers, according to some embodiments. In some embodiments, the capacitance varies as a function of the dielectric properties of material(s) located between the electrodes. In some embodiments, materials located intermediate the upper electrodes of the adjacent transducers include one or more of: a coating of the transducer (e.g. a layer of kapton), and entities contacting the coating, such as skin, ultrasonic gel, air or water. The measured capacitance is affected by the dielectric propreties of the one or more entities contacting the coating, therefore a change in capacitance may be indicative of the extent of contact between the transducer and the skin. As detailed in the flowchart of FIG. 16H, in some embodiments, the applicator is positioned on the skin surface (1600); optionally, the transducers of the applicator are activated (1602); in some embodiments, a capacitance is measured between upper electrodes of adjacent transducers (1604) for assessing contact between the transducers and the skin surface (1606). In some embodiments, a qualitive yes/no indication of contact is obtained; alternatively, measurement of the specific contact is performed, for example for calculating a percentage of the surface area of the transducer's emitting face contacting the skin. In some embodiments, if an indication of no or poor contact was received, the applicator is repositioned on the skin. In some embodiments, a baseline capacitance is measured when the applicator is held in the air, and an increase of at least 10%, at least 20%, at least 40% or intermediate, higher or lower values in the measured capacitance indicates that sufficient contact has been obtained with the skin. In an example, a 50 pF capacitance is measured as the baseline, and a 60 pF capacitance is indicative of sufficient contact with the skin.

Figure 16J:
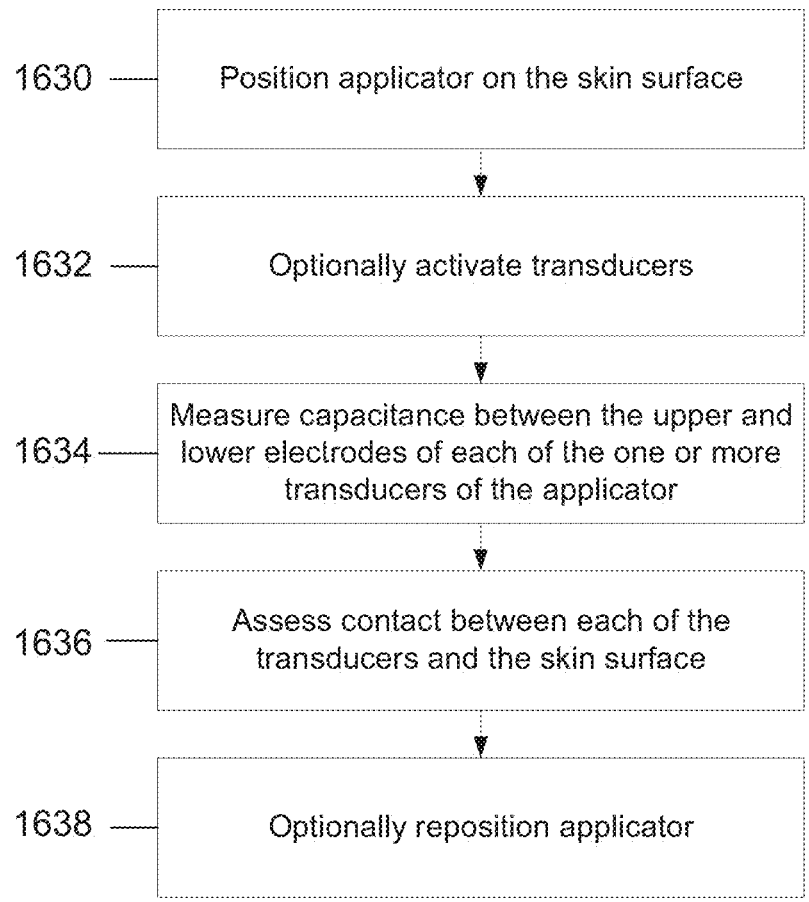

FIG. 16J is a flowchart of a method for assessing contact between the transducers and the skin by measuring capacitance between the upper electrode and the bottom electrode of each of the one or more transducers of the applicator, according to some embodiments. The upper and lower electrodes define a parallel-plate capacitor. In some embodiments, the transducer capacitance depends on a temperature of the transducer, for example with a relatively linear correlation of t=(C−700)/18.4 for a 8 mm^2 transducer area, and t=(C−575)/12.1 for a 5 mm^2 transducer area, where t is the temperature in Celsius, and C is the capacitance in Picofarad.

As detailed in the flowchart of FIG. 16J, in some embodiments, a process for example as described hereinabove in FIG. 16H is performed, except that capacitance is measured between upper and lower electrodes of one or more of each of the transducers of the applicator (1634).

Other methods for assessing a quality of contact between the transducer and the skin, according to some embodiments, may include:

Measuring an impedance of the transducer(s). Optionally, impedance measurements are carried out using a gain and phase detector component, such as AD8302, Analog Devices. Optionally, impedance samples are collected at a frequency rate of, for example, 10 Hz. A significant difference between the impedance levels measured when the transducer is in contact with the skin and when the transducer is in contact with air is presented.

Measuring an impulse response of the transducer(s).

Analyzing echo signals received by the one or more transducers to determine whether contact is established and/or indicate a distance of the transducer from the skin surface.

FIG. 17A is a flowchart of a general method for obtaining a desired treatment effect on the tissue, according to some embodiments.

In some embodiments, a desired effect and optionally a non-desired effect is selected (1700). Examples of desired effects may include: smoothing-out wrinkles; reducing a visibility of stretch marks; evening out skin complexion; and/or others. Examples of non-desired effects may include skin burn, damage to the epidermis, atrophic scarring and/or others.

In some embodiments, a desired effect is selected out of a short term effect, visible as soon as minutes, hours, or several days post treatment, or a long term effect, visible for example only weeks post treatment (e.g. 2 weeks, 4 weeks, 6 weeks). Optionally, both types of effects are attempted in the same treatment.

In some embodiments, a target tissue layer to be heated is selected according to the desired effects (1702). For example, a layer that is at a depth of 1 mm, 1.5 mm, 2 mm, 3 mm or intermediate, larger or smaller depths from the epidermis is selected as target. In some embodiments, one or more tissue layers (e.g. hypodermis, dermis, epidermis) are selected as target. Optionally, targeting a specific layer affects a total effect on the tissue.

In some embodiments, one or more treatment parameters such as ultrasound intensity, ultrasound frequency, a duration of treatment, and/or other parameters are selected for obtaining the desired effect and/or for avoiding non-desired effects.

In an example, in order to get the desired effect of skin tightening and wrinkle reduction, without causing any damage to the epidermis, the treatment frequency will be selected to be 11.5 MHz; the treatment duration will be 4 sec, the ultrasonic intensity will be 18-22 W/cm^2, and the transducer base cooling will be set to (−10) Celsius.

In some embodiments, treatment parameters are selected to produce thermal damage at a certain depth or depth range from the tissue surface; to produce thermal damage of a selected extent; to cover a selected cross-sectional area of the tissue; and/or others. In some embodiments, the parameters are automatically selected by the system controller, for example in response to a desired and/or non-desired effects received as input.

In some embodiments, treatment according to the selected parameters is applied, heating tissue in the target layer (1704). Optionally, treatment is carried out by a physician and/or other clinical personnel using methods and/or devices for example as described herein.

In some embodiments, if a desired effect was not or only partially arrived at, treatment is repeated (1705).

In some embodiments, control of the extent of the effects is achieved by controlling the heating profile. For example, heating the tissue to 55 degrees Celsius or higher will cause denaturation of the tissue; heating the tissue to 65 degrees Celsius or higher will thermally damage the tissue to a higher extent, potentially inducing the formation of a new collagen/elastin matrix which may impact long term effects.

FIG. 17B is a flowchart of a method for obtaining a short term effect, according to some embodiments. In some embodiments, a short term effect comprises an effect that is visible as soon as several minutes, several hours or several days post treatment. In some embodiments, a decision is made to produce a short term effect (1706), along with selecting of a target tissue layer to be heated for obtaining that desired effect (1708). Optionally, the target tissue layer for obtaining a short term effect is no more than 1 mm deep, no more than 1.5 mm deep, no more than 2 mm deep relative to the epidermis. Optionally, the target tissue layer is the dermis or a part of it.

In some embodiments, tissue in the target layer is heated to cause an inflammatory effect (1710). The inflammatory effect may include edema, swelling, and/or other effects that involve an immune response. In some embodiments, the short term effect is associated with denaturation of collagen, which may cause contracting of the tissue. In some embodiments, the short term effect is associated with temporary numbing of the tissue. In some embodiments, tissue in the target layer is heated to cause at most an inflammatory effect, but not heated enough to cause thermal damage that would induce long term effects.

In some embodiments, the short term effect lasts between 3 days to 3 weeks, for example between 3-10 days, 5-7 days, or intermediate, longer or shorter time periods. In some embodiments, a time period during which the short term effect remains visible (e.g visible to the human eye) depends on the applied intensity, in a manner that the higher the intensity applied—the longer the effect will last. In some embodiments, due to that only low or no damage is caused to the epidermis layer during treatment, an immediate aesthetic effect can be observed substantially without side effects of treatment such as skin redness and/or rashes. In some cases, redness is only a result of vasculature that is temporarily affected and not a result of thermal damage, and therefore redness, even if appears, may disappear after 1 hour, 2 hours, or 5 hours at most.

FIG. 17C is a flowchart of a method for obtaining a long term effect, according to some embodiments. In some embodiments, long term effect comprises an effect that is visible only at, for example, 3 weeks post treatment, 4 weeks post treatment, 6 weeks post treatment or intermediate, longer or shorter time periods.

In some embodiments, a decision is made to produce a long term effect (1712), along with selecting of a target tissue layer to be heated for obtaining that desired effect (1714). Optionally, the target tissue layer for obtaining a long term effect is at least 2 mm deep, at least 3 mm deep, at least 2.5 mm deep relative to the epidermis.

In some embodiments, tissue in the target layer is heated to cause thermal damage sufficient for inducing generation of a collagen and/or elastin matrix (1716). In some cases, a long term effect is visible when generation of collagen and/or fibroblasts takes place, as a part of the natural wound healing response of the body. In some embodiments, at 6 months post treatment, 5 months post treatment, 7 months post treatment or intermediate, longer or shorter time periods a desired predetermined long term effect is clearly observable on the treated tissue. The effect may improve over time, and change relative to the initial long term effect obtained may be observed even at 18 months post treatment. In some embodiments, the long term effect can be intensified and/or prolonged by applying a series of treatments. In an example, treatments are applied every 3-4 weeks. Optionally, timing is selected according to expected healing of the tissue. Optionally, a number and/or timing of treatments is selected based on the skin condition. Optionally, if the skin has healed enough from the previous treatment and no inflammation is present, another treatment can be applied. In some embodiments, positioning of the applicator and/or even a spacing of the transducers on the applicator is adjusted to enable further coverage, such as to ensure that regions that were previously unaffected will be affected at the next treatment.

FIG. 18 is a flowchart of a method for combining ultrasonic treatment and a second treatment, according to some embodiments.

In some embodiments, a decision is made (e.g. by a physician, cosmetician and/or other clinical personnel) to treat a subject with combined treatment (1800), including ultrasonic treatment using methods and/or devices for example as described hereinabove, and second treatment, including, for example, injection of hyaluronic acid, applying of a creme, and/or others.

In some embodiments, parameters of the ultrasonic treatment are selected (1802), for example selected in accordance with the target tissue layer. In some embodiments, parameters are selected to reach a target tissue layer or site that are meant to interact with the second treatment. For example, in the case of the second treatment being filler injection, the target tissue layer comprises a layer deeper than the dermis, such as the SMAS (Superficial muscular aponeurotic system) or the hypodermis. Alternatively, in some embodiments, the target tissue layer or site are selected not to interact with the second treatment.

In some embodiments, following applying ultrasonic treatment (1804), and optionally after waiting a selected time period (1806) such as for allowing an effect to take place in the tissue, for example 1-24 hours post treatment, 1-3 days post treatment, or intermediate, longer or shorter time periods, the second treatment is applied (1808). Optionally, the second treatment is performed immediately following ultrasonic treatment, such as 1-30 minutes after treatment. In some embodiments, the second treatment is performed before the ultrasonic treatment, days, hours or minutes before. In some embodiments, the second treatment targets the site treated by ultrasonic treatment, or a site adjacent to it.

In some embodiments, the ultrasound energy targets a layer at a certain depth, for example a layer deeper than the dermis, and the second treatment (e.g. filler injection) targets that layer and/or a layer located adjacent the targeted layer.

In the case of filler injection being the second treatment, a potential advantage of treating tissue with ultrasound prior to injecting a filler may include reducing or preventing a need for additional filler injection, thereby reducing exposure to external pathogens. In addition, as the ultrasonic treatment spares the epidermis from damage, the skin remains less exposed to external infections, allowing for immediate injection of the filler via the undamaged epidermis.

In some embodiments, the ultrasonic treatment causes loosening of connective tissue, which may reduce the amount of pressure that needs to be applied during injection for delivering the filler to the target location. In some embodiments, the ultrasonic treatment generates tunnels and/or regions of thermally damaged connective tissue through which the filler can be guided.

Optionally, one or both of the treatments are repeated (1810). Optionally, a decision to repeat is made upon an immediate and/or a midterm and/or long term effect of the combined treatment.

FIGS. 19A-L are various results obtained in a live swine model experiment, performed in accordance with some embodiments.

The table of FIG. 19A lists various exemplary parameters used in the swine experiment, including a setup in which 7 active transducers were used, driven at a frequency of 11.5 MHz, and activated for a treatment duration of 4 seconds after a 1 second pre-cooling period. The average temperature of the skin increased from 6.5 degrees post cooling and before treatment to 11.4 degrees post treatment.

FIGS. 19B-I are histopathology images obtained at various ultrasound intensities applied during the experiment. The tissue samples were obtained about 1 hour post treatment (of the sacrificed animal).

Figure 19B:
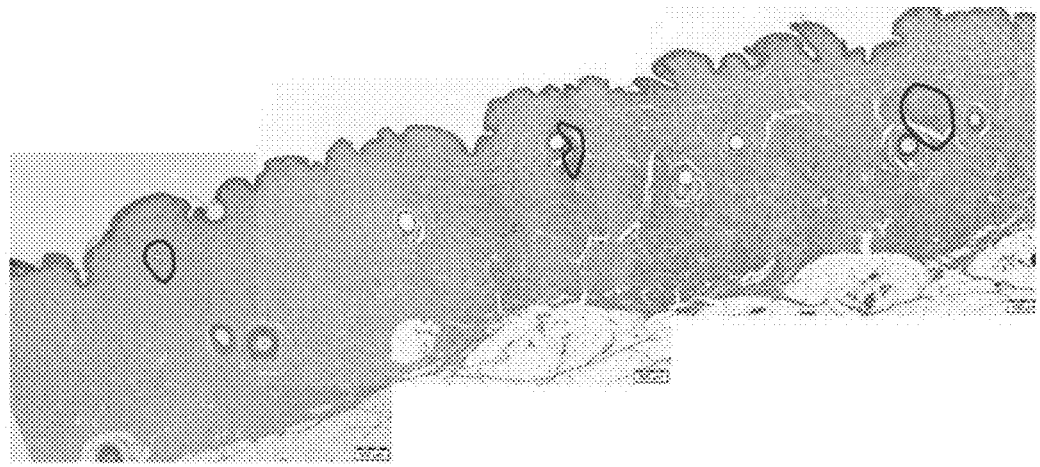
Figure 19C:
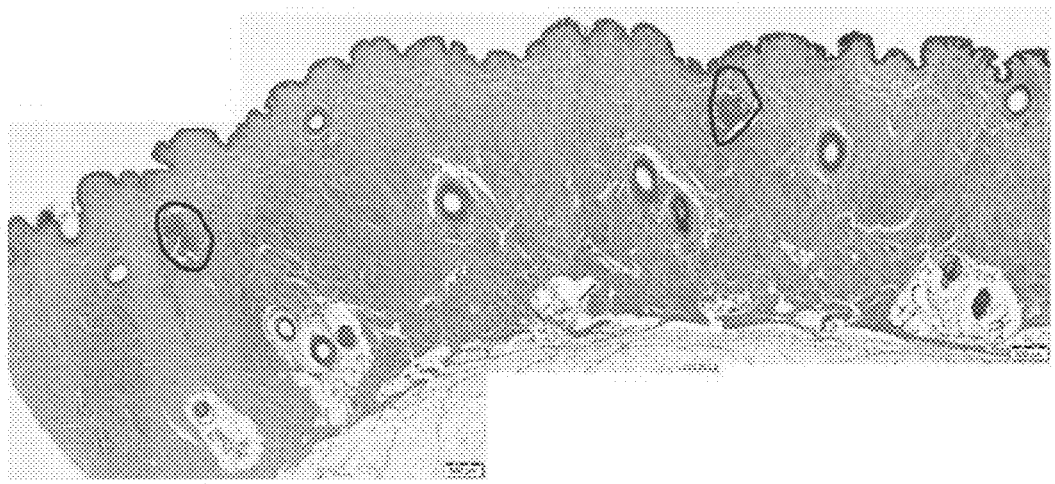
Figure 19D:
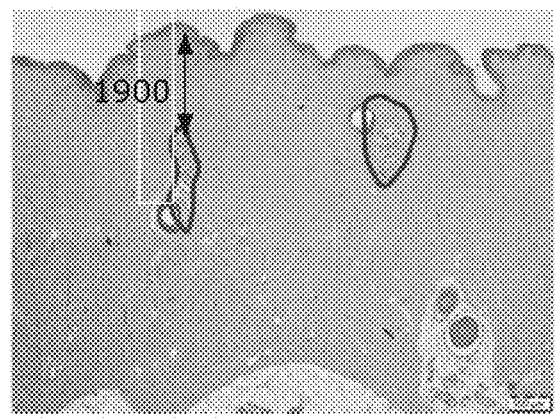
Figure 19E:
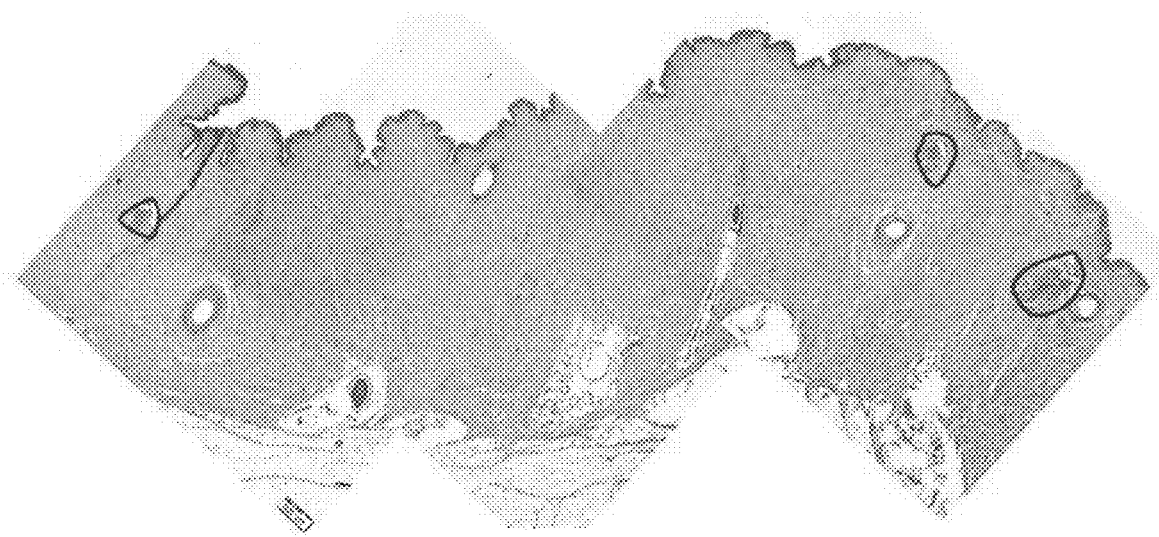
Figure 19F:
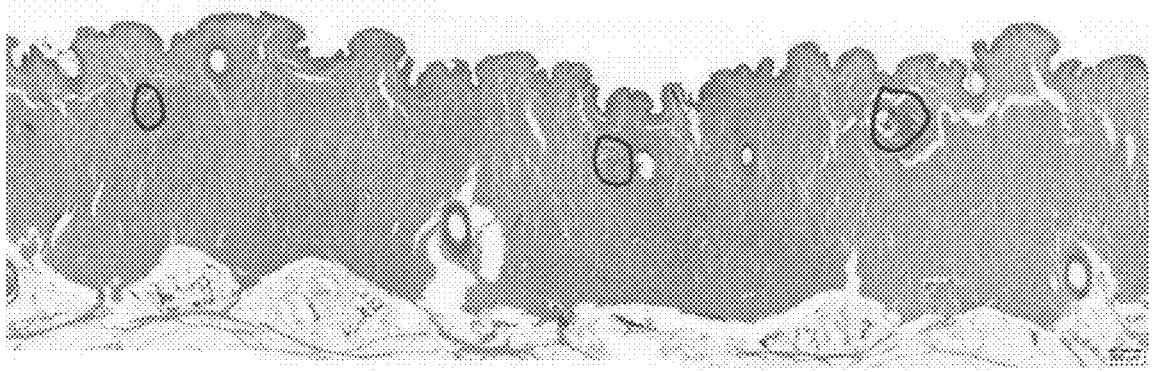
Figure 19G:
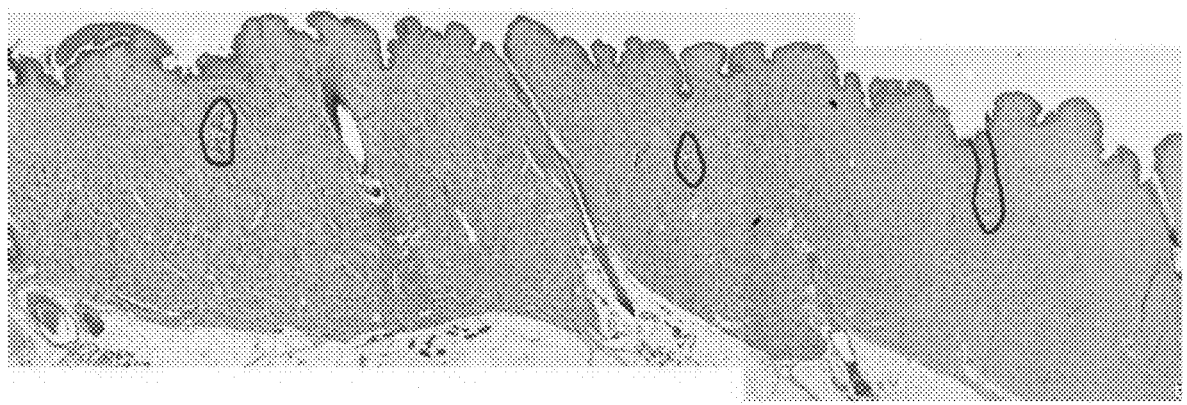
Figure 19H:
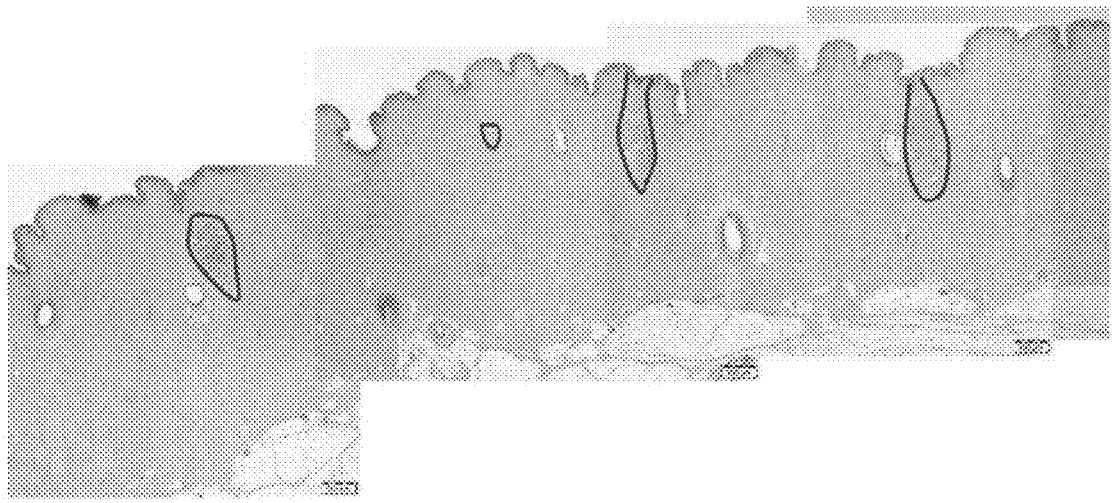
Figure 19I:
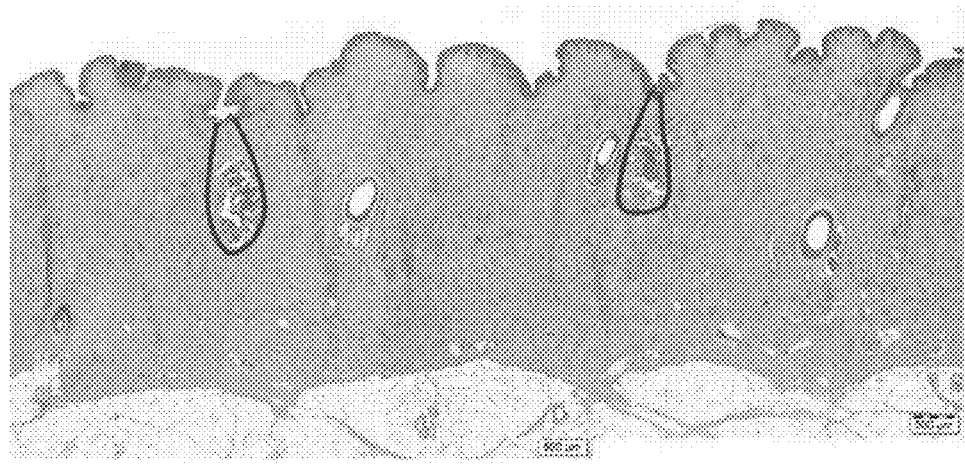

As can be observed, higher intensities produced thermal damage (encircled regions) that starts closer or even at the epidermis layer (see for example FIGS. 19G-19I), as compared to lower intensities, in which the thermal damage started a distance from the epidermis, such as a distance 1900 of at least 1 mm from the epidermis (see for example FIG. 19D). In some embodiments, the extent of thermal damage is assessed by estimating collagen denaturation, observable in the image as an area that is smudged. Optionally, the larger the extent of smudging, the higher the thermal damage. In some cases, observing of numerous cell death and/or an initial disruption of collagen fibers only, without substantial collagen denaturation, are indicative of a relatively low level of thermal damage.

In some embodiments, higher intensities are applied to cause a higher extent of damage and/or target deeper tissue layers; in some embodiments, lower intensities are applied to target tissue layers in proximity to the epidermis and/or to reduce the extent of thermal damage; in some embodiments, excitation duration is increased to obtain a higher extent of thermal damage.

Figure 19J2:
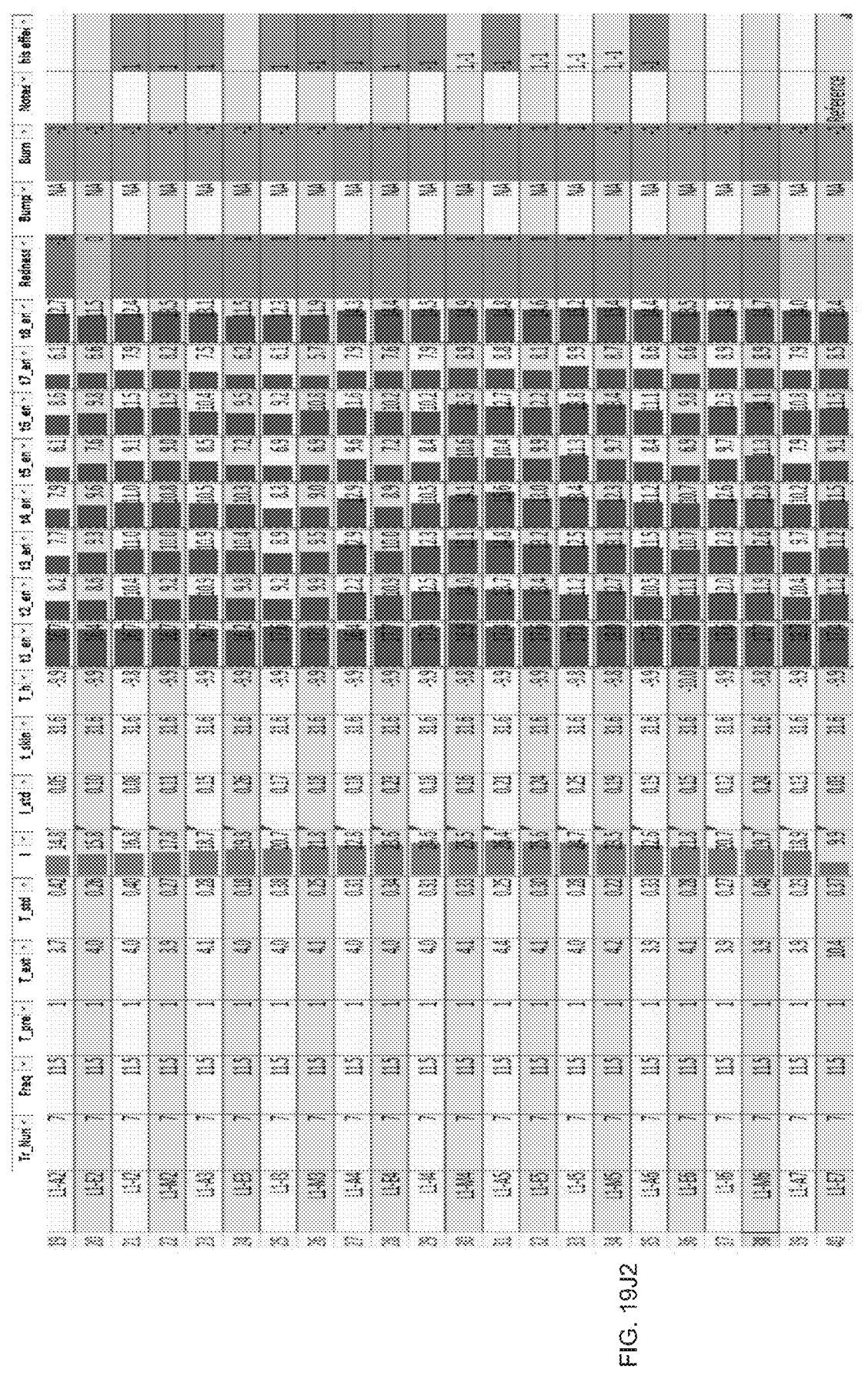
Figure 19L:
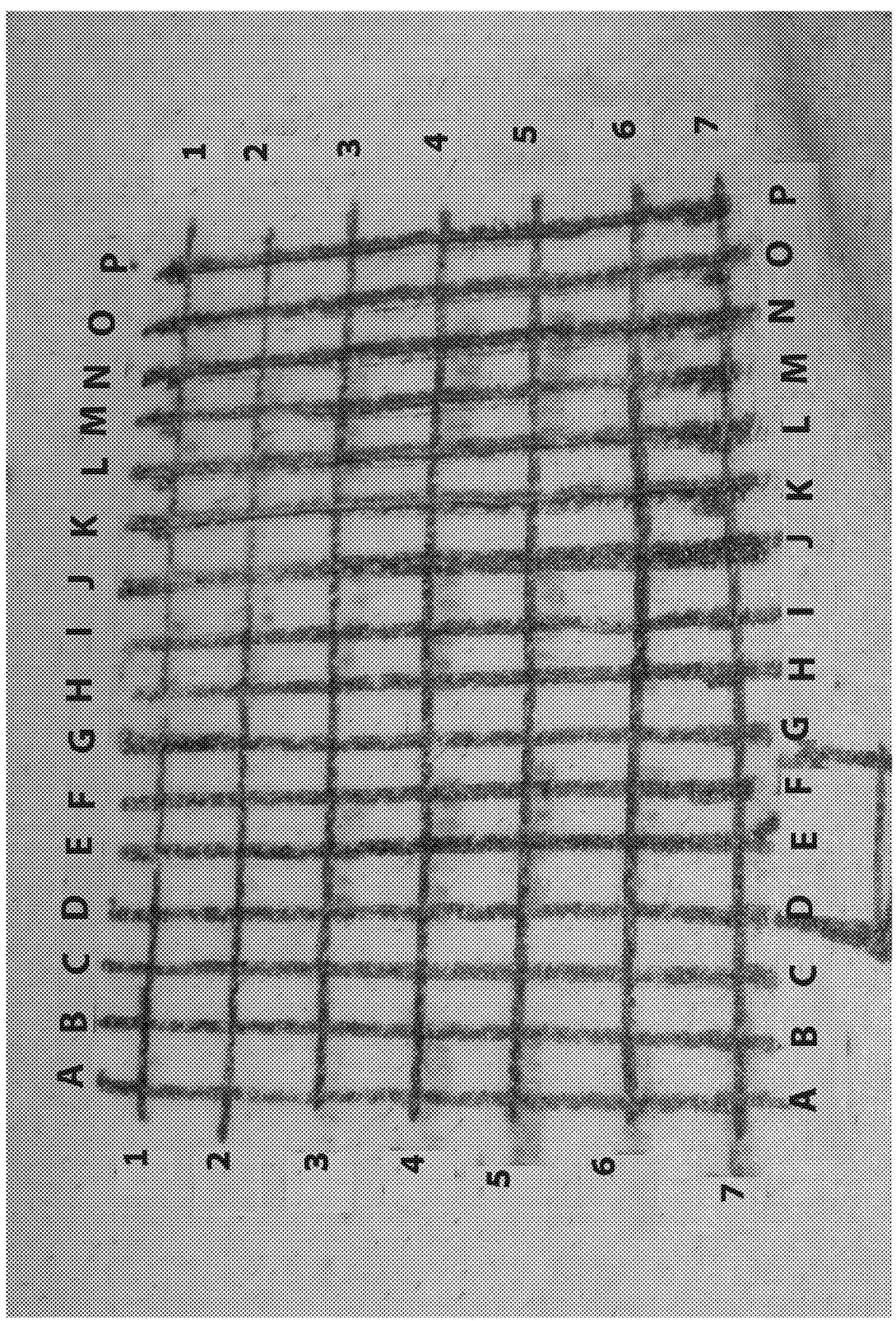

FIGS. 19J1-2 are two parts of a table summarizing experiment parameters and their corresponding results. FIG. 19K includes a legend for the table; FIG. 19L is a matrix drawn on the swine epidermis, showing the treatment points (locations) that are referred to in the first column of the table of FIG. 19J1-2.

The table of FIG. 19J1-2 refers to two treatment setups: a first treatment setup recorded in rows 2-18, in which a single transducer was activated; and a second treatment setup recorded in rows 19-40, in which 7 transducers were activated. In both of the setups, the applicator was moved between the different locations, and temperatures were measured at the end of excitation by thermistors located intermediate the transducers.

Based on the results, the inventors have made the following observations:

In some embodiments, increasing the intensity above a certain threshold may cause visible damage to the uppermost surface of the epidermis (marked in the table as the "burn" column). The intensity threshold varies based on the number of transducers that are activated: for example, when a single transducer was activated, a damage to the surface of the epidermis first appeared only at an intensity of 32.8 W/cm^2; when all 7 transducers were activated, a damage to the surface of the epidermis first appeared at an intensity of 22.8 W/cm^2. One of the possible reasons for this is that when a plurality of transducers are activated, lateral heating (i.e. in between adjacent working transducers) produces more rapid heating of the tissue as compared to only a single working transducer. Optionally, lateral cooling (e.g. in between the transducers) is applied.

In some embodiments, the outermost transducers of the transducer row of the applicator (transducers located adjacent the 1$^{st}$ and 8$^{th}$ thermistors) are heated more than the inner transducers. One of the possible reasons for this is that the active cooling applied via the applicator is less effective at the sides of the applicator.

The following tables summarize a histological effect obtained at two setups (1 active transducer and 7 active transducers), for different excitation durations: the Table 1 summarizes the results of a 5 second excitation of the transducers, and the Table 2 summarizes the results of a 10 second excitation of the transducers. As can be observed, in some embodiments, lengthening the excitation duration compensates for the intensity level, so that a lower intensity level can be used with an extended duration to reach an effect similar to the effect obtained by a higher intensity and shorter duration.

TABLE 1

| Number of active transducers | Intensity range w/cm2 | Histological effect | redness |
|---|---|---|---|
| 1 | 10-17 | No effect | + |
|   | 17/18-28 | No Effect in the epidermis Effect in the dermis | + |
|   | 30-34 and more | Effect in the epidermis and dermis | + |
| 7 | 10-15 | No effect | + |
|   | 16-21 | No Effect in the epidermis Effect in the dermis | + |
|   | 21-28 and more | Effect in the epidermis and dermis | + |

TABLE 2

| Number of active transducers | Intensity range w/cm2 | Histological effect | redness |
|---|---|---|---|
| 1 | 8-9 | No effect | + |
|   | 10-14 | No Effect in the epidermis Effect in the dermis | + |
|   | 14-28 and more | Effect in the epidermis and dermis | + |
| 7 | 6-9 | No effect | + |
|   | 9-12/13 | No Effect in the epidermis Effect in the dermis | + |
|   | 12/13- and more | Effect in the epidermis and dermis | + |

FIGS. 20A-B are photographs of treated human skin (in-vivo) at 1 and 2 days post treatment.

The photographs present the different intensities applied to different regions of the chest skin, one day post treatment (FIG. 20A) and two days post treatment (FIG. 20B). Treatment was performed by applying precooling for 1 second; exciting the transducers for 5 seconds; and cooling again for 5 seconds.

As can be observed, in a similar manner to the swine experiment, relatively high ultrasound intensity level resulted in visible thermal damage at the surface of the epidermis, as shown for example for intensities of 23 [W/cm^2] or higher. Most of the visible marks fully healed after about 1 week.

For some of the intensities, skin redness appeared immediately following treatment, and was no longer visible after a few hours.

The following table summarizes a histological effect obtained when treating human skin:

| Number of active transducers | Intensity range w/cm2 | effect | redness |
|---|---|---|---|
| 7 | 12-22 | No Effect in the epidermis | + |
|   | 22- and more | Effect in the epidermis and dermis | + |

It is noted that a maximal intensity above which visible thermal damage is caused to the epidermis may vary between subjects, for example according to gender (in an example, a maximal intensity for adult men is 22 w/cm^2, and a maximal intensity for adult women is 20 w/cm^2); baseline skin temperature; age; skin type; skin sensitivity and/or others.

FIG. 21 is a schematic illustration showing a contiguous damage effect on tissue, according to some embodiments of the invention.

In some embodiments, as shown for example in this illustration, a plurality of spaced apart thermal damage regions 2100 such as layers at the dermis layer are connected to each other by an elongate thermally damaged region 2102, extending for example along the hypodermis. Exemplary treatment parameters for obtaining this effect may include a frequency of 11.0 MHz, an excitation duration of 30 sec, an intensity of 20 W/cm^2, and a base temperature of (−15) ° C.

FIG. 22 is a histopathology image showing ablation of hair follicles, according to some embodiments. In some embodiments, the applied energy is suitable to ablate hair follicles, reducing or preventing future hair growth. In some embodiments, to ablate hair follicles, the target layer comprises the border between the dermis and the hypodermis layers, for example at a depth of 2-5 mm from the epidermis.

Exemplary treatment parameters used for ablation of hair follicles may include a frequency of 11.5 MHz, an excitation duration of 30 sec, an intensity of 16 W/cm^2, a base temperature of (−10) ° C.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As will be appreciated by one skilled in the art, aspects of the present invention may be embodied as a system, method or computer program product.

Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system".

Furthermore, aspects of the present invention may take the form of a computer program product embodied in one or more computer readable medium(s) having computer readable program code embodied thereon. Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing.

More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method for treating skin, comprising:
    applying to a skin surface an applicator comprising an array of spaced-apart individual energy emitting transducers, wherein said individual transducers are arranged on a surface of said applicator shaped and sized to contact skin surface, wherein said spaced-apart individual energy-emitting transducers comprise spaced-apart ultrasound transducers configured to emit unfocused ultrasound energy;
    emitting unfocused ultrasound energy from one or more of said energy emitting individual transducers with parameters selected to generate a thermal damage in deep tissue layers of the skin, wherein each of said one or more individual energy emitting transducers generate a separate thermal damage lesion in said deep tissue layers;
    assessing temperature of a skin surface contacting said one or more of said individual energy emitting transducers during said emitting by at least one temperature sensor located in between adjacent spaced-apart individual energy emitting transducers, wherein said at least one temperature sensor is mounted on a flexible film contacting a surface of at least one energy-emitting transducer of said spaced-apart individual energy-emitting transducers, facing a distal face of the applicator;
    cooling said skin surface contacting said applicator via said one or more of said individual energy emitting transducers during said emitting energy, to reduce thermal damage to said skin surface.

2. A method according to claim 1, comprising modifying at least one of frequency and intensity of said emitted unfocused ultrasound energy according to results of said assessing temperature.

3. A method according to claim 1, comprising:
    assessing indirect contact between one or more of said ultrasound transducers with said skin surface based on results of said assessing temperature of said skin surface.

4. A method according to claim 1, wherein said assessing temperature comprises assessing temperature of at least one of each of said ultrasound transducers and a temperature of a base on which said ultrasound transducers are mounted.

5. A method according to claim 1, wherein said cooling comprises cooling said skin surface to maintain a temperature of an epidermis between 5-40 degrees Celsius.

6. A method according to claim 1, comprising:
    generating said thermal damage in a tissue layer at a depth of 0.5-5 mm from an epidermis, by said emitted energy.

7. A method according to claim 1, wherein said applying to said skin surface comprises applying to said skin surface an array comprising 5, 7 or 9 ultrasound transducers.

8. A method according to claim 1, comprising: modifying one or more parameters of said emitting according to said assessing.

9. A method according to claim 1, wherein said cooling comprises cooling said skin surface according to said assessing temperature.

10. A method according to claim 1, wherein adjacent ultrasound transducers are separated by a space, and wherein said at least one temperature sensor comprises a plurality of temperature sensors, wherein at least one of said plurality of temperature sensors is positioned in said space between said adjacent spaced-apart ultrasound transducers.

11. A method according to claim 1, wherein said cooling comprises cooling of said skin surface contacting said applicator according to assessed temperature of said skin surface.

12. A method according to claim 1, wherein said at least one temperature sensor used for said assessing is located in proximity of up to 1 mm from an emitting surface of said one or more individual energy emitting transducers.

13. An applicator for applying energy to a skin tissue volume, comprising:
   a distal face shaped and sized to contact a skin surface;
   a plurality of spaced-apart individual energy-emitting transducers arranged in an array on said distal face, each of said individual energy-emitting transducers is configured to emit energy suitable to thermally damage at least a portion of a deep skin tissue volume in deep tissue layers of the skin; wherein each of said individual energy emitting-transducers is configured to generate a separate thermal damage lesion in said deep tissue layers;
   one or more temperature sensors positioned between said spaced-apart individual energy-emitting transducers, configured to indicate a temperature of a skin surface; and
   a cooling module configured to apply cooling via said one or more individual energy-emitting transducers to said skin surface contacting said distal face to reduce thermal damage to said skin surface;
   wherein said plurality of spaced-apart individual energy-emitting transducers comprises spaced-apart ultrasound transducers configured to emit unfocused ultrasound energy; and wherein said one or more temperature sensors are mounted on a flexible film contacting a surface of at least one ultrasound transducer of said spaced-apart ultrasound transducers, facing the distal face of the applicator.

14. An applicator according to claim 13, wherein said one or more temperature sensors are positioned between said plurality of spaced-apart individual energy emitting transducers.

15. An applicator according to claim 13, wherein said one or more temperature sensors are at least one of positioned on and in proximity to one or more of said ultrasound transducers, and are configured to indicate a temperature of said skin surface and a temperature of said one or more ultrasound transducers.

16. An applicator according to claim 13, comprising a heat transferring base having a plurality of branches, and wherein each of said ultrasound transducers is mounted on a separate branch of said heat transferring base, and wherein said one or more temperature sensors is positioned between said branches.

17. An applicator according to claim 16, comprising at least one additional temperature sensor contacting said heat transferring base, configured to indicate a temperature of said heat transferring base.

18. An applicator according to claim 13, wherein said one or more temperature sensors comprises one or more thermistors.

19. An applicator according to claim 13, wherein said plurality of ultrasound transducers comprises 5, 7, or 9 ultrasound transducers.

20. A method for treating skin, comprising:
   applying to a skin surface an applicator comprising an array of spaced-apart individual ultrasound transducers, wherein said individual ultrasound transducers are arranged on a surface of said applicator shaped and sized to contact skin surface, wherein each of said spaced-apart individual ultrasound transducers is mounted on a separate branch of a heat transferring base having a plurality of branches;
   emitting unfocused ultrasound energy from one or more of said individual ultrasound transducers with parameters selected to generate a thermal damage in deep tissue layers of the skin, wherein each of said one or more individual ultrasound transducers generates a separate thermal damage lesion in said deep tissue layers;
   assessing temperature of a skin surface contacting said applicator during said emitting by at least one temperature sensor located in between adjacent spaced-apart ultrasound transducers and between said plurality of branches;
   cooling said skin surface contacting said applicator via said one or more of said individual ultrasound transducers during said emitting energy according to said assessing temperature, to reduce thermal damage to said skin surface; and
   modifying one or more parameters of said emitting according to said assessing.

21. An applicator for applying energy to a skin tissue volume, comprising:
   a distal face shaped and sized to contact a skin surface;
   a plurality of spaced-apart individual energy-emitting transducers arranged in an array on said distal face, each of said individual energy-emitting transducers is configured to emit energy suitable to thermally damage at least a portion of a deep skin tissue volume in deep tissue layers of the skin; wherein each of said individual energy emitting-transducers is configured to generate a separate thermal damage lesion in said deep tissue layers, wherein said plurality of spaced-apart individual energy-emitting transducers comprise spaced-apart ultrasound transducers configured to emit unfocused ultrasound energy;
   one or more temperature sensors positioned between said spaced-apart individual energy-emitting transducers, configured to indicate a temperature of a skin surface contacting said distal face; and
   a cooling module configured to apply cooling via said one or more individual energy-emitting transducers to said skin surface contacting said distal face to reduce thermal damage to said skin surface;
   a heat transferring base having a plurality of branches, and wherein each of said ultrasound transducers is mounted on a separate branch of said heat transferring base, and wherein said one or more temperature sensors is positioned between said branches.

* * * * *